(12) United States Patent
Tomimori et al.

(10) Patent No.: US 8,334,261 B2
(45) Date of Patent: *Dec. 18, 2012

(54) OSTEOPENIA ANIMAL MODEL

(75) Inventors: Yoshiya Tomimori, Shiga (JP); Hisataka Yasuda, Shiga (JP)

(73) Assignee: Oriental Yeast Co., Ltd., Tokyo (JP)

( * ) Notice: Subject to any disclaimer, the term of this patent is extended or adjusted under 35 U.S.C. 154(b) by 365 days.

This patent is subject to a terminal disclaimer.

(21) Appl. No.: 12/445,050

(22) PCT Filed: Oct. 11, 2007

(86) PCT No.: PCT/JP2007/070309
§ 371 (c)(1),
(2), (4) Date: Apr. 9, 2009

(87) PCT Pub. No.: WO2008/044797
PCT Pub. Date: Apr. 17, 2008

(65) Prior Publication Data
US 2010/0086489 A1    Apr. 8, 2010

Related U.S. Application Data

(63) Continuation-in-part of application No. PCT/JP2007/063871, filed on Jul. 5, 2007.

(30) Foreign Application Priority Data

Oct. 11, 2006  (JP) ................................ 2006-278029
Mar. 30, 2007  (JP) ................................ 2007-095017

(51) Int. Cl.
*A61K 38/00* (2006.01)
(52) U.S. Cl. ................ 514/16.7; 514/1.1; 514/16.9
(58) Field of Classification Search .............. 514/1.1, 514/16.7, 16.9
See application file for complete search history.

(56) References Cited

U.S. PATENT DOCUMENTS
2003/0013651 A1   1/2003   Lam et al.

FOREIGN PATENT DOCUMENTS
JP   2004-526748   9/2004
WO   02/080955    10/2002

OTHER PUBLICATIONS

Definition "osteopenia" in online printout from www.dictionary.reference.com/browse/osteopenia. pp. 1-2, 2011.*
Tomimori, et al., "42: Production of Osteopenia models by GST-RANKL administration", The 8th Annual Meeting of Japan Osteoporosis Society, Osteoporosis Japan, vol. 14, suppl. 1, vol. 57, 2006, p. 139 (with an English translation).
Yasuda, "Special article: Molecular approach to osteoporosis treatment RANKL-RANK-ORG", Journal of Osteoporotic Medicine, vol. 3, No. 4, 2004, pp. 16-21 (with an English translation).
Thompson, et al., "FDA Guidelines and Animal Models for Osteoporosis", Bone, vol. 17, No. 4, Supplement, Oct. 1995, pp. 125S-133S.
Sato, "Osteoclast-activating factors (OAF) "RANKL and other factors"", Japanese Journal of Clinical Medicine, vol. 62, No. 860, pp. 228-231 (with an English translation), 2004.
Juji, "Special article: Recent bone formation/bone resorption topic III", The Bone, vol. 17, No. 5, 2003, pp. 81-83 (with an English translation).
Mizuno, et al., "Transgenic mice overexpressing soluble osteoclast differentiation factor (sODF) exhibit severe osteoporosis", J Bone Miner Metab., vol. 20, 2002, pp. 337-344.
Kishimoto, et al., "Promotion of RANKL activity upon fusion of RANKL wth GST", The 24th Annual Meeting of the Japanese Society for Bone and Mineral Research, Program & Abstracts, Jul. 2006, Abstract P2-12, p. 252 (with an English translation).
Mitlak, et al., "Selective Estrogen Receptor Modulators", Drugs, vol. 57, No. 5, May 1999, pp. 653-663.
Wada, et al., "The molecular scaffold Gab2 is a crucial component of RANK signaling and osteoclastogenesis", Nature Medicine, vol. 11, No. 4, Apr. 2005, pp. 394-399.
Wittrant, et al., "RANKL/RANK/OPG: new therapeutic targets in bone tumours and associated osteolysis", Biochim.Biophys.Acta, vol. 1704, 2004, pp. 49-57.
Yasuda et al., "Osteoclast differentiation factor is a ligand for osteoprotegerin/osteoclastogenesis-inhibitory factor and is identical to TRANCE/RANKL", Proc. Natl. Acad. Sci. USA, vol. 95, Mar. 1998, pp. 3597-3602.
Lacey et al., "Osteoprotegerin ligand is a cytokine that regulates osteoclast differentiation and activation", Cell, vol. 93, Apr. 17, 1998, pp. 165-176.
Wronski et al., "Temporal relationship between bone loss and increased bone turnover in ovariectomized rats", Calcified Tissue International, vol. 43, No. 3, Sep. 1988, pp. 179-183.
Wronksi et al., "Estrogen treatment prevents osteopenia and depresses bone turnover in ovariectomized rats", Endocrinology, vol. 123, No. 2, Aug. 1988, pp. 681-686.
Wronski et al., "Long-term effects of ovariectomy and aging on the rat skeleton", Calcified Tissue International, vol. 45, No. 6, Dec. 1989, pp. 360-366.
De Winter et al., "The effect of a low-calcium diet in lactating rats; observation on the rapid development and repair of osteoporosis", Calcified Tissue Research, vol. 17, No. 4, 1975, pp. 303-316.
Geusens et al., "Calcium-deficient diet in ovariectomized dogs limits the effects of 17β-estradiol and nandrolone decanoate on bone", Journal of Bone and Mineral Research, vol. 6, No. 8, Aug. 1991, pp. 791-797.
Wakley et al., "The effects of tamoxifen on the osteopenia induced by sciatic neurotomy in the rat: a histomorphometric study", Calcified Tissue International, vol. 43, No. 6, Dec. 1988, pp. 383-388.

(Continued)

*Primary Examiner* — Marcia S Noble
(74) *Attorney, Agent, or Firm* — Hamre, Schumann, Mueller & Larson, P.C.

(57) ABSTRACT

The present invention provides a method for producing an osteopenia animal model by RANKL administration and an osteopenia animal model.
Also, a method for producing an osteopenia animal model, comprising administering soluble RANKL or a fused protein of soluble RANKL with an epitope tag to a non-human animal so as to promote vivo osteoclast differentiation and activation in the non-human animal, and an osteopenia animal model produced by the method are provided.

10 Claims, 91 Drawing Sheets
(4 of 91 Drawing Sheet(s) Filed in Color)

OTHER PUBLICATIONS

Globus et al., "Skeletal response to dietary calcium in a rat model simulating weightlessness", Journal of Bone and Mineral Research, vol. 1, No. 2, Apr. 1986, pp. 191-197.

Hofbauer et al., "Receptor activator of nuclear factor—kappa B ligand and osteoprotegerin. Potential implications for the pathogenesis and treatment of malignant bone diseases," Cancer, 2001, vol. 92, No. 3, pp. 460-470.

Maruyama et al., "Receptor activator of NF-kappa B ligand and osteoprotegerin regulate proinflammatory cytokine production in mice," Journal of Immunology, 2006, vol. 177, No. 6, pp. 3799-3805.

Frew et al., "Osteopenia in Siahla mutant mice," Journal of Biological Chemistry, 2004, vol. 279, No. 28, pp. 29583-29588.

Ihara et al., "Osteopontin-deficiency suppresses PTH/RANKL-induced bone resorption in organ cultures," Journal of Bone and Mineral Research, 2000, vol. 15, No. suppl. 1, XP-002961016.

Woo et al., "Quercetin suppresses bone resorption by inhibiting the differentiation and activation of osteoclasts," Biological & Pharmaceutical Bulletin, 2004, vol. 27, No. 4, pp. 504-509.

Sattler et al., "Novel aspects on RANK ligand and osteoprotegerin in osteoporosis and vascular disease," Calified Tissue International, 2004, vol. 74, No. 1, pp. 103-106.

Franchimont et al., "Increased expression of receptor activator of NF-kappaB ligand (RANKL), its receptor RANK and its decoy receptor osteoprotegerin in the colon of Crohn's disease patients," Clinical and Experimental Immunology, 2004, vol. 138, No. 3, pp. 491-498.

Moschen et al., "The RANKL/OPG system and bone mineral density in patients with chronic liver disease," Journal of Hepatology, 2005, vol. 43, No. 6, pp. 973-983.

Miyazaki et al., "Changes in receptor activator of nuclear factor-kappaβ, and its ligand, osteoprotegerin, bone-type alkaline phosphatase, and tartrate-resistant acid phosphatase in ovariectomized rats," Journal of Cellular Biochemistry, 2004, vol. 93, pp. 503-512.

* cited by examiner

*: Significance test for comparison with Control
(ANOVA → multiple comparison with control group (Dunnett method)), $P < 0.01$ † Significance test for comparison with 0-nmol dose group
(ANOVA → multiple comparison with control group (Dunnett method)), $P < 0.01$

*: Significance test for comparison with group treated with GST-LANKL alone
(ANOVA → multiple comparison with control group (Dunnett method)), $P < 0.05$
†: Significance test for comparison with group treated with GST-LANKL alone
(ANOVA → multiple comparison with control group (Dunnett method)), $P < 0.01$ \*: Significance test for comparison with Control
(ANOVA → multiple comparison with control group (Dunnett method)), $P < 0.05$;
†: Significance test for comparison with Control
(ANOVA → multiple comparison with control group (Dunnett method)), $P < 0.01$ Fig. 54
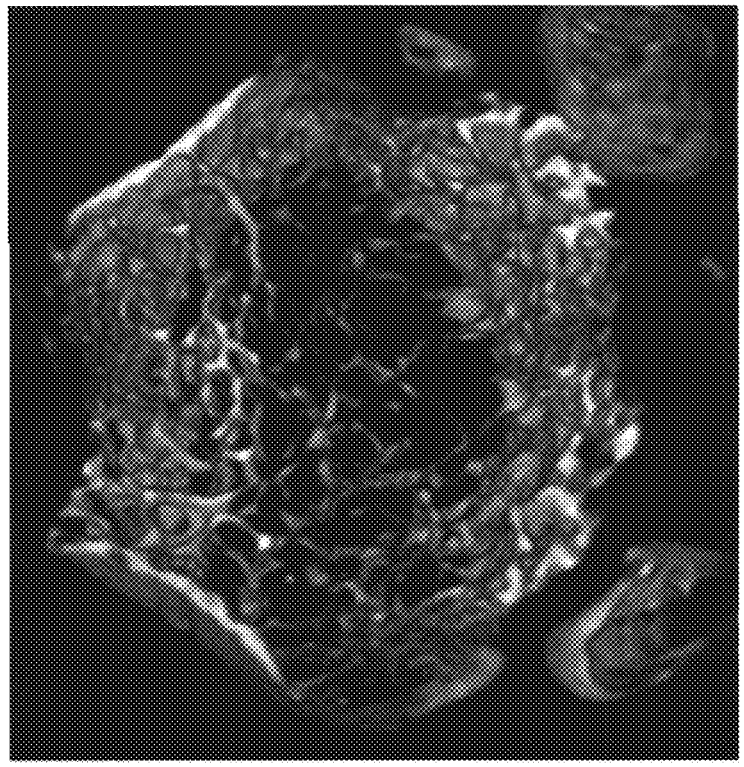
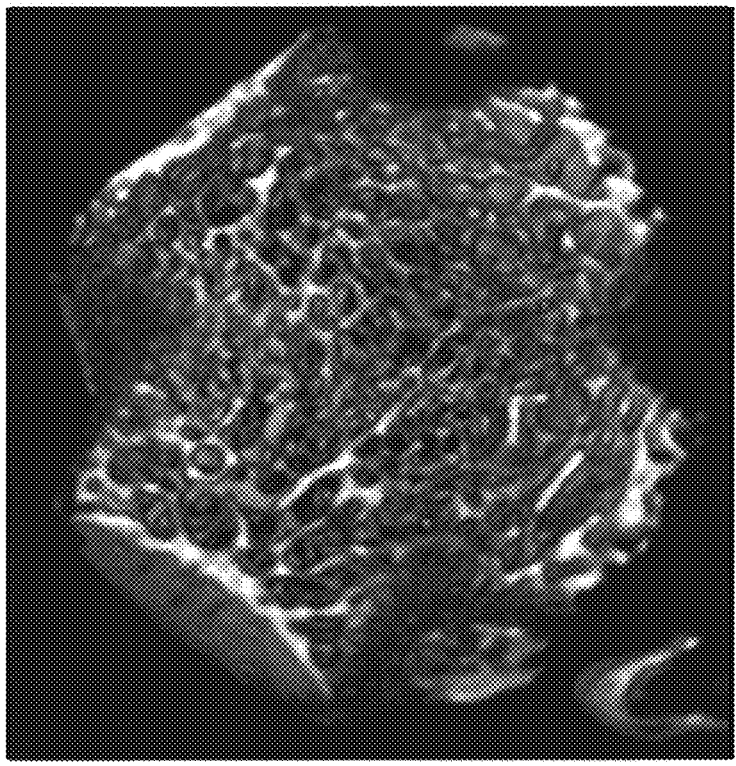

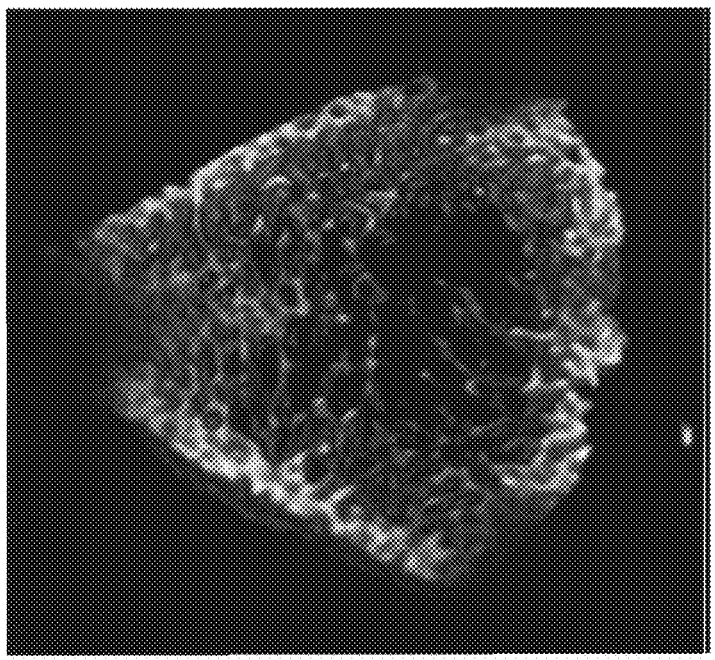
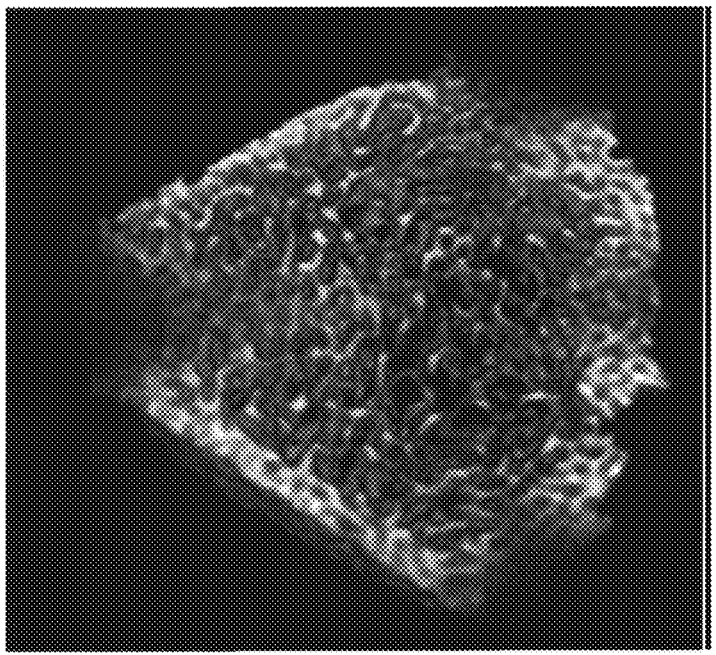
Fig. 60

Fig. 67
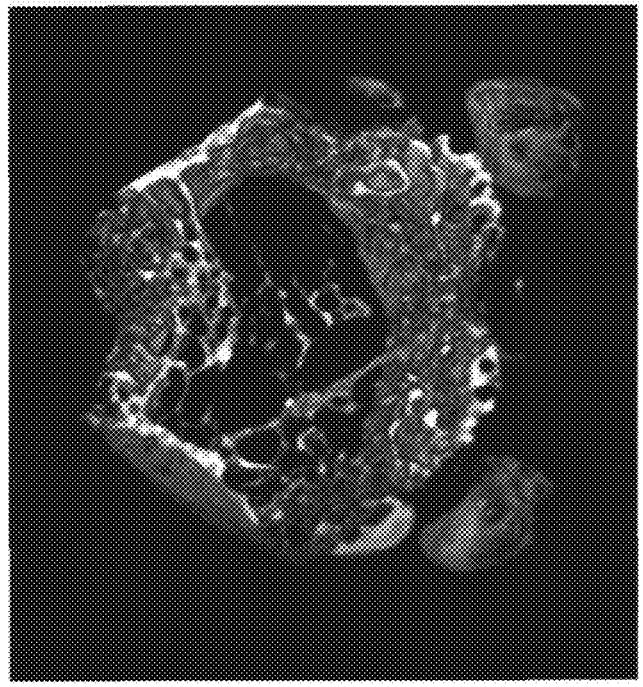
GST-RANKL
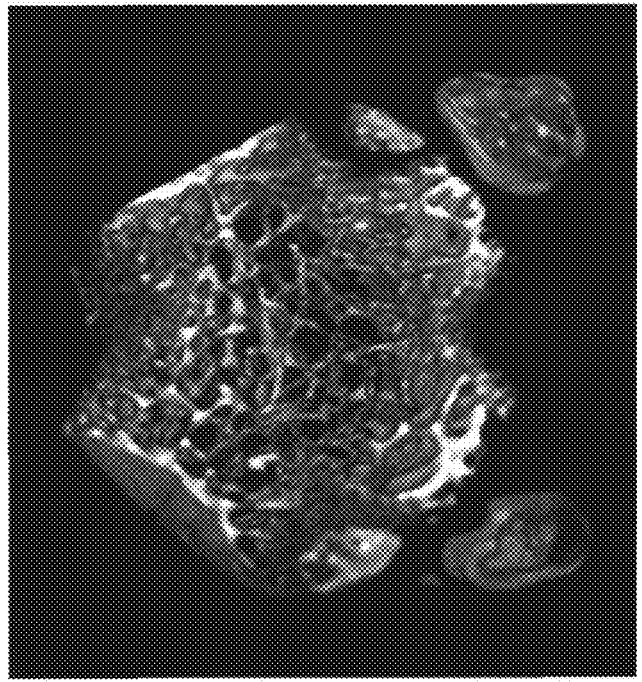
PBS

**: Significance test for comparison with group treated with RANKL, p < 0.01

*: Significance test for comparison with group treated with RANKL, $p < 0.05$

**: Significance test for comparison with group treated with RANKL, p < 0.01

**: Significance test for comparison with group treated with RANKL, p < 0.01

*: Significance test for comparison with group treated with RANKL, p < 0.05

```
                            SEQUENCE LISTING

<160> NUMBER OF SEQ ID NOS: 24

<210> SEQ ID NO 1
<211> LENGTH: 2201
<212> TYPE: DNA
<213> ORGANISM: Homo sapiens
<220> FEATURE:
<221> NAME/KEY: CDS
<222> LOCATION: (129)..(1082)

<400> SEQUENCE: 1
ggccaaagcc gggctccaag tcggcgcccc acgtcgaggc tccgccgcag cctccggagt      60
tggccgcaga caagaagggg agggagcggg agagggagga gagctccgaa gcgagagggc     120 cgagcgcc atg cgc cgc gcc agc aga gac tac acc aag tac ctg cgt ggc     170
         Met Arg Arg Ala Ser Arg Asp Tyr Thr Lys Tyr Leu Arg Gly
          1               5                  10 tcg gag gag atg ggc ggc ggc ccc gga gcc ccg cac gag ggc ccc ctg       218
Ser Glu Glu Met Gly Gly Gly Pro Gly Ala Pro His Glu Gly Pro Leu
 15              20                  25                  30 cac gcc ccg ccg ccg cct gcg ccg cac cag ccc ccc gcc gcc tcc cgc       266
His Ala Pro Pro Pro Pro Ala Pro His Gln Pro Pro Ala Ala Ser Arg
                 35                  40                  45 tcc atg ttc gtg gcc ctc ctg ggg ctg ggg ctg ggc cag gtt gtc tgc       314
Ser Met Phe Val Ala Leu Leu Gly Leu Gly Leu Gly Gln Val Val Cys
             50                  55                  60 agc gtc gcc ctg ttc ttc tat ttc aga gcg cag atg gat cct aat aga       362
Ser Val Ala Leu Phe Phe Tyr Phe Arg Ala Gln Met Asp Pro Asn Arg
         65                  70                  75 ata tca gaa gat ggc act cac tgc att tat aga att ttg aga ctc cat       410
Ile Ser Glu Asp Gly Thr His Cys Ile Tyr Arg Ile Leu Arg Leu His
     80                  85                  90 gaa aat gca gat ttt caa gac aca act ctg gag agt caa gat aca aaa       458
Glu Asn Ala Asp Phe Gln Asp Thr Thr Leu Glu Ser Gln Asp Thr Lys
 95                 100                 105                 110 tta ata cct gat tca tgt agg aga att aaa cag gcc ttt caa gga gct       506
Leu Ile Pro Asp Ser Cys Arg Arg Ile Lys Gln Ala Phe Gln Gly Ala
                115                 120                 125 gtg caa aag gaa tta caa cat atc gtt gga tca cag cac atc aga gca       554
Val Gln Lys Glu Leu Gln His Ile Val Gly Ser Gln His Ile Arg Ala
            130                 135                 140
```

-continued

| | |
|---|---|
| gag aaa gcg atg gtg gat ggc tca tgg tta gat ctg gcc aag agg agc<br>Glu Lys Ala Met Val Asp Gly Ser Trp Leu Asp Leu Ala Lys Arg Ser<br>     145                      150                     155 | 602 |
| aag ctt gaa gct cag cct ttt gct cat ctc act att aat gcc acc gac<br>Lys Leu Glu Ala Gln Pro Phe Ala His Leu Thr Ile Asn Ala Thr Asp<br>160                        165                     170 | 650 |
| atc cca tct ggt tcc cat aaa gtg agt ctg tcc tct tgg tac cat gat<br>Ile Pro Ser Gly Ser His Lys Val Ser Leu Ser Ser Trp Tyr His Asp<br>175                      180                    185                   190 | 698 |
| cgg ggt tgg gcc aag atc tcc aac atg act ttt agc aat gga aaa cta<br>Arg Gly Trp Ala Lys Ile Ser Asn Met Thr Phe Ser Asn Gly Lys Leu<br>                  195                    200                    205 | 746 |
| ata gtt aat cag gat ggc ttt tat tac ctg tat gcc aac att tgc ttt<br>Ile Val Asn Gln Asp Gly Phe Tyr Tyr Leu Tyr Ala Asn Ile Cys Phe<br>               210                     215                    220 | 794 |
| cga cat cat gaa act tca gga gac cta gct aca gag tat ctt caa cta<br>Arg His His Glu Thr Ser Gly Asp Leu Ala Thr Glu Tyr Leu Gln Leu<br>225                        230                    235 | 842 |
| atg gtg tac gtc act aaa acc agc atc aaa atc cca agt tct cat acc<br>Met Val Tyr Val Thr Lys Thr Ser Ile Lys Ile Pro Ser Ser His Thr<br>240                        245                    250 | 890 |
| ctg atg aaa gga gga agc acc aag tat tgg tca ggg aat tct gaa ttc<br>Leu Met Lys Gly Gly Ser Thr Lys Tyr Trp Ser Gly Asn Ser Glu Phe<br>255                        260                    265                   270 | 938 |
| cat ttt tat tcc ata aac gtt ggt gga ttt ttt aag tta cgg tct gga<br>His Phe Tyr Ser Ile Asn Val Gly Gly Phe Phe Lys Leu Arg Ser Gly<br>                  275                    280                    285 | 986 |
| gag gaa atc agc atc gag gtc tcc aac ccc tcc tta ctg gat ccg gat<br>Glu Glu Ile Ser Ile Glu Val Ser Asn Pro Ser Leu Leu Asp Pro Asp<br>               290                     295                    300 | 1034 |
| cag gat gca aca tac ttt ggg gct ttt aaa gtt cga gat ata gat tga<br>Gln Asp Ala Thr Tyr Phe Gly Ala Phe Lys Val Arg Asp Ile Asp<br>305                        310                    315 | 1082 |
| gccccagttt ttggagtgtt atgtatttcc tggatgtttg gaaacatttt ttaaaacaag | 1142 |
| ccaagaaaga tgtatatagg tgtgtgagac tactaagagg catggcccca acggtacacg | 1202 |
| actcagtatc catgctcttg accttgtaga gaacacgcgt atttacctgc cagtgggaga | 1262 |
| tgttagactc atggtgtgtt acacaatggt ttttaaattt tgtaatgaat tcctagaatt | 1322 |
| aaaccagatt ggagcaatta cgggttgacc ttatgagaaa ctgcatgtgg gctatgggag | 1382 |
| gggttggtcc ctggtcatgt gcccttcgc agctgaagtg gagagggtgt catctagcgc | 1442 |
| aattgaagga tcatctgaag gggcaaattc ttttgaattg ttacatcatg ctggaacctg | 1502 |
| caaaaaatac ttttctaat gaggagagaa aatatatgta ttttatata atatctaaag | 1562 |
| ttatatttca gatgtaatgt tttctttgca agtattgta aattatattt gtgctatagt | 1622 |
| atttgattca aaatatttaa aaatgtcttg ctgttgacat atttaatgtt ttaaatgtac | 1682 |
| agacatattt aactggtgca ctttgtaaat tccctgggga aaacttgcag ctaaggaggg | 1742 |
| gaaaaaaatg ttgtttccta atatcaaatg cagtatattt cttcgttctt tttaagttaa | 1802 |
| tagatttttt cagacttgtc aagcctgtgc aaaaaaatta aatgggatgc cttgaataat | 1862 |
| aagcaggatg ttggccacca ggtgcctttc aaatttagaa actaattgac tttagaaagc | 1922 |
| tgacattgcc aaaaaggata cataatgggc cactgaaatt tgtcaagagt agttatataa | 1982 |
| ttgttgaaca ggtgtttttc cacaagtgcc gcaaattgta ccttttttt ttttcaaaa | 2042 |
| tagaaaagtt attagtggtt tatcagcaaa aaagtccaat tttaatttag taaatgttat | 2102 |
| tttatactgt acaataaaaa cattgccttt gaatgttaat ttttggtac aaaaataaat | 2162 | ttatatgaaa aaaaaaaaaa aaaaaaaaaa aaaaaaaaa                    2201

<210> SEQ ID NO 2
<211> LENGTH: 317
<212> TYPE: PRT
<213> ORGANISM: Homo sapiens

<400> SEQUENCE: 2

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65              70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145             150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225             230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
    290                 295                 300

Ala Thr Tyr Phe Gly Ala Phe Lys Val Arg Asp Ile Asp
305                 310                 315

<210> SEQ ID NO 3
<211> LENGTH: 8
<212> TYPE: PRT
<213> ORGANISM: Artificial
<220> FEATURE:
<223> OTHER INFORMATION: Synthetic

<400> SEQUENCE: 3

```
Asp Tyr Lys Asp Asp Asp Asp Lys
1               5

<210> SEQ ID NO 4
<211> LENGTH: 10
<212> TYPE: PRT
<213> ORGANISM: Artificial
<220> FEATURE:
<223> OTHER INFORMATION: Synthetic

<400> SEQUENCE: 4

Glu Gln Lys Leu Ile Ser Glu Glu Asp Leu
1               5                   10

<210> SEQ ID NO 5
<211> LENGTH: 14
<212> TYPE: PRT
<213> ORGANISM: Artificial
<220> FEATURE:
<223> OTHER INFORMATION: Synthetic

<400> SEQUENCE: 5

Gly Lys Pro Ile Pro Asn Pro Leu Leu Gly Leu Asp Ser Thr
1               5                   10

<210> SEQ ID NO 6
<211> LENGTH: 6
<212> TYPE: PRT
<213> ORGANISM: Artificial
<220> FEATURE:
<223> OTHER INFORMATION: Synthetic

<400> SEQUENCE: 6

His Gln His Gln His Gln
1               5

<210> SEQ ID NO 7
<211> LENGTH: 9
<212> TYPE: PRT
<213> ORGANISM: Artificial
<220> FEATURE:
<223> OTHER INFORMATION: Synthetic

<400> SEQUENCE: 7

Tyr Pro Tyr Asp Val Pro Asp Tyr Ala
1               5

<210> SEQ ID NO 8
<211> LENGTH: 6
<212> TYPE: PRT
<213> ORGANISM: Artificial
<220> FEATURE:
<223> OTHER INFORMATION: Synthetic

<400> SEQUENCE: 8

Asp Thr Tyr Arg Tyr Ile
1               5

<210> SEQ ID NO 9
<211> LENGTH: 11
<212> TYPE: PRT
<213> ORGANISM: Artificial
<220> FEATURE:
<223> OTHER INFORMATION: Synthetic

<400> SEQUENCE: 9

Met Ala Ser Met Thr Gly Gly Gln Gln Met Gly
1               5                   10
```

```
<210> SEQ ID NO 10
<211> LENGTH: 11
<212> TYPE: PRT
<213> ORGANISM: Artificial
<220> FEATURE:
<223> OTHER INFORMATION: Synthetic

<400> SEQUENCE: 10

Tyr Thr Asp Ile Glu Met Asn Arg Leu Gly Lys
1               5                   10

<210> SEQ ID NO 11
<211> LENGTH: 5
<212> TYPE: PRT
<213> ORGANISM: Artificial
<220> FEATURE:
<223> OTHER INFORMATION: Synthetic

<400> SEQUENCE: 11

Asp Asp Asp Asp Lys
1               5

<210> SEQ ID NO 12
<211> LENGTH: 16
<212> TYPE: PRT
<213> ORGANISM: Artificial
<220> FEATURE:
<223> OTHER INFORMATION: Synthetic

<400> SEQUENCE: 12

Lys Glu Thr Ala Ala Ala Lys Phe Glu Arg Gln His Ile Asp Ser Cys
1               5                   10                  15

<210> SEQ ID NO 13
<211> LENGTH: 12
<212> TYPE: PRT
<213> ORGANISM: Artificial
<220> FEATURE:
<223> OTHER INFORMATION: Synthetic

<400> SEQUENCE: 13

Met Lys Ala Glu Phe Arg Arg Gln Glu Ser Asp Arg
1               5                   10

<210> SEQ ID NO 14
<211> LENGTH: 12
<212> TYPE: PRT
<213> ORGANISM: Artificial
<220> FEATURE:
<223> OTHER INFORMATION: Synthetic

<400> SEQUENCE: 14

Met Arg Asp Ala Leu Asp Arg Leu Asp Arg Leu Ala
1               5                   10

<210> SEQ ID NO 15
<211> LENGTH: 12
<212> TYPE: PRT
<213> ORGANISM: Artificial
<220> FEATURE:
<223> OTHER INFORMATION: Synthetic

<400> SEQUENCE: 15

Met Lys Asp Gly Glu Glu Tyr Ser Arg Ala Phe Arg
1               5                   10
```

-continued

```
<210> SEQ ID NO 16
<211> LENGTH: 9
<212> TYPE: PRT
<213> ORGANISM: Artificial
<220> FEATURE:
<223> OTHER INFORMATION: Synthetic

<400> SEQUENCE: 16

Glu Glu Glu Glu Tyr Met Pro Met Glu
1               5

<210> SEQ ID NO 17
<211> LENGTH: 12
<212> TYPE: PRT
<213> ORGANISM: Artificial
<220> FEATURE:
<223> OTHER INFORMATION: Synthetic

<400> SEQUENCE: 17

Cys Thr Pro Thr Asp Val Pro Asp Tyr Ala Ser Leu
1               5                   10

<210> SEQ ID NO 18
<211> LENGTH: 6
<212> TYPE: PRT
<213> ORGANISM: Artificial
<220> FEATURE:
<223> OTHER INFORMATION: Synthetic

<400> SEQUENCE: 18

Pro Pro Glu Pro Glu Thr
1               5

<210> SEQ ID NO 19
<211> LENGTH: 1275
<212> TYPE: DNA
<213> ORGANISM: Artificial
<220> FEATURE:
<223> OTHER INFORMATION: GST-RANKL (aa127-317)

<400> SEQUENCE: 19
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acgtgtttc gagaattgca tatagtaaag actttgaaac tctcaaagtt      360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca      600 tggcctttgc agggctggca agccacgttt ggtggtggcg accatcctcc aaaatcggat     660
ctggttccgc gtggatcccc aggaattccc gggtcgactg tgcaaaagga attacaacat     720
atcgttggat cacagcacat cagagcagag aaagcgatgg tggatggctc atggttagat     780
ctggccaaga ggagcaagct tgaagctcag ccttttgctc atctcactat taatgccacc     840
gacatcccat ctggttccca taagtgagt ctgtcctctt ggtaccatga tcggggttgg     900
gccaagatct ccaacatgac ttttagcaat ggaaaactaa tagttaatca ggatggcttt     960
```

-continued

```
tattacctgt atgccaacat ttgctttcga catcatgaaa cttcaggaga cctagctaca    1020
gagtatcttc aactaatggt gtacgtcact aaaaccagca tcaaaatccc aagttctcat    1080
accctgatga aggaggaag caccaagtat tggtcaggga attctgaatt ccatttttat     1140
tccataaacg ttggtggatt ttttaagtta cggtctggag aggaaatcag catcgaggtc    1200 tccaaccct ccttactgga tccggatcag gatgcaacat actttggggc ttttaaagtt     1260
cgagatatag attga                                                     1275
```

<210> SEQ ID NO 20
<211> LENGTH: 442
<212> TYPE: PRT
<213> ORGANISM: Artificial
<220> FEATURE:
<223> OTHER INFORMATION: GST-RANKL (aa127-317)

<400> SEQUENCE: 20

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ser Leu Val
225                 230                 235                 240

Pro Arg Gly Ser Pro Gly Ile Pro Gly Ser Thr Val Gln Lys Glu Leu
                245                 250                 255

Gln His Ile Val Gly Ser Gln His Ile Arg Ala Glu Lys Ala Met Val
            260                 265                 270

Asp Gly Ser Trp Leu Asp Leu Ala Lys Arg Ser Lys Leu Glu Ala Gln
        275                 280                 285

Pro Phe Ala His Leu Thr Ile Asn Ala Thr Asp Ile Pro Ser Gly Ser
    290                 295                 300

His Lys Val Ser Leu Ser Ser Trp Tyr His Asp Arg Gly Trp Ala Lys
```

```
                305                 310                 315                 320
            Ile Ser Asn Met Thr Phe Ser Asn Gly Lys Leu Ile Val Asn Gln Asp
                            325                 330                 335

Gly Phe Tyr Tyr Leu Tyr Ala Asn Ile Cys Phe Arg His His Glu Thr
                            340                 345                 350

Ser Gly Asp Leu Ala Thr Glu Tyr Leu Gln Leu Met Val Tyr Val Thr
                            355                 360                 365

Lys Thr Ser Ile Lys Ile Pro Ser Ser His Thr Leu Met Lys Gly Gly
                            370                 375                 380

Ser Thr Lys Tyr Trp Ser Gly Asn Ser Glu Phe His Phe Tyr Ser Ile
            385                 390                 395                 400

Asn Val Gly Gly Phe Phe Lys Leu Arg Ser Gly Glu Glu Ile Ser Ile
                            405                 410                 415

Glu Val Ser Asn Pro Ser Leu Leu Asp Pro Asp Gln Asp Ala Thr Tyr
                            420                 425                 430

Phe Gly Ala Phe Lys Val Arg Asp Ile Asp
                            435                 440

<210> SEQ ID NO 21
<211> LENGTH: 1236
<212> TYPE: DNA
<213> ORGANISM: Artificial
<220> FEATURE:
<223> OTHER INFORMATION: GST-RANKL (aa140-317)

<400> SEQUENCE: 21 atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acgtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggttccgc gtggatcccc aggaattccc gggtcgacta tcagagcaga gaaagcgatg    720
gtggatggct catggttaga tctggccaag aggagcaagc ttgaagctca gccttttgct    780
catctcacta ttaatgccac cgacatccca tctggttccc ataaagtgag tctgtcctct    840
tggtaccatg atcggggttg ggccaagatc tccaacatga cttttagcaa tggaaaacta    900
atagttaatc aggatggctt ttattacctg tatgccaaca tttgctttcg acatcatgaa    960
acttcaggag acctagctac agagtatctt caactaatgg tgtacgtcac taaaaccagc   1020
atcaaaatcc caagttctca taccctgatg aaaggaggaa gcaccaagta ttggtcaggg   1080
aattctgaat ccatttttta ttccataaac gttggtggat ttttttaagtt acggtctgga   1140 gaggaaatca gcatcgaggt ctccaacccc tccttactgg atccggatca ggatgcaaca   1200
tactttgggg cttttaaagt tcgagatata gattga                             1236

<210> SEQ ID NO 22
```

<211> LENGTH: 429
<212> TYPE: PRT
<213> ORGANISM: Artificial
<220> FEATURE:
<223> OTHER INFORMATION: GST-RANKL (aa140-317)

<400> SEQUENCE: 22

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Leu Val
225                 230                 235                 240

Pro Arg Gly Ser Pro Gly Ile Pro Gly Ser Thr Ile Arg Ala Glu Lys
                245                 250                 255

Ala Met Val Asp Gly Ser Trp Leu Asp Leu Ala Lys Arg Ser Lys Leu
            260                 265                 270

Glu Ala Gln Pro Phe Ala His Leu Thr Ile Asn Ala Thr Asp Ile Pro
        275                 280                 285

Ser Gly Ser His Lys Val Ser Leu Ser Ser Trp Tyr His Asp Arg Gly
    290                 295                 300

Trp Ala Lys Ile Ser Asn Met Thr Phe Ser Asn Gly Lys Leu Ile Val
305                 310                 315                 320

Asn Gln Asp Gly Phe Tyr Tyr Leu Tyr Ala Asn Ile Cys Phe Arg His
                325                 330                 335

His Glu Thr Ser Gly Asp Leu Ala Thr Glu Tyr Leu Gln Leu Met Val
            340                 345                 350

Tyr Val Thr Lys Thr Ser Ile Lys Ile Pro Ser Ser His Thr Leu Met
        355                 360                 365

Lys Gly Gly Ser Thr Lys Tyr Trp Ser Gly Asn Ser Glu Phe His Phe
    370                 375                 380
```

```
Tyr Ser Ile Asn Val Gly Gly Phe Phe Lys Leu Arg Ser Gly Glu Glu
385                 390                 395                 400

Ile Ser Ile Glu Val Ser Asn Pro Ser Leu Leu Asp Pro Asp Gln Asp
                405                 410                 415

Ala Thr Tyr Phe Gly Ala Phe Lys Val Arg Asp Ile Asp
            420                 425
```

<210> SEQ ID NO 23
<211> LENGTH: 1179
<212> TYPE: DNA
<213> ORGANISM: Artificial
<220> FEATURE:
<223> OTHER INFORMATION: GST-RANKL (aa159-317)

<400> SEQUENCE: 23

```
atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg agtttcccca tcttcctta ttatattgat     180
ggtgatgtta aattaacaca gtctatggcc atcatacgtt atatagctga caagcacaac    240
atgttgggtg ttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg atgcgttcc caaaattagt ttgttttaaa     540
aaacgtattg aagctatccc acaaattgat aagtacttga atccagcaa gtatatagca    600
tggcctttgc agggctggca agccacgttt ggtggtggcg accatcctcc aaaatcggat    660
ctggttccgc gtggatcccc aggaattccc gggtcgacta gcttgaagc tcagcctttt    720
gctcatctca ctattaatgc caccgacatc ccatctggtt cccataaagt gagtctgtcc    780
tcttggtacc atgatcgggg ttgggccaag atctccaaca tgactttag caatggaaaa    840
ctaatagtta tcaggatgg cttttattac ctgtatgcca catttgctt tcgacatcat     900
gaaacttcag agacctagc tacagagtat cttcaactaa tggtgtacgt cactaaaacc    960
agcatcaaaa tcccaagttc tcatacccctg atgaaaggag gaagcaccaa gtattggtca   1020
gggaattctg aattccattt ttattccata aacgttggtg gatttttaa gttacggtct   1080
ggagaggaaa tcagcatcga ggtctccaac ccctccttac tggatccgga tcaggatgca   1140
acatactttg gggcttttaa agttcgagat atagattga                          1179
```

<210> SEQ ID NO 24
<211> LENGTH: 410
<212> TYPE: PRT
<213> ORGANISM: Artificial
<220> FEATURE:
<223> OTHER INFORMATION: GST-RANKL (aa159-317)

<400> SEQUENCE: 24

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60
```

-continued

```
Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Leu Val Pro Arg
        210                 215                 220

Gly Ser Pro Gly Ile Pro Gly Ser Thr Arg Ala Ala Ser Leu Val
225                 230                 235                 240

Pro Arg Gly Ser Pro Gly Ile Pro Gly Ser Thr Lys Leu Glu Ala Gln
                245                 250                 255

Pro Phe Ala His Leu Thr Ile Asn Ala Thr Asp Ile Pro Ser Gly Ser
            260                 265                 270

His Lys Val Ser Leu Ser Ser Trp Tyr His Asp Arg Gly Trp Ala Lys
            275                 280                 285

Ile Ser Asn Met Thr Phe Ser Asn Gly Lys Leu Ile Val Asn Gln Asp
290                 295                 300

Gly Phe Tyr Tyr Leu Tyr Ala Asn Ile Cys Phe Arg His His Glu Thr
305                 310                 315                 320

Ser Gly Asp Leu Ala Thr Glu Tyr Leu Gln Leu Met Val Tyr Val Thr
                325                 330                 335

Lys Thr Ser Ile Lys Ile Pro Ser Ser His Thr Leu Met Lys Gly Gly
            340                 345                 350

Ser Thr Lys Tyr Trp Ser Gly Asn Ser Glu Phe His Phe Tyr Ser Ile
        355                 360                 365

Asn Val Gly Gly Phe Phe Lys Leu Arg Ser Gly Glu Glu Ile Ser Ile
370                 375                 380

Glu Val Ser Asn Pro Ser Leu Leu Asp Pro Asp Gln Asp Ala Thr Tyr
385                 390                 395                 400

Phe Gly Ala Phe Lys Val Arg Asp Ile Asp
                405                 410
```

OSTEOPENIA ANIMAL MODEL

TECHNICAL FIELD

The present invention relates to an osteopenia animal model with a lower bone mass than normal animals.

BACKGROUND ART

Osteoclasts, which control osteolysis, are large multinucleated cells derived from hematopoietic cells that differentiate into monocytes/macrophages. Differentiation and maturation of osteoclast precursor cells into osteoclasts are controlled by osteoblasts/stromal cells on the bone surface area. An osteoclast differentiation factor (RANKL; receptor activator of NF-κB ligand) is a membrane-bound protein belonging to the family of tumor necrosis factors (TNFs) guided by bone resorption factors onto osteoblasts/stromal cells, and it is essential for osteoclast differentiation/maturation (see Non-Patent Documents 1 and 2). It has been known that RANKL is partially cleaved by metalloprotease in an extracellular region so as to result in soluble RANKL. In practice, soluble RANKL is known to induce in vitro differentiation of macrophage precursor cells such as myelocytes, spleen cells, precursor cells in the peripheral blood, cells of a macrophage cell line, and the like into osteoclasts when coexisting with M-CSF.

Meanwhile, conventional osteopenia models have been prepared by methods involving ovariectomy (see Non-Patent Documents 3 to 6), low-calcium diet (see Non-Patent Documents 7 and 8), neurectomy (see Non-Patent Document 9), immobilization via hindlimb suspension (see Non-Patent Document 10), and the like. In any case, it takes approximately 1 to 4 weeks to cause development of osteopenia. Therefore, it has been time-consuming to evaluate drugs such as bone resorption suppressants (e.g., bisphosphonate and Cathepsin K inhibitors) and osteogenesis promoters (e.g., parathyroid hormone (PTH)). In addition, in the above animal models, osteoclast activation is indirectly induced by estrogen depletion, an increase in PTH, and the like. Therefore, it has been difficult to demonstrate in which phase of osteopenia a drug can be evaluated as being effective in vivo.

Non-Patent Document 1: Yasuda et al., Proc Natl Acad Sci USA 95: 3597, 1998
Non-Patent Document 2: Lacey et al., Cell 93: 165, 1998
Non-Patent Document 3: Thompson et al., Bone 17(Suppl.): S125, 1995
Non-Patent Document 4: Wronski et al., Calcif Tissue Int 42: 179, 1988
Non-Patent Document 5: Wronski et al., Endocrinology 123: 681, 1988
Non-Patent Document 6: Wronski et al., Calcif Tissue Int 45: 360, 1989
Non-Patent Document 7: de Winter et al., Calcif Tissue Res 17: 303, 1975
Non-Patent Document 8: Geusens et al., J Bone Miner Res 6: 791, 1991
Non-Patent Document 9: Wakley et al., Calcif Tissue Int 43, 383, 1988
Non-Patent Document 10: Globus et al., J Bone Miner Res 1: 191, 1986

DISCLOSURE OF THE INVENTION

It is an object of the present invention to provide a method for producing an osteopenia animal model by RANKL administration and to provide an osteopenia animal model.

The present inventors intensively studied a method for producing an osteopenia animal model whereby problems of conventional osteopenia animal models can be resolved. As a result, they have found that an osteopenia animal model can be produced by administering soluble RANKL or a fused protein of soluble RANKL with an epitope tag to a non-human animal so as to directly activate osteoclasts and thus induce osteopenia in a rapid manner (within several days). Such an osteopenia animal model is useful for rapid drug evaluation. The mechanism of bone mass decrease in the osteopenia animal model of the present invention is a very simple mechanism involving osteoclast differentiation and activation promoted by RANKL. Therefore, an evaluation system using such animal is very useful for the exclusive purpose of developing osteoclast inhibitors (e.g., bisphosphonate and Cathepsin K inhibitors). In addition, such animal can be used for evaluation of drugs (e.g., PTH) capable of increasing bone mass based on the comparison of duration from the onset of osteopenia to the recovery from osteopenia.

Specifically, the present invention is described as follows.

[1] A method for producing an osteopenia animal model, comprising administering soluble RANKL or a fused protein of soluble RANKL with an epitope tag to a non-human animal so as to promote in vivo osteoclast differentiation and activation in the non-human animal.

[2] The method for producing an osteopenia animal model according to [1], wherein the epitope tag is glutathione-S-transferase.

[3] The method for producing an osteopenia animal model according to [1] or [2], wherein an osteopenia animal model can be produced within 1 week after administration of soluble RANKL or a fused protein of soluble RANKL with an epitope tag to a non-human animal.

[4] The method for producing an osteopenia animal model according to [3], wherein the osteopenia animal model can be produced within 50 hours.

[5] The method for producing an osteopenia animal model according to [4], wherein the osteopenia animal model can be produced within 24 hours.

[6] The method for producing an osteopenia animal model according to any one of [1] to [5], wherein the non-human animal is a rodent animal.

[7] The method for producing an osteopenia animal model according to [6], wherein the non-human animal is a mouse.

[8] The method for producing an osteopenia animal model according to any one of [1] to [7], wherein an osteopenia animal model with a different osteopenia severity is produced by changing the dose of soluble RANKL or a fused protein of soluble RANKL with an epitope tag.

[9] The method for producing an osteopenia animal model according to any one of [1] to [8], wherein an animal to which soluble RANKL or a fused protein of soluble RANKL with an epitope tag is administered is further subjected to ovariectomy.

[10] The method for producing an osteopenia animal model according to [9], wherein the osteopenia animal model can be produced within 72 hours after administration of soluble RANKL or a fused protein of soluble RANKL with an epitope tag to a non-human animal.

[11] An osteopenia animal model produced by the method according to any one of [1] to [10].

[12] The osteopenia animal model according to [11], in which in vivo bone resorption marker levels have increased compared with those for a normal individual.

[13] The osteopenia animal model according to [11], in which the bone density and/or unit bone mass have decreased compared with those of a normal individual.

[14] The osteopenia animal model according to [13], in which the osteoclast number and/or the trabecular number have decreased compared with those of a normal individual.

[15] The osteopenia animal model according to any one of [11] to [14], in which at least one of the serum estrogen concentration, the serum PTH concentration, and the serum OPG concentration does not fluctuate compared with that for a normal individual.

[16] A method for evaluating a bone resorption suppressant or a bone resorption suppressant candidate substance, comprising administering a bone resorption suppressant or a bone resorption suppressant candidate substance to the osteopenia animal model according to any one of [11] to [15], and evaluating the effects of the bone resorption suppressant or the bone resorption suppressant candidate substance based on whether or not a bone mass increase is observed in response to a bone mass decrease in the osteopenia animal model, wherein the bone resorption suppressant or the bone resorption suppressant candidate substance can be judged to be effective for bone resorption suppression if the bone mass increases.

[17] The method for evaluating a bone resorption suppressant or a bone resorption suppressant candidate substance according to [16], wherein a bone mass increase is determined using, as an indicator, at least one selected from the group consisting of: an increase in an in vivo bone resorption marker level, an increase in the bone density, an increase in the unit bone mass, an increase in the trabecular number, a decreases in the osteoclast number, and an increase in the osteoblast surface area in the osteopenia animal model; and a bone mass increase observed with CT.

[18] A method for evaluating an osteogenesis promoter or an osteogenesis promoter candidate substance, comprising administering an osteogenesis promoter or an osteogenesis promoter candidate substance to the osteopenia animal model according to any one of [11] to [15], and evaluating effects of the osteogenesis promoter or the osteogenesis promoter candidate substance based on whether or not a bone mass increase is observed in response to a bone mass decrease in the osteopenia animal model, wherein the osteogenesis promoter or the osteogenesis promoter candidate substance can be judged to be effective for osteogenesis promotion if the bone mass increases.

[19] The method for evaluating an osteogenesis promoter or an osteogenesis promoter candidate substance according to [18], wherein a bone mass increase is determined using, as an indicator, at least one selected from the group consisting of: an increase in an in vivo bone resorption marker level, an increase in the bone density, an increase in the unit bone mass, an increase in the trabecular number, a decrease in the osteoclast number, and an increase in the osteoblast surface area in the osteopenia animal model; and a bone mass increase observed with CT.

[20] A method for evaluating a hormone or a hormone receptor modulator, comprising administering a hormone or a hormone receptor modulator to an osteopenia animal model produced by administering soluble RANKL or a fused protein of soluble RANKL with an epitope tag by the method according to [8], which has been further subjected to ovariectomy, and evaluating the effects of the hormone or the hormone receptor modulator based on whether or not a bone mass increase is observed in response to a bone mass decrease in the osteopenia animal model, wherein the hormone or the hormone receptor modulator can be judged to be effective for bone resorption suppression if the bone mass increases.

[21] The method for evaluating a hormone or a hormone receptor modulator according to [20], wherein the hormone or the hormone receptor modulator is a selective estrogen receptor modulator.

[22] The method for evaluating a hormone or a hormone receptor modulator according to [20] or [21], wherein a bone mass increase is determined using, as an indicator, at least one selected from the group consisting of: an increase in an in vivo bone resorption marker level, an increase in the bone density, an increase in the unit bone mass, an increase in the trabecular number, a decrease in the osteoclast number, and an increase in the osteoblast surface area in the osteopenia animal model; and a bone mass increase observed with CT.

This description includes part or all of the contents as disclosed in the description and/or drawings of Japanese Patent Application Nos. 2006-278029 and 2007-095017 and International Application No. PCT/JP2007/063871, which are priority documents of the present application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 54 shows images indicating image analysis results (obtained with micro CT) for a male mouse subjected to administration of GST-RANKL and those subjected to administration of PBS.

FIG. 60 shows images indicating image analysis results (obtained with micro CT) for a Fischer rat subjected to administration of GST-RANKL and those subjected to administration of PBS.

FIG. 67 shows images indicating image analysis results (obtained with micro CT) for mice subjected to administration of GST-RANKL and mice subjected to administration of PBS for 7 consecutive days.

BEST MODE FOR CARRYING OUT THE INVENTION

Figure 1:
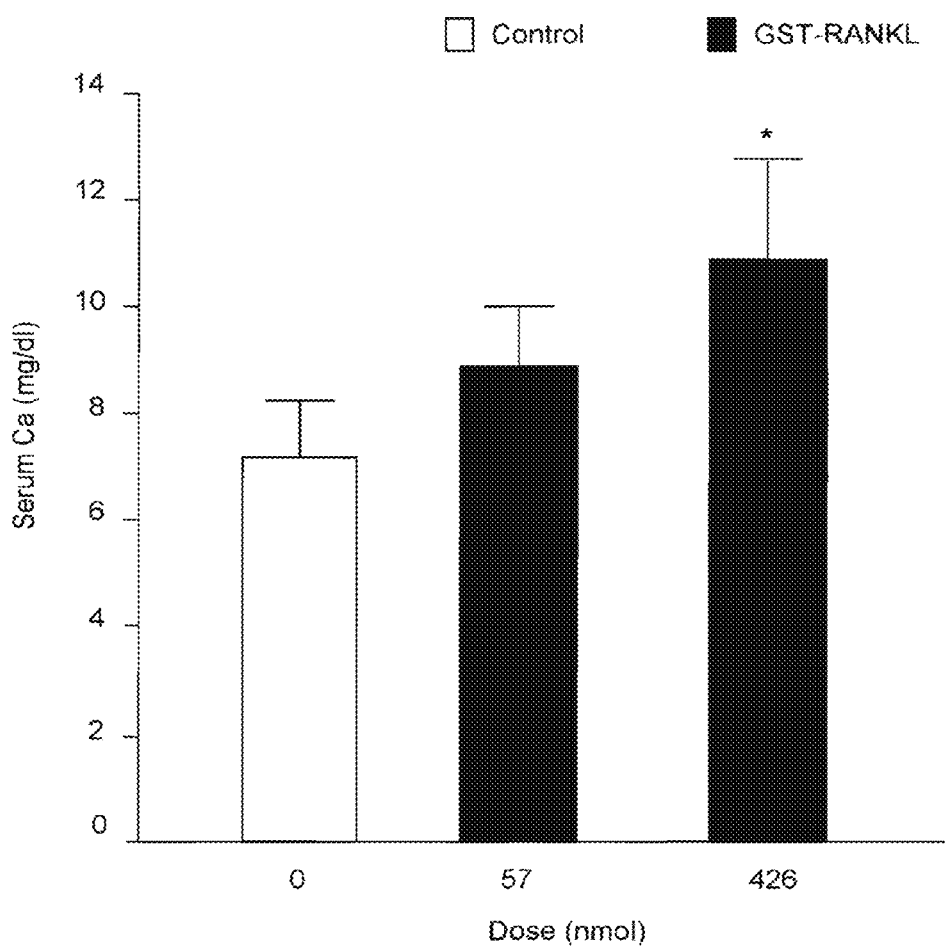
FIG. 1 shows a graph of serum Ca concentrations in mice subjected to administration of GST-RANKL and mice not subjected to administration of the same.

Hereinafter, the present invention is described in detail. The osteopenia animal model of the present invention can be produced by administering soluble RANKL or a fused protein of soluble RANKL with an epitope tag to a non-human animal.

RANKL (receptor activator of NF-κB ligand) serves as a ligand for RANK (receptor activator of NF-κB), which is a TNF super family member, and RANKL is a type 2 transmembrane protein having an intracellular domain (a domain comprising amino acids at positions 1 to 48 from the N-terminal of RANK), a transmembrane domain, and an extracellular domain (JP Patent Publication (Kohyo) No. 2002-509430 A and WO98/46644 (JP Patent No. 3523650)). In the extracellular domain, a domain comprising amino acids at position 152 from the N-terminal and the following positions is a TNF ligand family homologous domain. Soluble RANKL does not contain an intracellular domain. RANKL has functions such as an osteoclast differentiating and activating function, a lymphocyte differentiating function, a dendritic cell activating function, a mammary gland epithelial cell differentiating function, and a lymph node forming function.

Soluble RANKL includes a soluble RANKL derivative and a soluble RANKL analog. The animal origin of soluble RANKL is not limited, and thus RANKL derived from any animal species, such as human-derived RANKL, mouse-derived RANKL, or rat-derived RANKL, can be used. The full-length nucleotide sequence and the amino acid sequence of human-derived RANKL are represented by SEQ ID NOS: 1 and 2, respectively. A soluble RANKL derivative or a soluble RANKL analog includes a protein comprising a partial sequence of the amino acid sequence of RANKL and having the RANKL activity, such as a truncated protein of RANKL. Preferably, a soluble RANKL derivative comprises a TNF ligand family homologous domain starting from an amino acid at position 152 in the amino acid sequence represented by SEQ ID NO: 2. Examples of a soluble RANKL derivative include a protein having an amino acid sequence comprising amino acids at positions 127 to 317, a protein having an amino acid sequence comprising amino acids at positions 140 to 317, and a protein having an amino acid sequence comprising amino acids at positions 159 to 317. Another example thereof is an RANKL derivative derived from a non-human animal, which has an amino acid sequence corresponding to one of the above partial amino acid sequences of human RANKL. Further, examples of a soluble RANKL derivative or a soluble RANKL analog include: a protein having RANKL activity and comprising an amino acid sequence derived from the amino acid sequence represented by SEQ ID NO: 2 by deletion, substitution, or addition of one or several amino acid(s); and a protein having RANKL activity and comprising an amino acid sequence derived from the amino acid sequence of one of the above proteins each comprising a partial amino acid sequence of RANKL by deletion, substitution, or addition of one or several amino acid(s). Herein, the term "one or several" means 1 to 9, preferably 1 to 5, and more preferably 1 or 2.

An epitope tag that forms a fused protein together with soluble RANKL can be a protein or peptide having a sequence capable of binding to a specific compound such as an antibody. In general, an epitope tag is used for fused protein purification. However, in the present invention, an epitope tag has a function of increasing the activity of soluble RANKL.

Examples of an epitope tag include, but are not limited to: glutathione-S-transferase (GST); polyhistidine comprising 2 to 12, preferably 4 or more, more preferably 4 to 7, and further preferably 5 or 6 histidines; FLAG tag (amino acid sequence DYKDDDDK; SEQ ID NO: 3); Myc tag (amino acid sequence EQKLISEEDL; SEQ ID NO: 4); V5 tag (amino acid sequence GKPIPNPLLGLDST; SEQ ID NO: 5); Xpress tag; HQ tag (amino acid sequence HQHQHQ; SEQ ID NO: 6); HA tag (amino acid sequence YPYDVPDYA; SEQ ID NO: 7); AU1 tag (amino acid sequence DTYRYI; SEQ ID NO: 8); T7 tag (amino acid sequence MASMTGGQQMG; SEQ ID NO: 9); VSV-G tag (amino acid sequence YTDIEMNRLGK; SEQ ID NO: 10); DDDDK tag (amino acid sequence DDDDK; SEQ ID NO: 11); S tag (amino acid sequence KETAAAKFERQHIDSC; SEQ ID NO: 12); CruzTag09 (amino acid sequence MKAEFRRQESDR; SEQ ID NO: 13); CruzTag22 (amino acid sequence MRDALDRLDRLA; SEQ ID NO: 14); CruzTag41 (amino acid sequence MKDGEEYSRAFR; SEQ ID NO: 15); Glu-Glu tag (amino acid sequence EEEEYMPME; SEQ ID NO: 16); Ha.11 tag (amino acid sequence CTPTDVPDYASL; SEQ ID NO: 17); KT3 tag (amino acid sequence PPEPET; SEQ ID NO: 18); thioredoxin; a maltose binding protein (MBP); an immunoglobulin Fc region; and β-galactosidase. Of these, glutathione-S-transferase is preferable.

A fused protein of soluble RANKL with an epitope tag can be obtained by ligating the genes encoding the respective components to each other and causing the expression of the resultant. Fusion of the gene encoding RANKL with the gene encoding an epitope tag can be carried out by a conventional gene recombination method with the introduction of appropriate restriction sites. In such case, it is necessary to exclude a stop codon between the genes to be fused. The distance between the genes to be fused is not limited, and a linker may be contained therebetween. In addition, it is necessary to allow the open reading frames of the two genes to overlap each other. The above epitope tag can be fused either on the N-terminal side or on the C-terminal side of the amino acid sequence of RANKL.

The nucleotide sequence of DNA encoding a fused protein of GST with a protein having an amino acid sequence comprising amino acids at positions 127 to 317 of the amino acid sequence of RANKL and the amino acid sequence of the fused protein are represented by SEQ ID NOS: 19 and 20, respectively. The nucleotide sequence of DNA encoding a fused protein of GST with a protein having an amino acid sequence comprising amino acids at positions 140 to 317 of the amino acid sequence of RANKL and the amino acid sequence of the fused protein are represented by SEQ ID NOS: 21 and 22, respectively. In addition, the nucleotide sequence of DNA encoding a fused protein of GST with a protein having an amino acid sequence comprising amino acids at positions 159 to 317 of the amino acid sequence of RANKL and the amino acid sequence of the fused protein are represented by SEQ ID NOS: 23 and 24, respectively.

The thus produced fused gene is incorporated into an appropriate available expression vector so as to be expressed therein such that a fused protein of interest can be recovered and purified. In addition, the gene can be expressed also in a cell-free system.

Any vector can be used as a vector as long as the vector can be replicated in host cells such as plasmids, phages, and viruses. A vector comprises a replication origin, a selection marker, and a promoter. It may further comprise an enhancer, a transcription termination sequence (terminator), a ribosome binding site, a polyadenylation signal, and the like, according to need. Alternatively, a vector into which a gene encoding an epitope tag such as glutathione-S-transferase has been incorporated in a preliminary step can be used.

DNA can be introduced into a vector by a conventionally known method. Desirably, such a vector comprises: a polylinker containing different restriction sites; or a single restriction site. A specific restriction site in a vector is cleaved with a specific restriction enzyme and DNA can be inserted into the cleavage site. An expression vector containing a fused gene is used for transformation of an appropriate host cell such that a fused protein encoded by the fused gene can be expressed and produced in the host cell.

Examples of a host cell include: bacterial cells of *Escherichia coli, Streptomyces, Bacillus subtilis*, and the like; fungal cells; bakers' yeast cells; yeast cells; insect cells; and mammalian cells.

Transformation can be carried out by a conventionally known method such as the calcium chloride method, the calcium phosphate method, DEAE-dextran mediated transfection, electroporation, lipofection, or the like.

The obtained recombinant fusion protein can be purified by a variety of purification methods. For instance, ammonium sulfate precipitation, gel filtration, ion-exchange chromatography, affinity chromatography, and the like can be used alone or in combination according to need. In a case in which an expression product is expressed as a fused protein comprising GST or the like, purification can be carried out based on the characteristics of a protein or peptide fused with a protein of interest. For instance, when a fused protein comprising GST is expressed, GST has an affinity to glutathione and therefore the fused protein can be efficiently purified by affinity chromatography with the use of a column containing glutathione-bound carriers. Also, when a fused protein comprising a histidine tag is expressed, such a protein having a histidine tag binds to a chelate column and therefore the fused protein can be purified with the use of a chelate column. Further, a fused protein comprising an arbitrary epitope tag can be purified by affinity chromatography with the use of an antibody that recognizes an epitope of the epitope tag.

Types of animals to which a soluble RANKL or a fused protein of soluble RANKL with an epitope tag is administered are not limited. All non-human mammals such as mice, rats, guinea pigs, hamsters, horses, bovines, sheep, swines, monkeys, dogs, and cats can be administration targets. Osteopenia animal models can be produced from such animals. In addition, both male and female animals can be used for producing osteopenia animal models. Further, the age of an animal used for producing an osteopenia animal model is not limited. The osteopenia animal model of the present invention can be produced even with the use of an aged animal. For instance, when a mouse is used as an animal in the present invention, a 1- to 52-week-old and preferably 4- to 12-week-old mouse can be used for producing an osteopenia animal model.

The amount of the fused protein of soluble RANKL with an epitope tag to be administered to an animal is not limited, and it can be adequately determined depending on animal species. For instance, the fused protein can be administered to an individual animal in an amount of 10 nmol to 5000 nmol and preferably 50 nmol to 1000 nmol. The administration route is not limited and thus the fused protein can be administered in the form of an intravenous injection, an intraperitoneal injection, a subcutaneous injection, a muscular injection, a suppository, an ophthalmic preparation, or the like. Also, it can be used for administration to the calvarium.

In addition, the number of doses is not limited. Administration can be carried out as single-dose administration or multiple-dose administration 2 to 20 times in a continuous manner. When continuous administration is carried out, the administration intervals are not limited. For instance, administration can be carried out every day for several days. Further, it becomes possible to control the degree of bone mass reduction in a model animal by controlling the total dose. For instance, in the case of single-dose administration, an animal with a high degree of bone mass reduction can be produced by increasing the single dose.

When a soluble RANKL or a fused protein of soluble RANKL with an epitope tag is administered to an animal, an osteopenia animal model can be rapidly produced by a simple mechanism in which such substance directly causes osteoclast differentiation in the animal and osteoclast activation without mediation of a different substance.

The osteopenia animal model of the present invention has the features described below. The term "normal animal" used herein refers to an animal in which no bone metabolism disease is developed or to which soluble RANKL or a fused protein of soluble RANKL with an epitope tag is not administered. For instance, upon production of the osteopenia animal model, an animal to which PBS or the like has been administered can be used as a normal animal as a control case.

(1) The bone resorption marker concentrations (levels) in the body fluid temporarily increase compared with those of an allied normal animal (normal individual). The concentrations would vary depend on the dose of soluble RANKL or a fused protein of soluble RANKL with an epitope tag. However, they become 1.1-fold or more, preferably 1.2-fold or more, further preferably 1.3-fold or more, and particularly preferably 1.4-fold or more as high as such concentrations in a normal animal. Examples of serum bone resorption markers include serum calcium, serum degraded collagen products such as (CTx (type-I collagen-crosslinked C-telopeptide), NTx (type-I collagen-crosslinked N-telopeptide), PICP (type-I procollagen C-propeptide), or PINP (type-I procollagen N-propeptide)), and serum tartrate-resistant acid phosphatase (TRAP-5b). Examples of urinary bone resorption markers include urinary CTx or NTx, urinary hydroxyproline, urinary pyridinoline, and deoxypyridinoline. In addition, hydroxylysine glycoside (in serum and urine), bone sialoprotein (in serum), and the like can be used. Such markers increase when osteoclasts proliferate and thus osteoclast activity is promoted. Such markers are generally used as bone metabolism markers for bone metabolism diseases such as osteoporosis. Such markers can be measured by a colorimetric method and immunoassay using a specific antibody.

(2) The serum osteogenesis marker concentrations (levels) fluctuate less than those of a normal animal. Examples of serum osteogenesis markers include serum osteocalcin (osteocalcin) and serum alkaline phosphatase (particularly bone-specific alkaline phosphatase). Such markers are osteoblast-derived proteins and their concentrations increase upon osteoblast proliferation. Such markers are generally used as bone metabolism markers for bone metabolism diseases such as osteoporosis. Such markers can be measured by a colorimetric method and immunoassay using a specific antibody. Soluble RANKL or a fused protein of soluble RANKL with an epitope tag does not directly act on osteoblasts. However, a coupling phenomenon induced by bone resorption and osteogenesis might indirectly cause the serum osteogenesis marker concentrations to fluctuate. The occurrence or nonoccurrence of fluctuation would vary depending on the administration dose of soluble RANKL or a fused protein of soluble RANKL with an epitope tag, the number of doses, and the time course after administration.

In addition, bone resorption markers described in (1) and osteogenesis markers described in (2) are collectively referred to as bone metabolism markers.

(3) The bone density becomes lower than that of a normal animal. The bone density is expressed with a number representing the density of a bone mineral component such as calcium. The bone density includes the cancellous bone density, the total bone density, and the cortical bone density. According to the present invention, the term "bone density" simply refers to "cancellous bone density." The bone density can be measured with pQCT (peripheral quantitative computerized tomography with a peripheral bone X-ray CT apparatus), DXA (dual energy X-ray absorptiometry), and the like. The bone density would vary depending on the dose of soluble RANKL or a fused protein of soluble RANKL with an epitope tag. However, in the case of the osteopenia animal model of the present invention, when the femur or tibia bone density is measured with pQCT, it is found to have decreased by, for example, 1% or more, 2% or more, 3% or more, 5% or more, preferably 7.5%, further preferably 10% or more, and most preferably 20% or more, although it would vary depending on the distance from the growth plate.

In addition, the total bone density of the osteopenia animal model becomes lower than that of a normal animal. When the femur or tibia bone density is measured with pQCT, the total bone density is found to have decreased by, for example, 1% or more, 2% or more, 3% or more, 5% or more, preferably 7.5% or more, further preferably 10% or more, and most preferably 20% or more, although it would vary depending on the distance from the growth plate.

Further, the cortical bone density of the osteopenia animal model becomes lower than that of a normal animal. When the femur or tibia bone density is measured with pQCT, the cortical bone density is found to have decreased by, for example, 1% or more, 2% or more, 3% or more, 5% or more, preferably 7.5% or more, further preferably 10% or more, and most preferably 20% or more, although it would vary depending on the distance from the growth plate.

Further, the cortical bone mineral content of the osteopenia animal model becomes lower than that of a normal animal. The bone mineral content corresponds to the amount of a bone mineral (hydroxyapatite) and reflects the bone density. The bone mineral content can be measured with pQCT and the like. When the femur or tibia cortical bone mineral content is measured with pQCT, the cortical bone mineral content is found to have decreased by, for example, 5% or more, preferably 7.5% or more, more preferably 10% or more, further preferably 15% or more, and most preferably 20% or more, although it would vary depending on the distance from the growth plate.

Furthermore, the cortical bone thickness of the osteopenia animal model becomes smaller than that of a normal animal. The cortical bone thickness can be measured with pQCT and the like. When the cortical bone thickness in the femur or tibia is measured with pQCT, the cortical bone thickness is found to have decreased by, for example, 5% or more, preferably 7.5% or more, more preferably 10% or more, further preferably 15% or more, and most preferably 20% or more, although it would vary depending on the distance from the growth plate.

(4) Upon bone morphology measurement, the unit bone mass (BV/TV; bone volume/total tissue volume), the trabecular number (Tb.N; trabecular number), and the trabecular width (Tb.Th; trabecular thickness) are found to have become smaller than those of a normal animal. The unit bone mass relates to the total trabecular surface area with respect to the total tissue surface area of a pathologic section. The term "trabecular" is used for a portion containing untwisted epiphyseal bone sponge tissue. In the case of the osteopenia animal model of the present invention, the unit bone mass and the trabecular number decrease by, for example, 10% or more, preferably 20% or more, further preferably 30% or more, furthermore preferably 40% or more, and particularly preferably 50% or more compared with those of a normal animal, although they would vary depending on the dose of soluble RANKL or a fused protein of soluble RANKL with an epitope tag.

(5) The osteoclast number becomes greater than that of a normal animal. The osteoclast number can be counted by a conventional method involving bone morphology measurement. The osteoclast number increases by, for example, 20% or more, preferably 30% or more, further preferably 40% or more, furthermore preferably 50% or more, and particularly preferably 60% or more compared with that of a normal animal, although it would vary depending on the dose of soluble RANKL or a fused protein of soluble RANKL with an epitope tag.

(6) The osteoblast surface area (Ob.S/BS; osteoblast surface area/bone surface area) becomes significantly greater than that of a normal animal. The term "osteoblast surface area" refers to the proportion (%) of an osteoblast adhesion area with respect to the total trabecular surface area. The osteoblast surface area increases by, for example, 20% or more, preferably 30% or more, more preferably 40% or more, further preferably 50% or more, and particularly preferably 60% or more compared with that of a normal animal, although it would vary depending on the dose of soluble RANKL or a fused protein of soluble RANKL with an epitope tag.

In addition, when the dose of a fused protein of soluble RANKL with an epitope tag is increased, such as in a case in which a mouse is subjected to administration at a dose of 2 mg/kg, it takes time to observe a coupling phenomenon induced by bone resorption and osteogenesis so that changes in the osteoblast surface area might be observed with a delay. Therefore, depending on the time of observation of the osteoblast surface area, an increase in the osteoblast surface area might not be observed.

(7) The osteoid thickness (O.Th; osteoid thickness), eroded surface area (ES/BS; eroded surface area/bone surface area), and the osteoclast surface area (Oc.S/Bs; osteoclast surface area/bone surface area) become greater than those of a normal animal. The term "osteoid" refers to a preliminary state before calcification to form a bone matrix takes place. The term "eroded surface area" refers to the proportion of a concave-convex surface area formed by erosion over the entire trabecular surface area. The term "osteoclast surface area" refers to the proportion of an osteoclast adhesion surface over the entire trabecular surface area. The osteoid thickness, the eroded surface area, and the osteoclast surface area increase by, for example, 20% or more, preferably 30% or more, further preferably 40% or more, furthermore preferably 50% or more, and particularly preferably 60% or more compared with those of a normal animal, although they would vary depending on the dose of soluble RANKL or a fused protein of soluble RANKL with an epitope tag.

(8) Upon observation of bone morphology, a bone mass decrease is observed to a greater extent than that observed in a normal animal. Bone morphology can be determined with micro CT and the like.

(9) In the case of the osteopenia animal model of the present invention, estrogen is synthesized in vivo. In such case, the serum estrogen concentration fluctuates less than that of a normal animal. In this regard, the osteopenia animal model differs from conventional animal models produced by ovariectomy. In addition, the serum PTH concentration does not become greater than that of a normal animal. In this regard, the osteopenia animal model differs from conventional animal models produced by supplying a conventional low-calcium concentration food to animals.

Further, the serum OPG (osteoprotegerin) concentration decreases in conventional animal models produced by ovariectomy and conventional animal models produced by supplying a conventional low-calcium concentration food to animals. However, it does not fluctuate in the osteopenia animal model of the present invention.

Further, an osteopenia animal model can be produced by administering soluble RANKL or a fused protein of soluble RANKL with an epitope tag to an animal, followed by ovariectomy. In such case, it is preferable to perform ovariectomy after administration of RANKL. Combined use of ovariectomy and administration of soluble RANKL or a fused protein of soluble RANKL with an epitope tag allows production of an osteopenia animal model in a state similar to a physiological menopause state. The present invention encompasses an osteopenia animal model that can be produced by carrying out administration of soluble RANKL or a fused protein of soluble RANKL with an epitope tag and ovariectomy. Such osteopenia animal model can be used as a pathological animal model for a human with abnormal postmenopausal bone metabolism.

Among the above features, decreases in terms of bone morphology, bone density, and unit bone mass observed with micro CT, which directly reflect osteopenia, are particularly characteristic. Subsequently, an increase in the osteoclast number (osteoclast number/bone perimeter) and a decrease in the trabecular number are characteristic. Further, a decrease in the cortical bone mineral content is also observed.

In addition, the above features are obviously observed in proportion to the dose of GST-RANKL administered. The degree of each feature depends on the dose. The degree of each feature means the severity of osteopenia. The severity of osteopenia in the osteopenia animal model of the present invention can be controlled by changing the dose of GST-RANKL to be administered. That is, a mild osteopenia animal model can be obtained by administering a small dose of GST-RANKL. A severe osteopenia animal model can be obtained by administering a large dose of GST-RANKL. The term "severe osteopenia animal model" used herein indicates an animal model in which the above features are strongly expressed. For instance, in such animal model, the bone resorption marker concentrations (levels) in the body fluid temporarily relatively increase to a greater extent than those of an allied normal animal (normal individual). The concentrations in such animal model increase to become, for example, 1.2-fold or more, preferably 1.3-fold or more, and further preferably 1.4-fold or more as high as those for a normal animal. In addition, in such animal model, the bone density relatively sharply becomes lower than that for a normal animal. When the femur or tibia bone density of such animal model is measured with pQCT, the bone density is found to have decreased by, for example 7.5% or more, preferably 10% or more, and more preferably 20% or more, although it would vary depending on the distance from the growth plate. Further, upon bone morphology measurement, in such animal model, the unit bone mass (BV/TV; bone volume/total tissue volume), the trabecular number (Tb.N; trabecular number), and the trabecular width (Tb.Th; trabecular thickness) are found to have relatively sharply decreased in comparison with those of a normal animal. They decrease by, for example, 10% or more, preferably 20% or more, further preferably 30% or more, furthermore preferably 40% or more, and particularly preferably 50% or more compared with those of a normal animal. Further, upon bone morphology measurement, in such animal model, the osteoid thickness (O.Th; osteoid thickness), the eroded surface area (ES/BS; eroded surface area/bone surface area), and the osteoclast surface area (Oc.S/Bs; osteoclast surface area/bone surface area) are found to have relatively sharply increased in comparison with those of a normal animal. They increase by, for example, 20% or more, preferably 30% or more, further preferably 40% or more, furthermore preferably 50% or more, and particularly preferably 60% or more compared with those of a normal animal.

Accordingly, typical examples of the osteopenia animal model of the present invention include an animal experiencing decreases in a bone density and/or unit bone mass compared with a normal animal and an animal experiencing decreases in the osteoclast number and/or the trabecular number compared with a normal animal. Further, examples thereof also include an animal experiencing a decrease in the trabecular width compared with a normal animal, and an animal experiencing increases in the osteoid thickness, the eroded surface area, the osteoclast surface area, and the like compared with a normal animal.

In addition, after soluble RANKL and a fused protein of soluble RANKL with an epitope tag are administered to an animal, the above features are gradually observed with time until they are observed to reach the greatest extent. Thereafter, osteogenesis proceeds and the above features are gradually attenuated. Eventually, a normal state is restored. Specifically, the feature of a bone mass decrease is observed in a reversible manner in an osteopenia animal model obtained by administration of soluble RANKL and a fused protein of soluble RANKL with an epitope tag.

In particular, among the above features, the bone resorption markers described in (1) fluctuate after administration of soluble RANKL or a fused protein of soluble RANKL with an epitope tag. However, the markers gradually increase after an osteopenia animal is produced and returns to the normal levels after the elapse of a certain period of time.

As described below, when a drug for bone metabolism is evaluated or screened for with the use of the osteopenia animal model of the present invention, an animal model in an appropriate state, such as a state of experiencing a decrease in bone mass, a state of experiencing the largest decrease in bone mass, or a state of experiencing an increase in bone mass following a temporal decrease in bone mass, is used in accordance with the purpose. Therefore, regardless of the degrees of the above features expressed, an animal experiencing a decrease in bone mass after administration of soluble RANKL or a fused protein of soluble RANKL with an epitope tag and expressing any of the above features can be included among the examples of the osteopenia animal model of the present invention.

As described above, the osteopenia animal model of the present invention is produced by a simple mechanism that does not involve mediation of a different substance. Therefore, after soluble RANKL or a fused protein of soluble RANKL with an epitope tag is administered to a normal animal, and the animal starts to exhibit the above features within 1 week, preferably 3 days (within 72 hours), further preferably 2 days (within 50 hours), and furthermore preferably 24 hours after administration. Thus, the osteopenia animal model is produced.

The osteopenia animal model of the present invention can be used as a disease animal model with an abnormal bone metabolism disease with bone loss, such as osteoporosis, hypercalcemia, Paget disease, renal osteodystrophy, rickets/ osteomalacia, rheumatoid arthritis, or the like. Specifically, the osteopenia animal model can be used in a manner as described below.

The osteopenia animal model of the present invention can be used for evaluating a bone resorption suppressant or for screening for a novel bone resorption suppressant (bone resorption inhibitor). In the present invention, such use is sometimes referred to as "evaluation of a bone resorption suppressant or a bone resorption suppressant candidate substance." Examples of known bone resorption suppressants include: bisphosphonates such as risedronate, etidronate, and alendronate; calcitonin; Cathepsin K inhibitors; and proton pump inhibitors. Bone resorption suppressants are effective when the bone mass decreases. Therefore, preferably, evaluation is carried out at a time at which the bone mass has decreased after administration of soluble RANKL or a fused protein of soluble RANKL with an epitope tag. At such time, effects of a bone resorption suppressant or a bone resorption suppressant candidate substance can be evaluated based on whether or not bone loss can be suppressed by administration of a bone resorption suppressant or a bone resorption suppressant candidate substance to the osteopenia animal model of the present invention. In addition, administration of such a candidate substance may be carried out, for example, 1 to 3 days and preferably 1 day before administration of soluble RANKL or a fused protein of soluble RANKL with an epitope tag. That is to say, evaluation can be carried out based on whether or not the bone mass of an osteopenia animal model becomes less likely to decrease or whether or not the bone mass in such an animal model increases. Specifically, a bone mass increase can be determined based on at least one indicator selected from the group consisting of: a decrease in an in vivo bone resorption marker level, an increase in the bone density, an increase in the unit bone mass, an increase in the trabecular number, an increase in the trabecular width, an increase in the osteoid thickness, an increase in the eroded surface area, a decrease in the osteoclast number, and an increase in the osteoblast surface area in the osteopenia animal model; and a bone mass increase observed with CT. Drug evaluation can be carried out within several days (e.g., 3 to 4 days) with the use of the animal model of the present invention.

Further, the ovariectomized osteopenia animal model of the present invention can be used for evaluating a drug such as a hormone (e.g., estrogen or androgen) or a hormone receptor modulator or screening for a novel hormone receptor modulator. A selective estrogen receptor modulator, which is a hormone receptor modulator, is an osteogenesis suppressant, and it exhibits effects of suppressing bone resorption because it has effects similar to those of estrogen, which is a hormone. It is difficult to evaluate such drug with the use of a usual wild animal containing endogenous estrogen. Drug evaluation of a selective estrogen receptor modulator can be carried out in a significantly rapid manner with the use of the osteopenia animal model of the present invention subjected to ovariectomy (OVX), compared with the case of evaluation with the use of a simply ovariectomized animal model. In the case of using a simply ovariectomized animal model, it takes at least several weeks to confirm effects of a drug for evaluation of the drug. However, in the case of using the ovariectomized osteopenia animal model of the present invention, evaluation can be carried out within half of the above period, for example, 2 weeks, preferably 1 week, and more preferably several days. An example of known selective estrogen receptor modulator is raloxifene. Also, it is possible to evaluate a hormone-like compound or a hormone receptor modulator candidate substance having unknown effects. A hormone, a hormone receptor modulator, or the like can be evaluated based on whether or not a bone mass increase is observed in response to a bone mass decrease in an osteopenia animal model, following administration of the hormone, hormone receptor modulator, or the like to the osteopenia animal model.

In addition, the osteopenia animal model of the present invention can be used for evaluating an osteogenesis promoter or screening for a novel osteogenesis promoter. In the present invention, such use is sometimes referred to as "evaluation of an osteogenesis promoter or an osteogenesis promoter candidate substance." Such an osteogenesis promoter exhibits its effects when the temporally decreased bone mass returns to the initial level. Therefore, it is preferable to carry out evaluation when the temporally decreased bone mass increases again after a period in which the bone mass continuously decreased after administration of soluble RANKL or a fused protein of soluble RANKL with an epitope tag, following which the bone mass stopped decreasing. At such time, effects of an osteogenesis promoter or an osteogenesis promoter candidate substance can be evaluated based on whether or not a bone mass increase can be promoted by administration of the osteogenesis promoter or the osteogenesis promoter candidate substance to the osteopenia animal model of the present invention. In this case, it is preferable to administer a candidate substance after administering soluble RANKL or a fused protein of soluble RANKL with an epitope tag to an animal and confirming a bone mass decrease in the animal. Evaluation can be carried out based on whether or not a bone mass increase is observed in response to a bone mass decrease in an osteopenia animal model. Specifically, a bone mass increase can be determined based on at least one indicator selected from the group consisting of: an increase in an in vivo bone resorption marker level, an increase in the bone density, an increase in the unit bone mass, an increase in the trabecular number, an increase in the trabecular width, an increase in the osteoid thickness, decreases in the osteoclast number and in the eroded surface area, and an increase in the osteoblast surface area in the osteopenia animal model; and a bone mass increase observed with CT. Examples of an osteogenesis promoter include PTH (parathyroid hormone).

The above bone resorption suppressant and the osteogenesis promoter can be used as therapeutic agents for osteoporosis and osteopenia.

Further, the osteopenia animal model of the present invention can be used as an experimental animal for bone metabolism studies. Specifically, in the case of the osteopenia animal model of the present invention, osteogenesis (coupling) is caused as a result of bone resorption. Thus, the animal model can be used for basic studies of elucidation of bone remodeling control mechanisms, and the like. In addition, it can be used for searching for coupling factors for coupling induced by bone resorption and osteogenesis. Further, it can be used for evaluation of drugs capable of inhibiting RANKL signals and studies of mechanisms involving osteoclast differentiation and the like. Examples of a drug capable of suppressing RANKL signals include LFM-A13, which is a Tec kinase family inhibitor.

Furthermore, in the case of the osteopenia animal model of the present invention, a bone mass decrease is observed within just 1 to 2 days after administration of soluble RANKL or a fused protein of soluble RANKL with an epitope tag. Therefore, such animal model can be used for practical training for examining in vivo osteopenia in educational institutions such as universities. Also, the osteopenia animal model of the present invention can be provided to researchers by delivering osteopenia animal model, to which soluble RANKL or a fused protein of soluble RANKL with an epitope tag has been administered to research institutes such as universities and pharmaceutical manufacturers.

The present invention is hereafter described in greater detail with reference to the following examples, although the technical scope of the present invention is not limited thereto.

Example 1

Production of Osteopenia Model Mice (1)

Preparation of GST-RANKL

SalI and NotI sites were added to cDNA encoding human RANKL residues 140-317 by PCR. The resultant was cloned downstream of Glutathione S-transferase of pGEX-4T-2 (GE healthcare; Genbank Accession Number: U13854) with the use of the endonucleases. Protein expression was induced in BL21 (DE3) *Escherischia coli* (Invitrogen) with IPTG (final concentration: 0.5 mM). Then, bacterial cells were suspended in an extraction buffer (50 mM Tris-HCl (pH 8.0), 100 mM NaCl, 1 mM EDTA, 1 mM DTT, and 1% (v/v) TritonX-100) and pulverized at 4° C. with the use of a sonicator. After centrifugation at 18000×g for 15 minutes, the supernatant was recovered and applied to a Glutathione Sepharose column. Subsequently, washing with a washing buffer (50 mM Tris-HCl (pH 8.0), 100 mM NaCl, 1 mM DTT, 0.1% (v/v) TritonX-100) was carried out, followed by elution with a Glutathione solution (20 mM reduced glutathione and 50 mM Tris-HCl (pH 8.0)). The molecular weight and purity of purified GST-RANKL were confirmed by SDS-PAGE. The obtained GST-RANKL was subjected to filter filtration. The molecular weight was 47.0 kDa and the purity was 95% or more. In addition, the endotoxin concentration was determined by limulus amebocyte lysate assay and it was confirmed to be less than 1 EU/µg.

GST-RANKL Administration Test

GST-RANKL was intraperitoneally administered 3 times to groups of 7-week-old female C57BL/6N mice (10 individuals each) at doses of 57 nmol (low dose) and 426 nmol (high dose) every 24 hours. Exsanguination was performed 1.5 hours after the 3rd administration. A group to which PBS was administered in the same manner as above was used as a control group for comparison.

The exsanguinated blood was subjected to measurement of serum bone resorption parameters (calcium, CTx, TRAP-5b) and serum osteogenesis parameters (osteocalcin and alkaline phosphatase (ALP)). Calcium was measured by the OCPC method (WAKO, 272-21801). CTx (Nordic Bioscience Diagnostics), TRAP-5b (IDS Ltd, SB-TR103), and osteocalcin (Biomedical Technologies Inc.) were measured by ELISA. ALP was measured by the Bessey-Lowry method (WAKO, 274-04401).

The following organs were collected from each exsanguinated mouse: the femur, the tibia, the cerebrum, the lungs, the heart, the liver, the thymus, the spleen, the kidneys, and the skin. Naturally occurring lesions were observed by HE staining of the cerebrum, the lungs, the heart, the liver, the thymus, the spleen, the kidneys, and the skin.

Regarding the femur, the cancellous bone was subjected to bone density measurement with the use of pQCT at points 0.6 mm, 0.8 mm, and 1.0 mm from the distal growth plate on the proximal side at the distal end of the femur. Regarding the tibia, tibia sections were prepared for bone morphology measurement. Measurement values were compared with those for a control group by the Dunnett method for testing.

Bone Resorption Parameters and Osteogenesis Parameters

Figure 2:
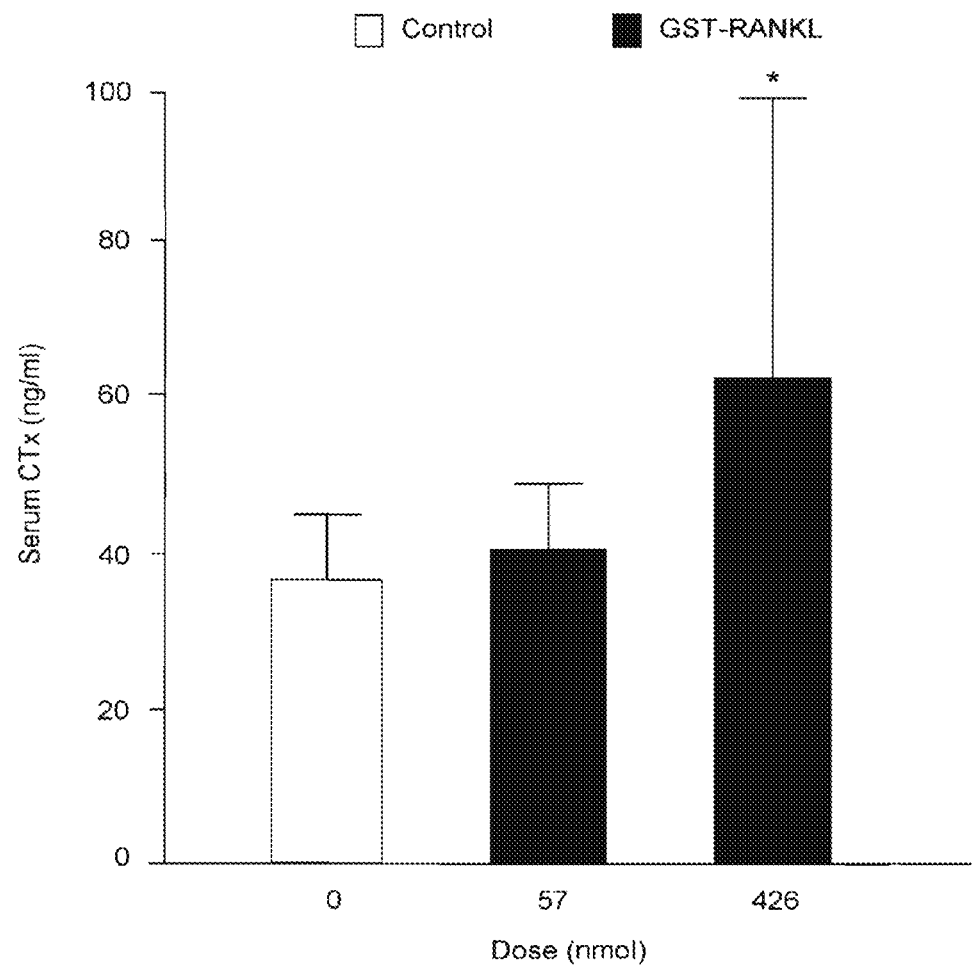
FIG. 2 shows a graph of serum CTx concentrations in mice subjected to administration of GST-RANKL and mice not subjected to administration of the same.
Figure 3:
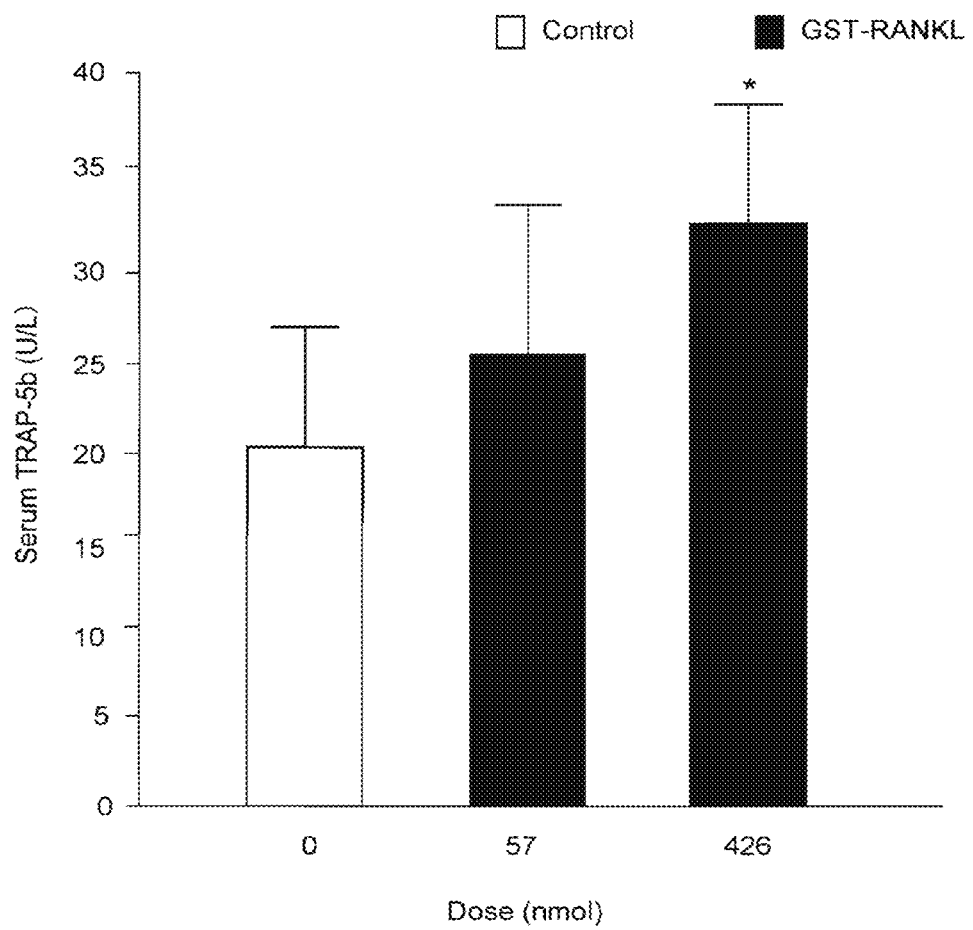
FIG. 3 shows a graph of serum TRAP-5b concentrations in mice subjected to administration of GST-RANKL and mice not subjected to administration of the same.
Figure 4:
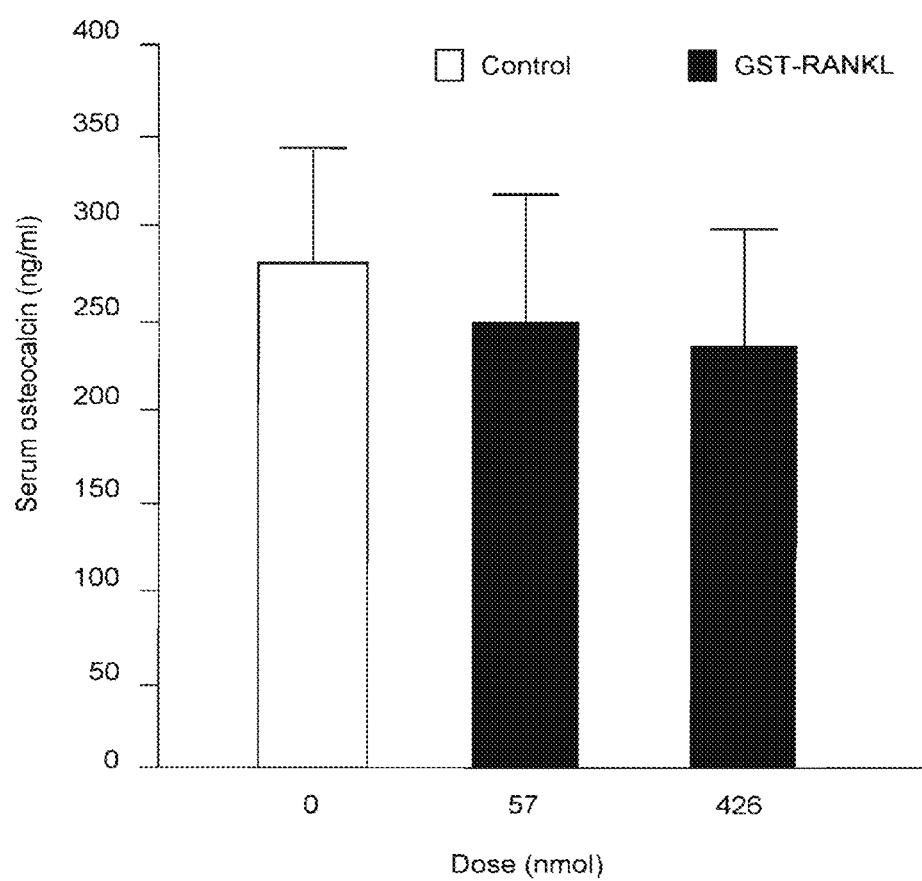
FIG. 4 shows a graph of serum osteocalcin concentrations in mice subjected to administration of GST-RANKL and mice not subjected to administration of the same.
Figure 5:
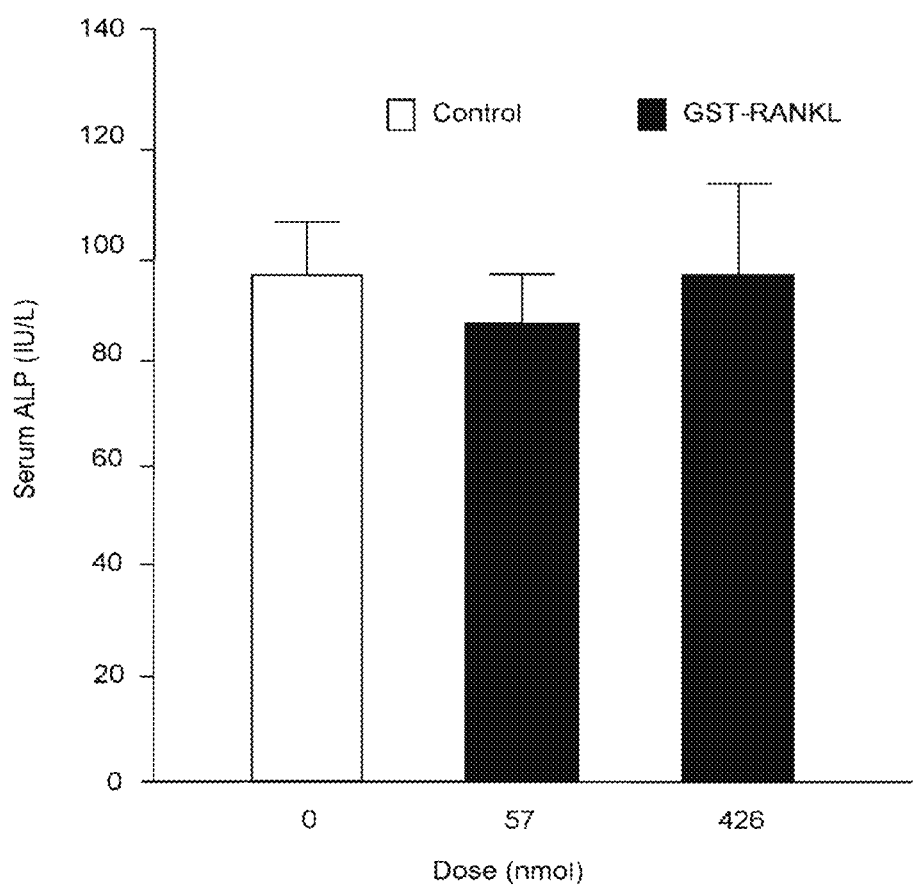
FIG. 5 shows a graph of serum ALP concentrations in mice subjected to administration of GST-RANKL and mice not subjected to administration of the same.

As a result of high-dose administration of GST-RANKL, the serum Ca concentration significantly increased to approximately 1.4-fold as high ($p<0.01$) (FIG. 1). Regarding CTx, which is a collagen metabolite, the concentration for the high-dose administration group significantly increased to approximately 1.5-fold as high as that for the control group ($p<0.01$) (FIG. 2). Regarding TRAP-5b, as a result of high-dose GST-RANKL administration, the concentration significantly increased to approximately 1.5-fold as high ($p<0.01$) (FIG. 3). The serum osteocalcin and ALP concentrations did not vary in either the case of high-dose GST-RANKL administration or the case of low-dose GST-RANKL administration (FIGS. 4 and 5).

Bone Density and Bone Morphology Measurement

Figure 6:
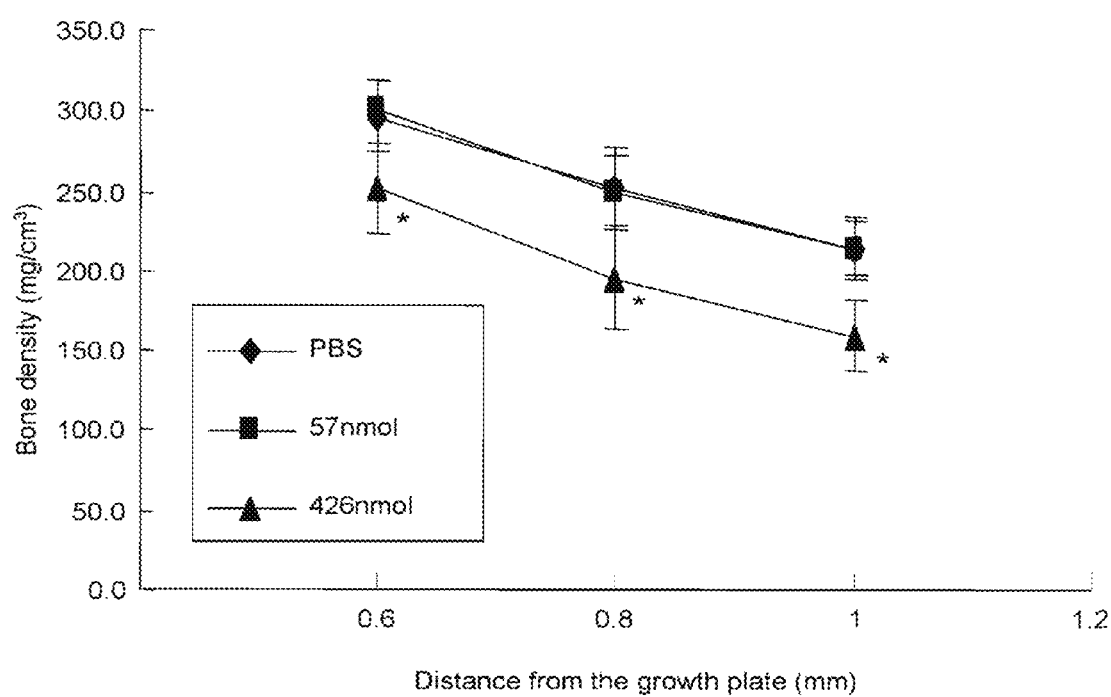
FIG. 6 shows a graph of femur bone densities in mice subjected to administration of GST-RANKL and mice not subjected to administration of the same.

As a result of bone density measurement of the femur with pQCT, the bone density decreased by 10%, 23%, and 20% at the 0.6-, 0.8-, and 1.0-mm points from the distal growth plate on the proximal side, respectively, in the case of high-dose GST-RANKL administration. Verification of the significant difference was carried out by the Anova and Dunnett methods. Accordingly, the significant difference was $p<0.01$ for each measurement point in the case of high-dose GST-RANKL administration. In addition, no significant difference was obtained in the case of low-dose GST-RANKL administration (FIG. 6).

Figure 7:
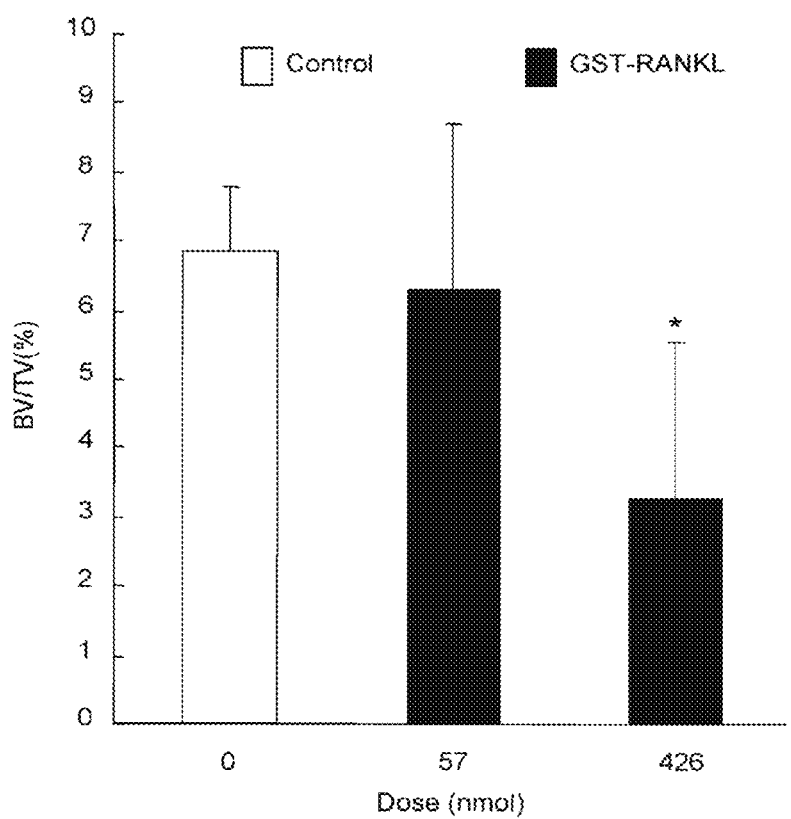
FIG. 7 shows a graph of tibial unit bone masses in mice subjected to administration of GST-RANKL and mice not subjected to administration of the same.
Figure 8:
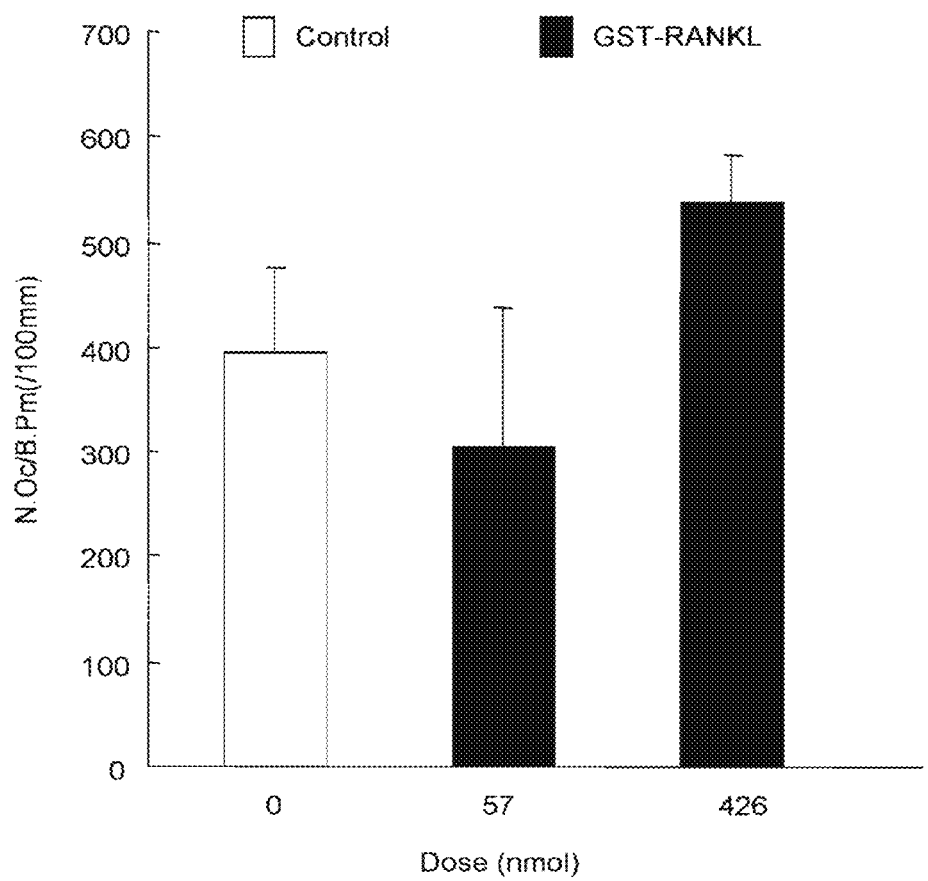
FIG. 8 shows a graph of tibial osteoclast numbers in mice subjected to administration of GST-RANKL and mice not subjected to administration of the same.
Figure 9:
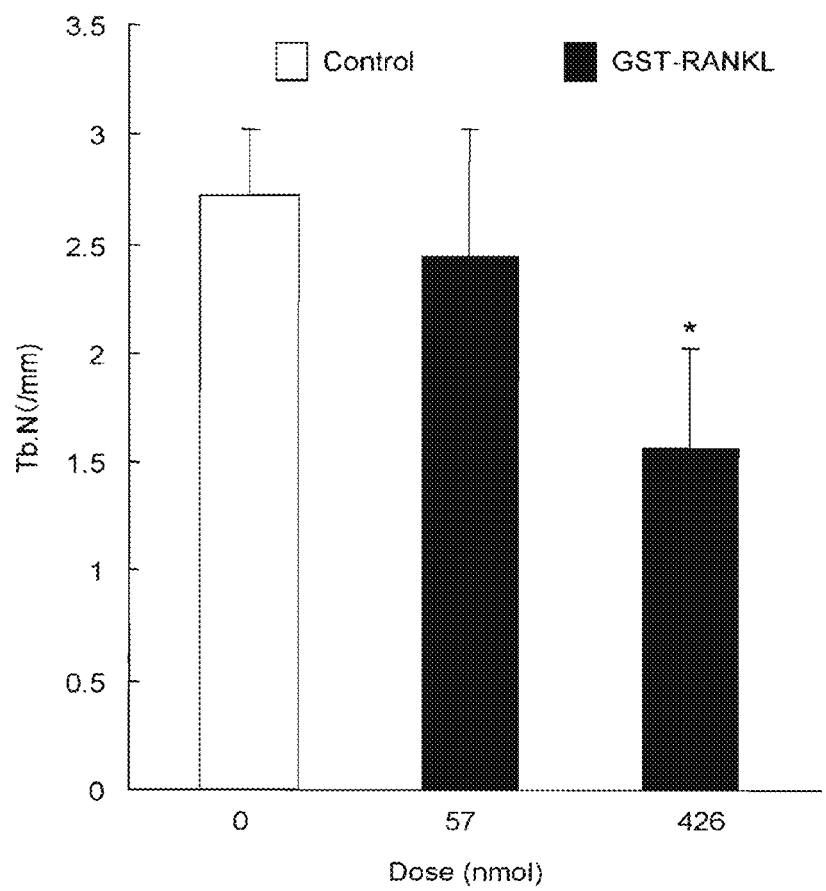
FIG. 9 shows a graph of tibial trabecular numbers in mice subjected to administration of GST-RANKL and mice not subjected to administration of the same.

As a result of bone morphology measurement, the unit bone mass and the trabecular number were found to have each decreased by approximately 50% in the case of high-dose GST-RANKL administration, while the osteoclast number was found to have increased. In addition, no decrease was observed in the case of low-dose GST-RANKL administration (FIGS. 7, 8, and 9).

Figure 10:
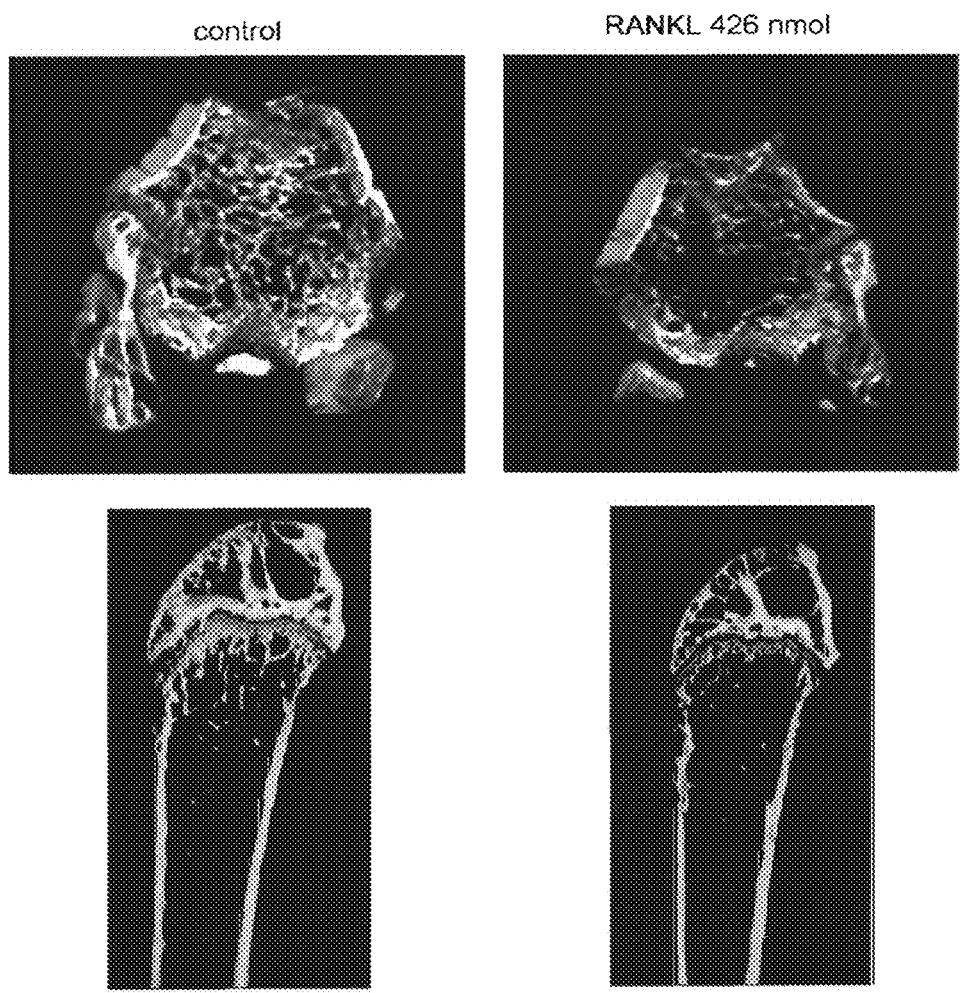
FIG. 10 shows bone morphology images (obtained with micro CT) of the femurs of mice treated with GST-RANKL and mice not treated with the same.

Upon bone morphology measurement of the femur with micro CT, significant bone decreases were observed in the high-dose GST-RANKL administration group (FIG. 10).

The collected organs (the cerebrum, the lungs, the heart, the liver, the thymus, the spleen, the kidneys, and the skin) were subjected to HE staining, followed by observation. Abnormal findings and naturally occurring lesions were not observed in any group.

As a result of high-dose GST-RANKL administration, the following were observed: increases in bone resorption parameters; decreases in the bone density, the unit bone mass, and the trabecular number; and an increase in the osteoclast number. Therefore, mice obtained by high-dose GST-RANKL administration can be used as osteopenia mouse models. Osteopenia mouse models can be produced in a simplified manner within a shortened time period compared with conventional methods.

Osteoblast Surface Area

Figure 11:
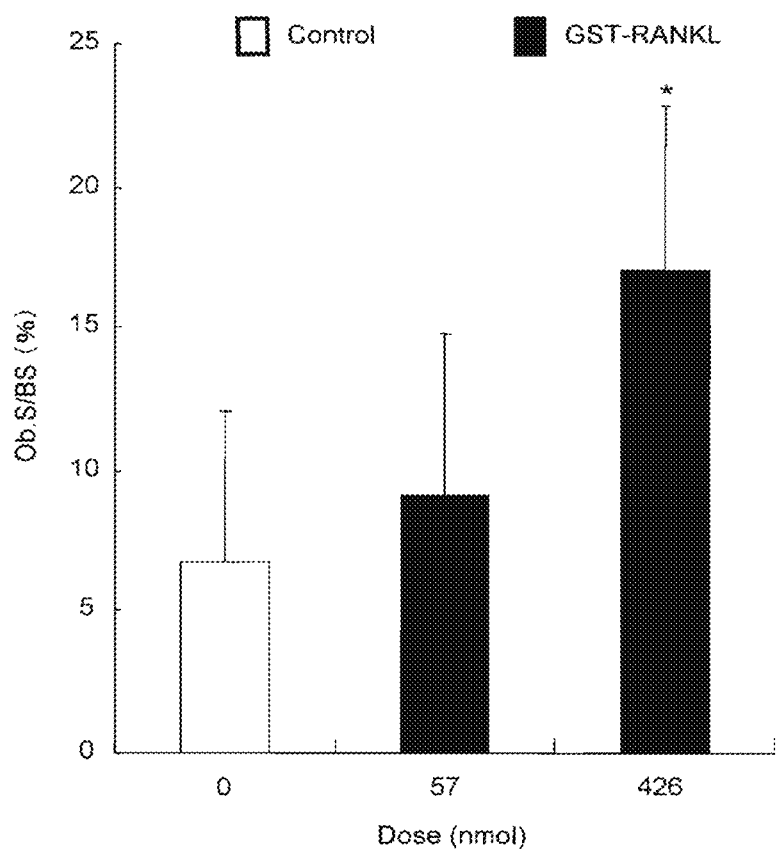
FIG. 11 shows a graph of tibial osteoblast surface areas for mice subjected to administration of GST-RANKL and mice not subjected to administration of the same.

As a result of high-dose GST-RANKL administration, an increase in the osteoclast number, a bone mass decrease, and bone resorption were observed. Further, the osteoblast surface area was examined and a significant osteoblast surface area increase was found (FIG. 11). This suggests that a coupling phenomenon induced by bone resorption and osteogenesis, which is a phenomenon whereby osteogenesis promotion is induced by bone resorption promotion as a result of an increase in the osteoclast number and osteoclast activation, can be observed in the above model case. However, the serum osteocalcin concentration serving as an osteoblast marker and the alkaline phosphatase activity did not vary, indicating that osteoblast activation was in the very early phase in the above case.

Example 2

Production of Osteopenia Model Mice (2)

GST-RANKL was prepared in the same manner as in Example 1.

RANKL Administration Test

GST-RANKL was separately administered 3 times via an intraperitoneal route to groups of 7-week-old female C57BL/6N mice (10 individuals each) at doses of 213 nmol, 426 nmol, and 852 nmol every 24 hours. Exsanguination was performed 1.5 hours after the $3^{rd}$ administration. A group to which PBS was administered in the same manner as above was used as a control group for comparison. 213 nmol, 426 nmol and 852 nmol of GST-RANKL correspond to 10 μg, 20 μg and 40 μg, respectively.

The exsanguinated blood was subjected to measurement of serum bone resorption parameters (calcium, CTx, TRAP-5b) and serum osteogenesis parameters (osteocalcin and alkaline phosphatase (ALP)). Calcium was measured by the OCPC method (WAKO, 272-21801). CTx (Nordic Bioscience Diagnostics), TRAP-5b (IDS Ltd, SB-TR103), and osteocalcin (Biomedical Technologies Inc.) were measured by ELISA. ALP was measured by the Bessey-Lowry method (WAKO, 274-04401).

The femur and the tibia were collected from each exsanguinated mouse. Regarding the femur, the cancellous bone was subjected to bone density measurement with the use of pQCT at points 0.6 mm, 0.8 mm, and 1.0 mm from the distal growth plate on the proximal side. Measurement values were compared with those for a control group by the Dunnett method for testing.

Figure 12:
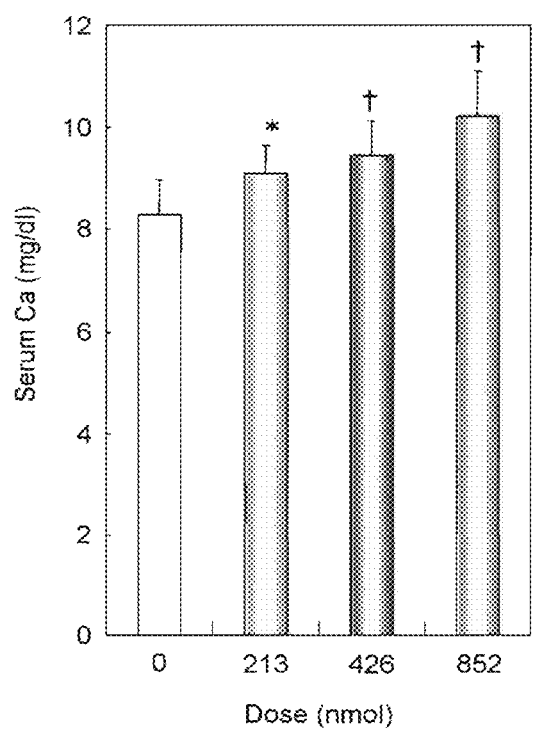
FIG. 12 shows a graph of serum Ca concentrations in mice subjected to administration of GST-RANKL (213 nmol to 852 nmol) and mice not subjected to administration of the same.
Figure 13:
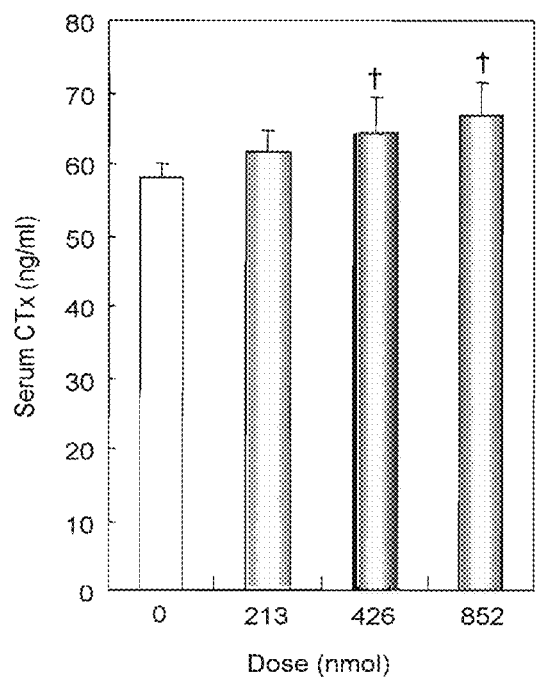
FIG. 13 shows a graph of serum CTx concentrations in mice subjected to administration of GST-RANKL (213 nmol to 852 nmol) and mice not subjected to administration of the same.
Figure 14:
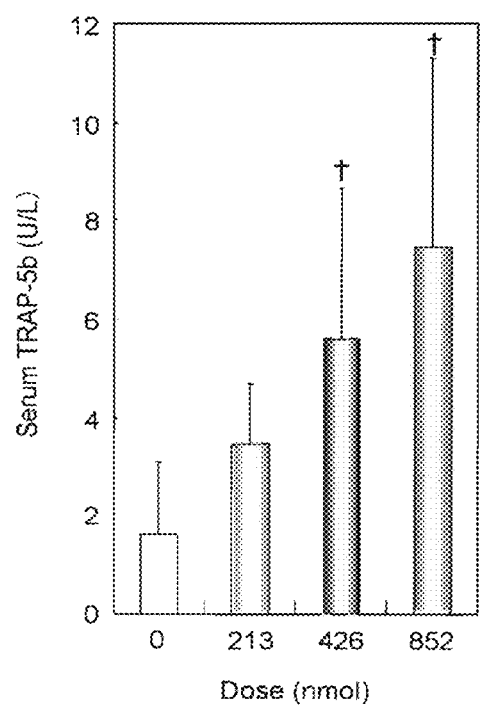
FIG. 14 shows a graph of serum TRAP-5b concentrations in mice subjected to administration of GST-RANKL (213 nmol to 852 nmol) and mice not subjected to administration of the same.

As a result of GST-RANKL administration, the serum Ca, CTx, and TRAP-5b concentrations were found to have increased in a dose-dependent manner (FIGS. 12, 13, and 14, respectively). The calcium concentration significantly increased in the case of 213-nmol administration ($p<0.05$). Further, it obviously increased in the cases of 426-nmol administration and 852-nmol administration ($p<0.01$). No significant increases in the CTx and TRAP-5b concentrations were observed in the case of 213-nmol administration. However, significant increases were obviously observed in the cases of 426-nmol administration and 852-nmol administration ($p<0.01$).

Figure 15:
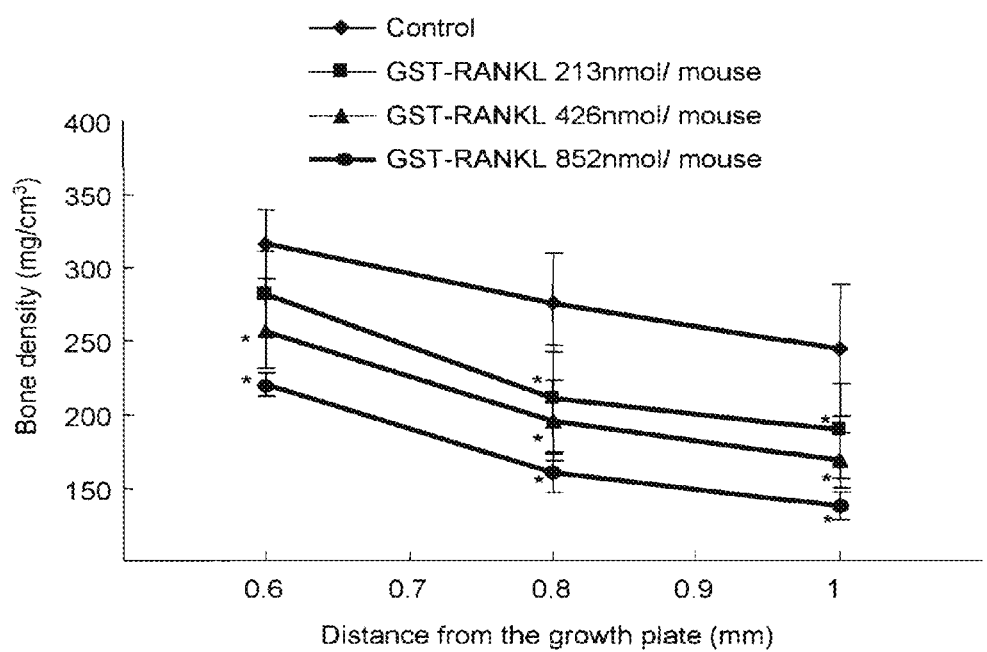
FIG. 15 shows a graph of femur bone densities in mice subjected to administration of GST-RANKL (213 nmol to 852 nmol) and mice not subjected to administration of the same.
Figure 16:
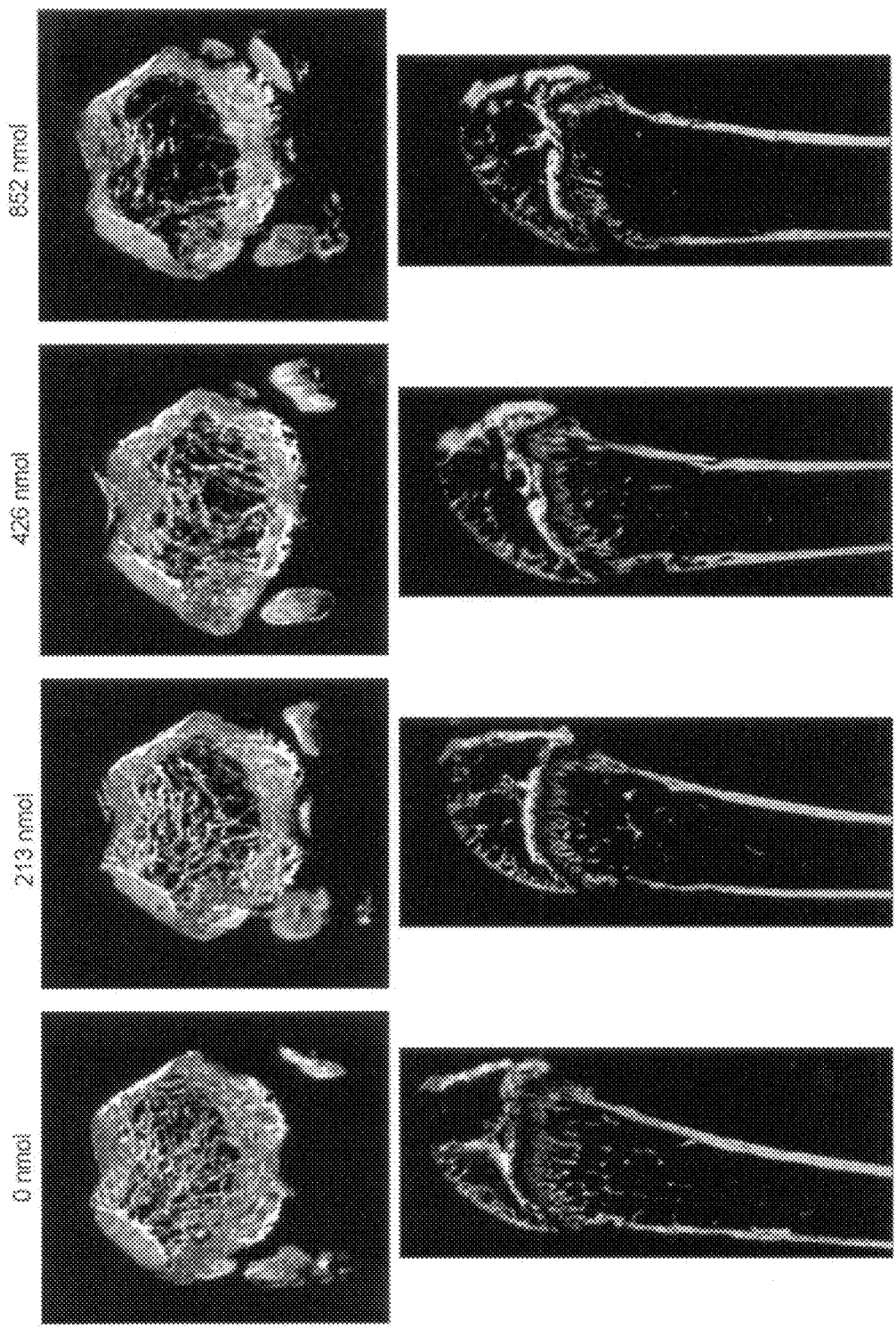
FIG. 16 bone morphology images (obtained with micro CT) of the femurs of mice subjected to administration of GST-RANKL (213 nmol to 852 nmol) and mice not subjected to administration of the same.

When bone density measurement was carried out with the use of pQCT, the bone density was found to have decreased by 11%, 19% ($P<0.01$), and 30% ($P<0.01$) at the point 0.6 mm from the distal growth plate on the proximal side at doses of 213, 426, and 852 nmol, respectively, in the case of GST-RANKL administration. Also, the bone density decreased by 23% ($p<0.01$), 29% ($p<0.01$), and 42% ($p<0.01$) at the point 0.8 mm from the distal growth plate, and by 23% ($p<0.01$), 31% ($p<0.01$), and 44% ($p<0.01$) at the point 1.0 mm from the distal growth plate (FIG. 15). Such dose-dependent decreases in the bone density were observed by image analysis with micro CT (FIG. 16). The above results indicate that a mouse model can be produced by a simple method involving intraperitoneal administration within approximately 50 hours according to the method of the present invention, while on the other hand, it is necessary to perform a particular technique such as ovariectomy (OVX) to produce a mouse model by a conventional method, which takes a long period of time, such as several weeks. In addition, there has been no conventional technique for producing a mouse model in which the severity levels of osteoporosis and osteopenia can be readily changed. However, according to the present invention, increases in bone resorption parameters and a bone mass decrease can be arbitrarily controlled by administration of GST-RANKL at changeable doses. Thus, a mouse model with osteoporosis and osteopenia at predetermined severity levels can be produced.

Example 3

Evaluation of an Osteoporosis Therapeutic Agent with the Use of GST-RANKL-Administered Mice GST-RANKL was prepared in the same manner as in Example 1.

GST-RANKL (426 nmol) was intraperitoneally administered 3 times to groups of 7-week-old female C57BL/6N mice (5 to 6 individuals each) every 24 hours. An osteoporosis therapeutic agent (risedronate) was subcutaneously administered at 0.01 mg/kg every 24 hours from 3 days before GST-RANKL administration. Administration of the agent was continued to the end of the experimentation every 24 hours. The serum, femur, and tibia were collected from each mouse 1.5 hours after the $3^{rd}$ administration of GST-RANKL. Bone resorption parameters (calcium, CTx, and TRAP-5b) and osteogenesis parameters (osteocalcin and ALP) in the serum were measured. The femur bone density was determined with the use of pQCT and micro CT. Measurement values were compared with those for a control group by the Dunnett method for testing.

Figure 17:
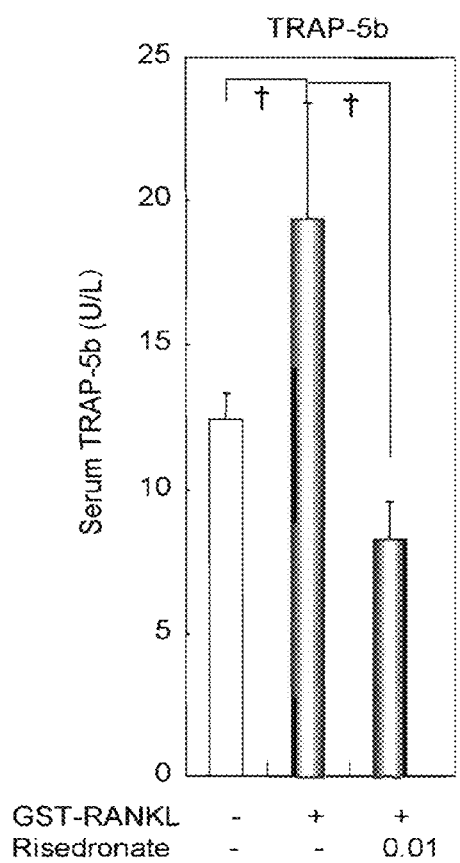
FIG. 17 shows a graph of serum TRAP-5b concentrations in osteopenia model mice produced by GST-RANKL administration and subjected to risedronate administration.
Figure 18:
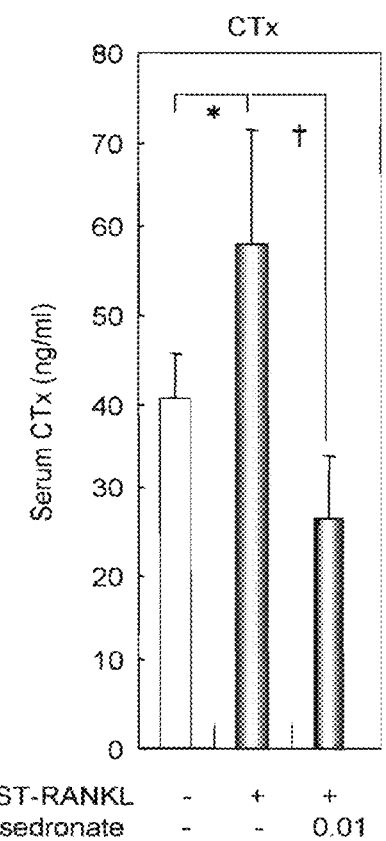
FIG. 18 shows a graph of serum CTx concentrations in osteopenia model mice produced by GST-RANKL administration and subjected to risedronate administration.
Figure 19:
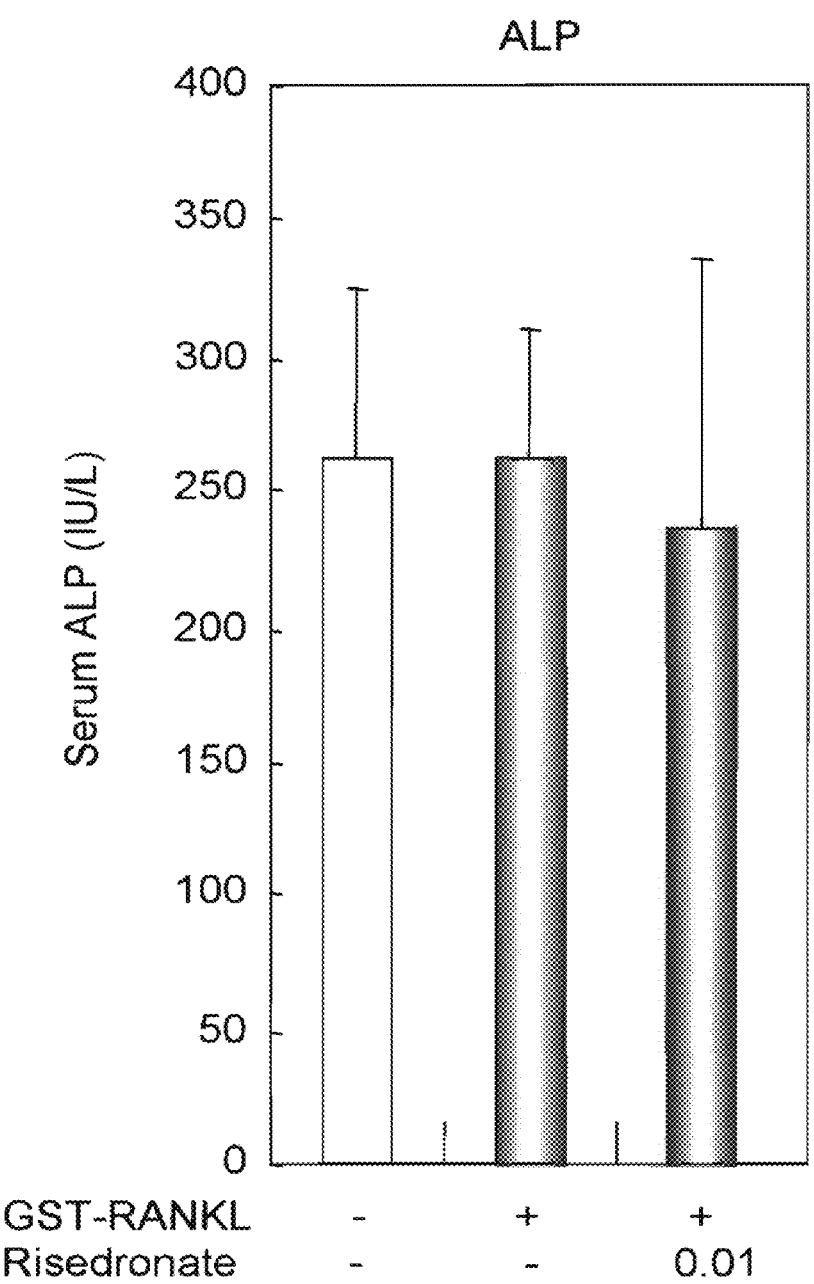
FIG. 19 shows a graph of serum ALP concentrations in osteopenia model mice produced by GST-RANKL administration and subjected to risedronate administration.
Figure 20:
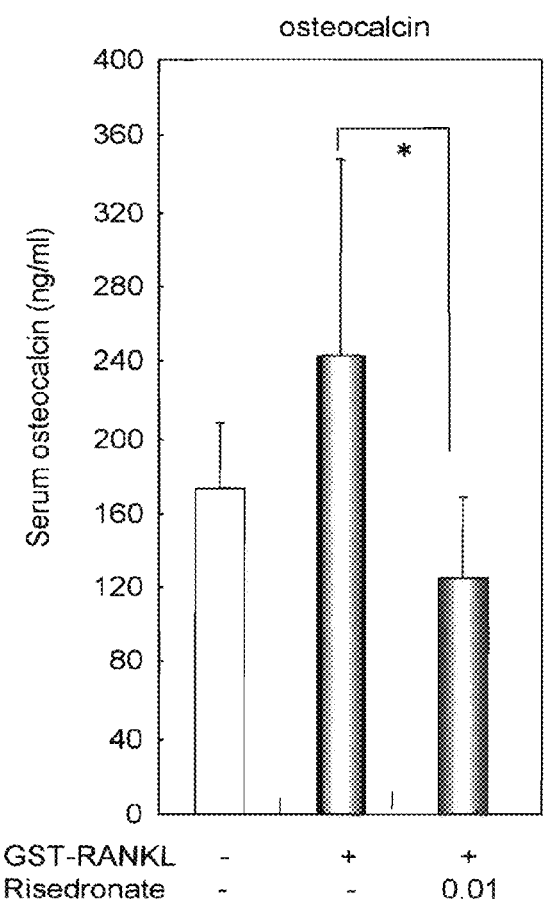
FIG. 20 shows a graph of serum osteocalcin concentrations in osteopenia model mice produced by GST-RANKL administration and subjected to risedronate administration.

The TRAP-5b concentration serving as a bone resorption marker significantly increased in the GST-RANKL administration group to approximately 1.5-fold as high as that for the control group ($P<0.01$). The CTx concentration significantly increased to approximately 1.4-fold as high ($p<0.05$). However, the TRAP-5b and CTx concentrations decreased by approximately 30% in the group subjected to administration of a combination of GST-RANKL and risedronate compared with those for the control group (FIGS. 17 and 18). It was thought that risedronate suppressed osteoclasts naturally existing in mice, resulting in such decreases in the group subjected to administration of a combination of GST-RANKL and risedronate. In addition, the alkaline phosphatase and osteocalcin concentrations serving as osteogenesis markers did not change in the GST-RANKL administration group and the group subjected to administration of a combination of GST-RANKL and risedronate, compared with those for the control group (FIGS. 19 and 20).

Figure 21:
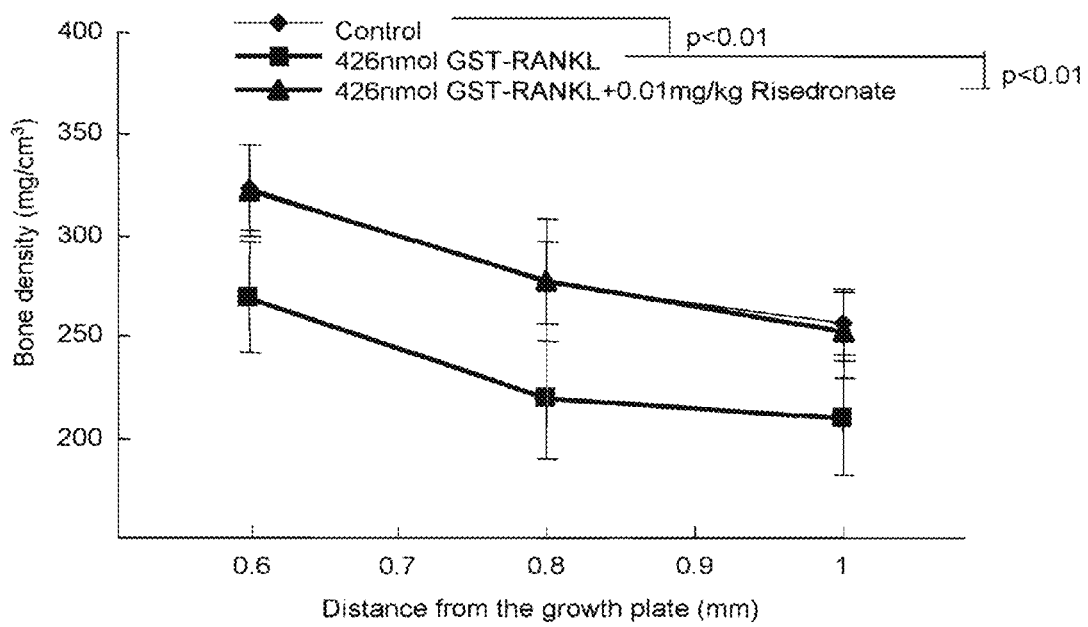
FIG. 21 shows a graph of femur bone densities in osteopenia model mice produced by GST-RANKL administration and subjected to risedronate administration.
Figure 22:
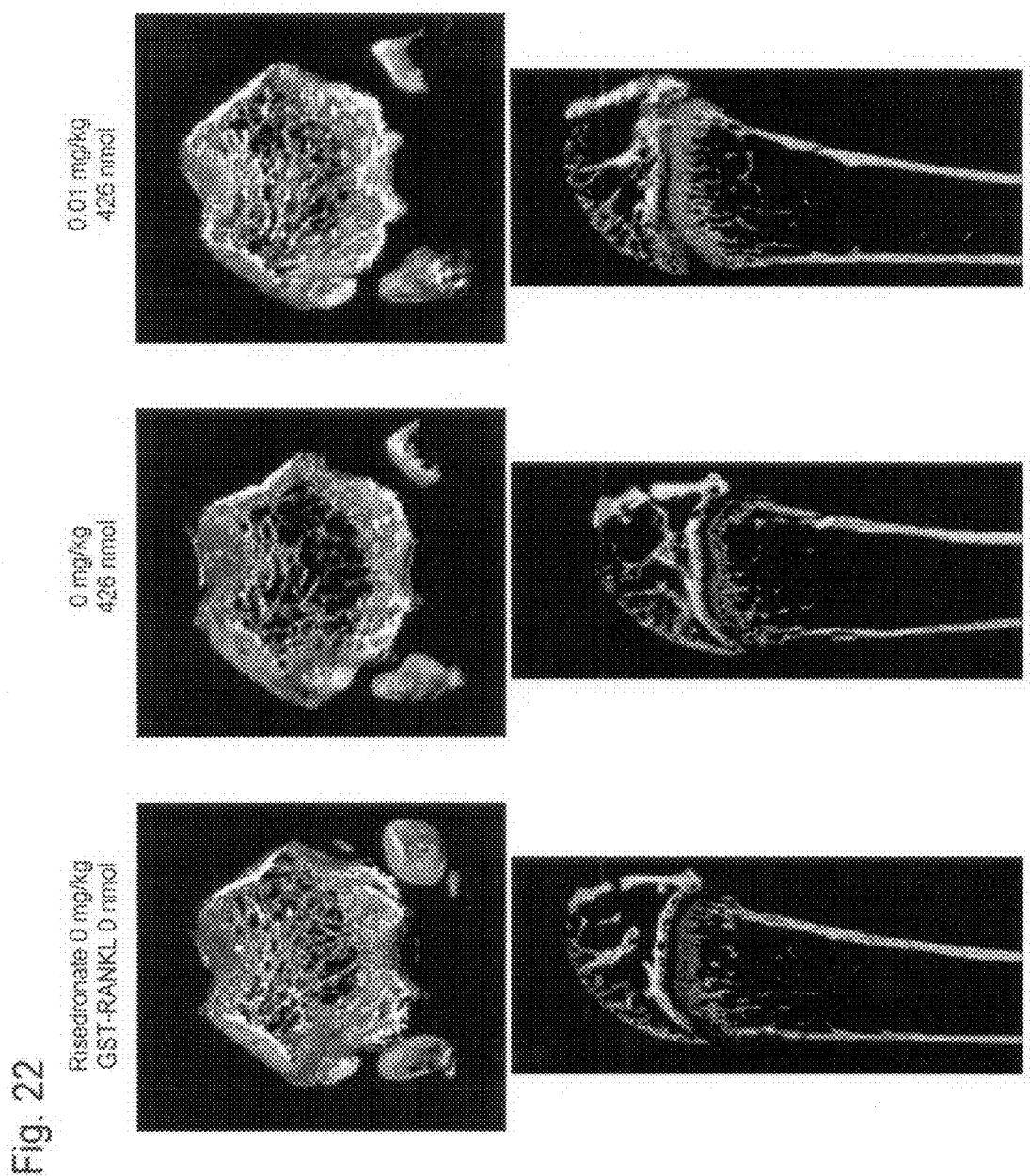
FIG. 22 shows bone morphology images (obtained with micro CT) of the femurs of osteopenia model mice produced by GST-RANKL administration and subjected to risedronate administration.

The bone density for the GST-RANKL administration group significantly decreased compared with that for the control group; the bone density significantly decreased by approximately 20% at the points 0.6 mm, 0.8 mm, and 1.0 mm from the distal growth plate on the proximal side ($p<0.01$). The bone density for the group subjected to administration of a combination of GST-RANKL and risedronate was comparable to that for the control group. Also, similar results were confirmed by image analysis with the use of micro CT. FIG. 21 shows the femur bone density. FIG. 22 shows bone morphology measured with micro CT.

The above results indicate that new therapeutic agents can be evaluated by administering therapeutic agents for osteoporosis and osteopenia to the above mouse models, and that the time period for such evaluation can be shortened by several weeks and the doses used can be significantly decreased compared with the case of drug evaluation with the use of conventional osteopenia mouse models produced by OVX or the like.

Example 4

Production of Osteopenia Model Mice with the Use of Soluble RANKL

Figure 23:
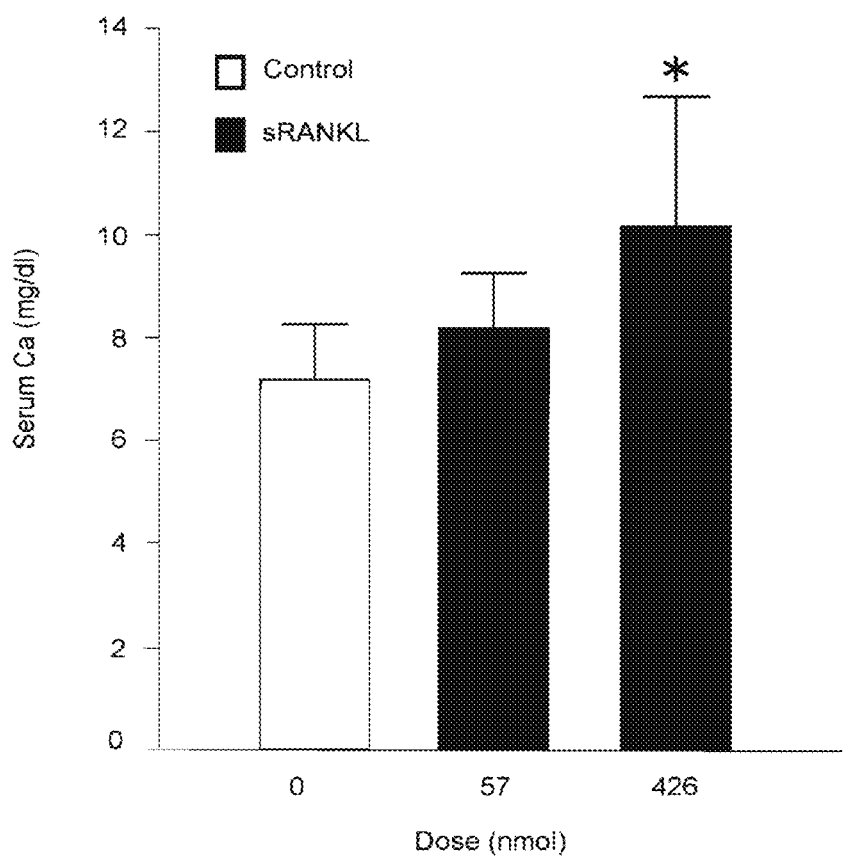
FIG. 23 shows a graph of serum Ca concentrations in mice subjected to administration of soluble RANKL and mice not subjected to administration of the same.
Figure 24:
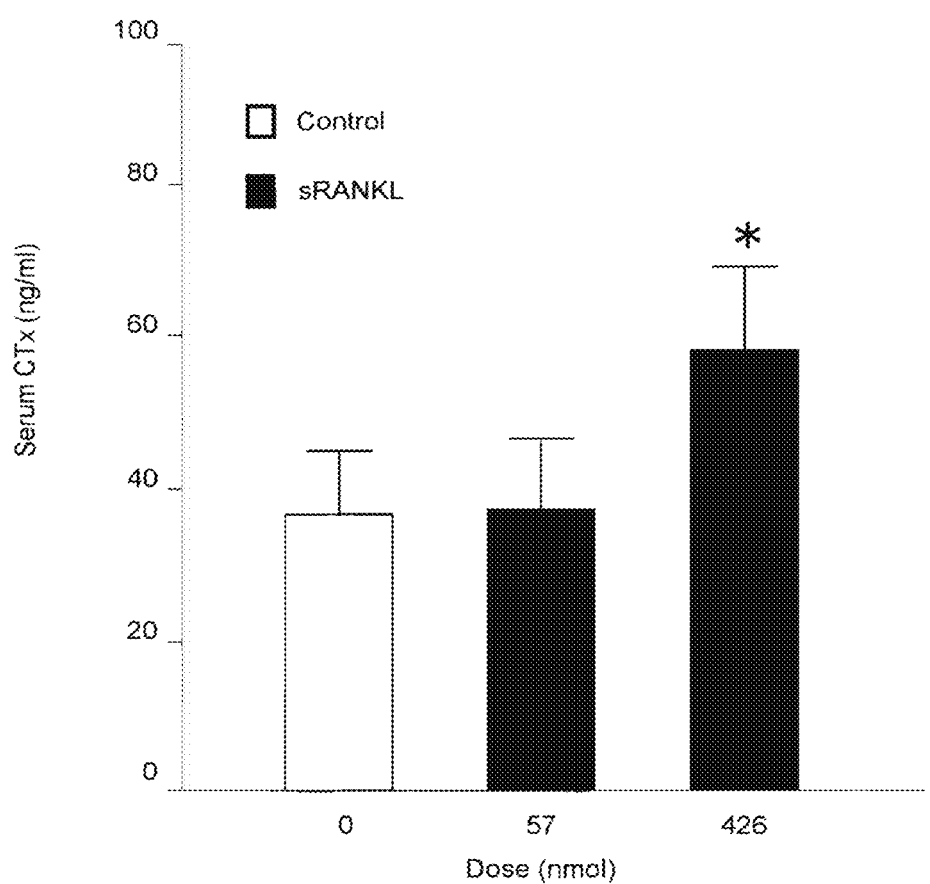
FIG. 24 shows a graph of serum CTx concentrations in mice subjected to administration of soluble RANKL and mice not subjected to administration of the same.
Figure 25:
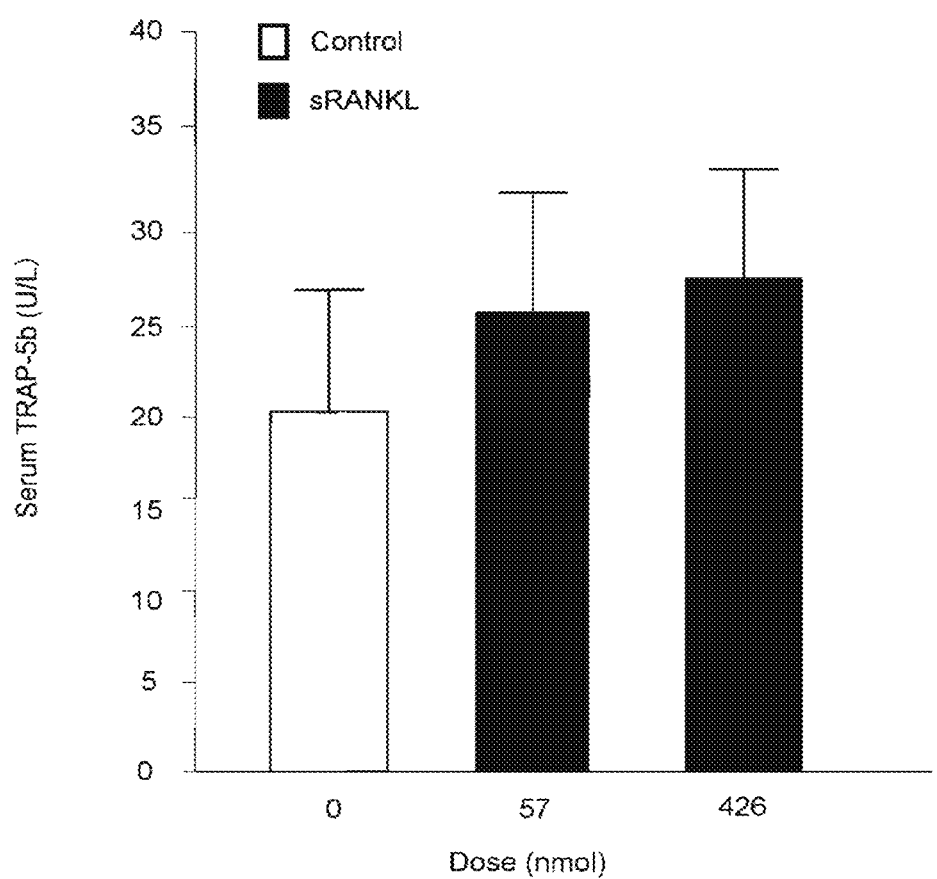
FIG. 25 shows a graph of serum TRAP-5b concentrations in mice subjected to administration of soluble RANKL and mice not subjected to administration of the same.
Figure 26:
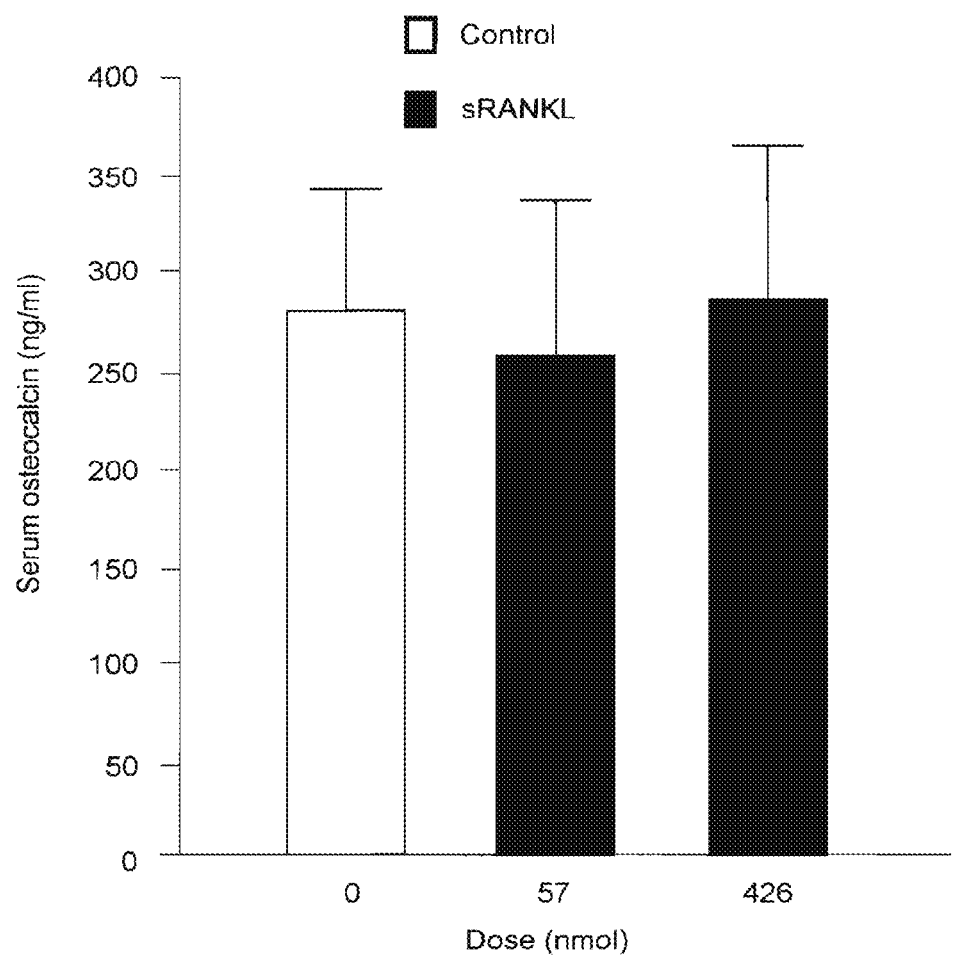
FIG. 26 shows a graph of serum osteocalcin concentrations in mice subjected to administration of soluble RANKL and mice not subjected to administration of the same.
Figure 27:
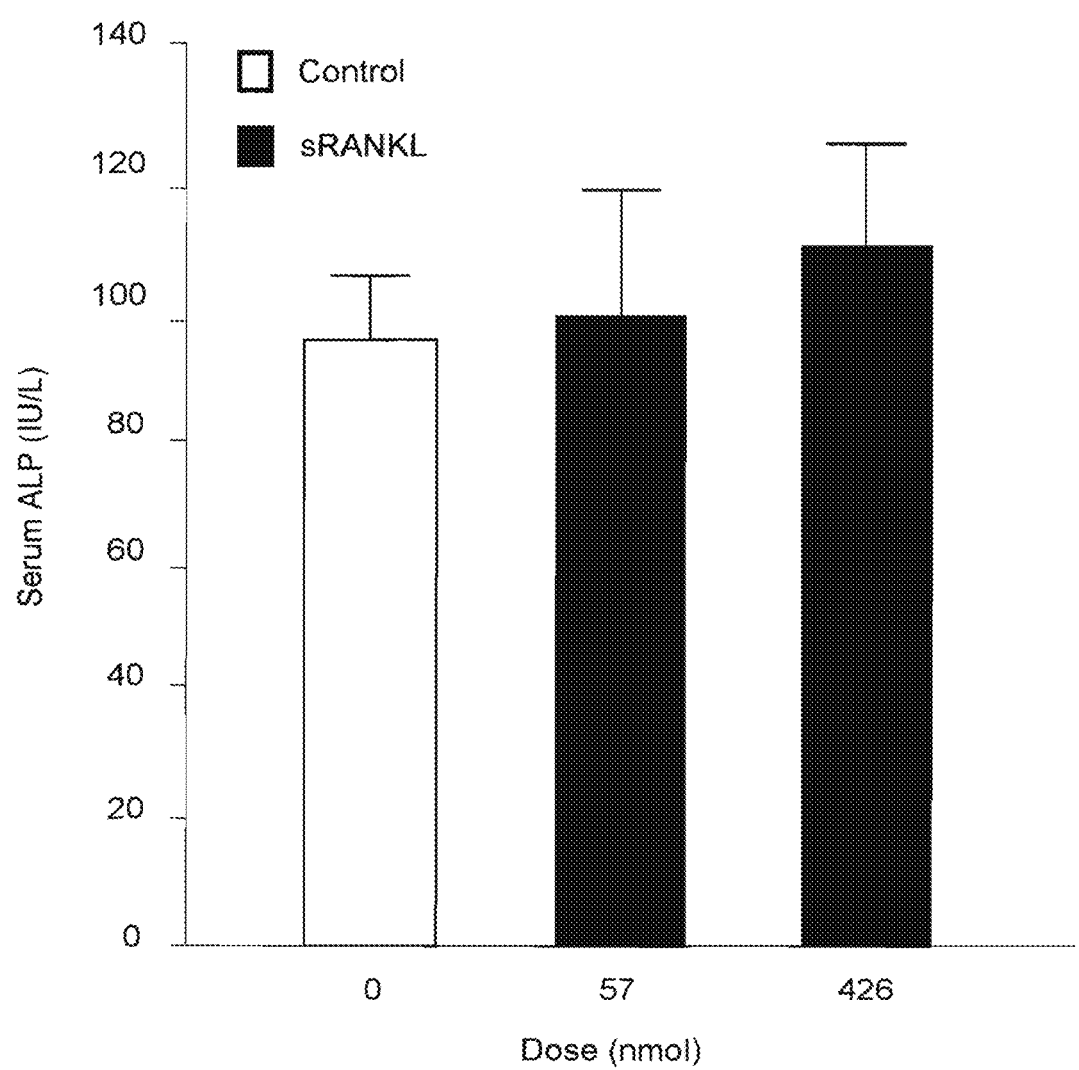
FIG. 27 shows a graph of serum ALP concentrations in mice subjected to administration of soluble RANKL and mice not subjected to administration of the same.
Figure 28:
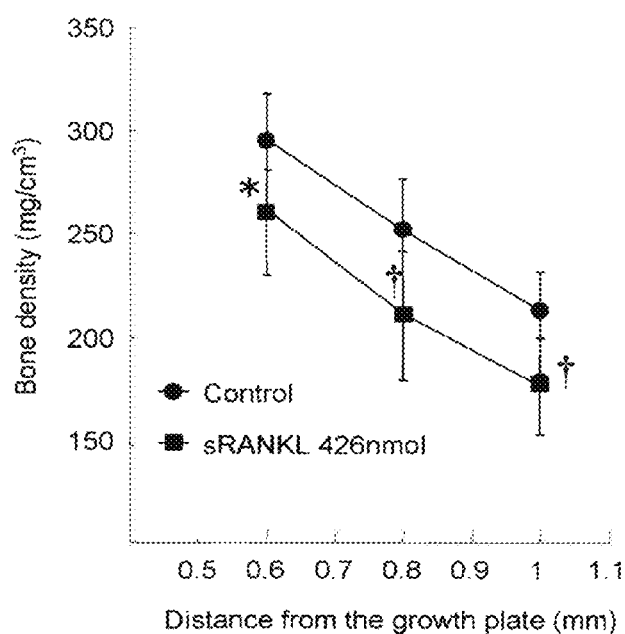
FIG. 28 shows a graph of femur bone densities in mice subjected to administration of soluble RANKL and mice not subjected to administration of the same.

Soluble RANKL (produced by Peprotech) was intraperitoneally administered 3 times to groups of 7-week-old female C57BL/6N mice (10 individuals each) at doses of 57 and 426 nmol every 24 hours. The serum and femur were collected from each mouse 1.5 hours after the $3^{rd}$ administration. Bone resorption markers and osteogenesis markers in the serum were measured. The bone density was measured with the use of pQCT at points 0.6, 0.8, and 1.0 mm from the distal growth plate on the proximal side of the femur. As a result of 426-nmol high-dose administration, the serum calcium and CTx concentrations serving as bone resorption markers significantly increased, respectively, to approximately 1.4-fold and 1.5-fold as high (FIGS. 23 and 24). The TRAP-5b concentration tended to increase to approximately 1.25-fold as high, although no significant difference was observed (FIG. 25). In addition, the osteocalcin and alkaline phosphatase concentrations serving as osteogenesis markers did not vary (FIGS. 26 and 27). The femur bone density significantly decreased by approximately 20% (FIG. 28).

Based on the above results, the technique of producing an osteopenia mouse model can be carried out with the use of any type of soluble RANKL, not with the specific use of GST-RANKL. Thus, it is considered that soluble RANKL can be used for drug evaluation, as in the case of GST-RANKL.

Example 5

Evaluation of Osteopenia Model Mice

Morphology Measurement

Figure 29:
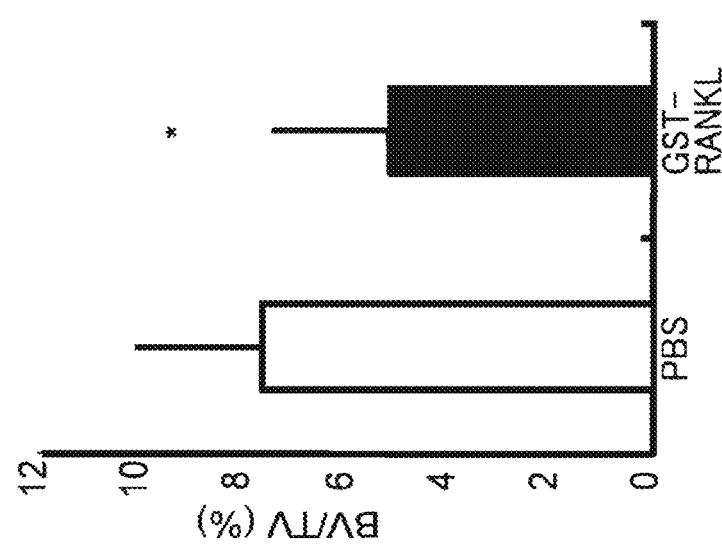
FIG. 29 shows a graph of unit bone masses in mice subjected to administration of GST-RANKL and mice subjected to administration of PBS.
Figure 30:
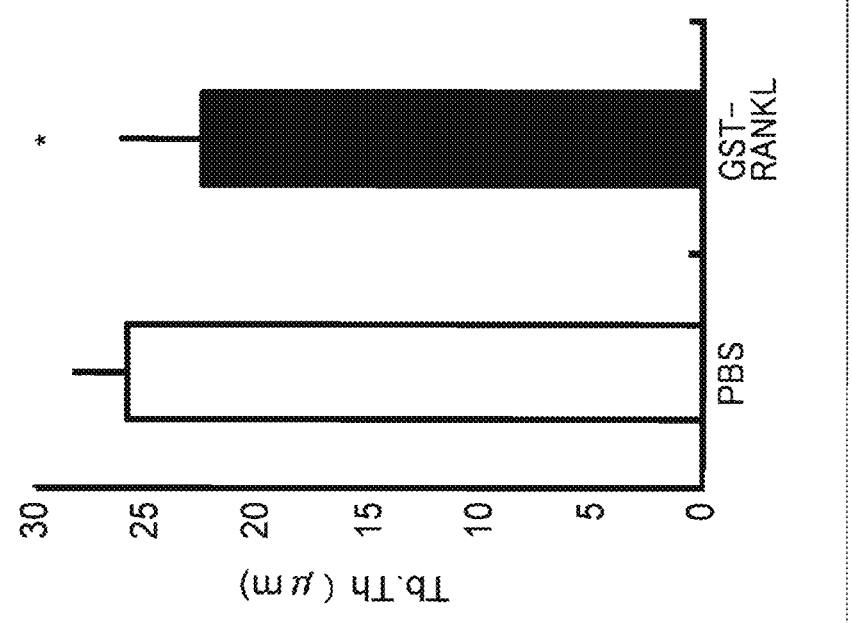
FIG. 30 shows a graph of trabecular widths in mice subjected to administration of GST-RANKL and mice subjected to administration of PBS.
Figure 31:
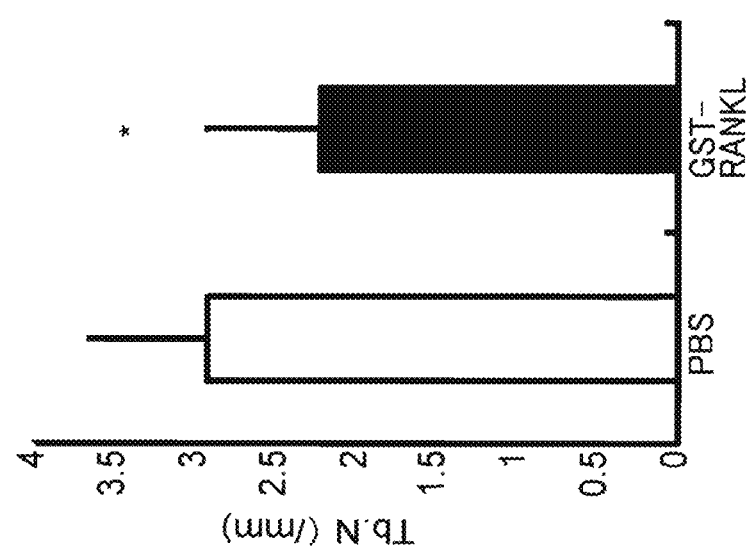
FIG. 31 shows a graph of trabecular numbers in mice subjected to administration of GST-RANKL and mice subjected to administration of PBS.
Figure 32:
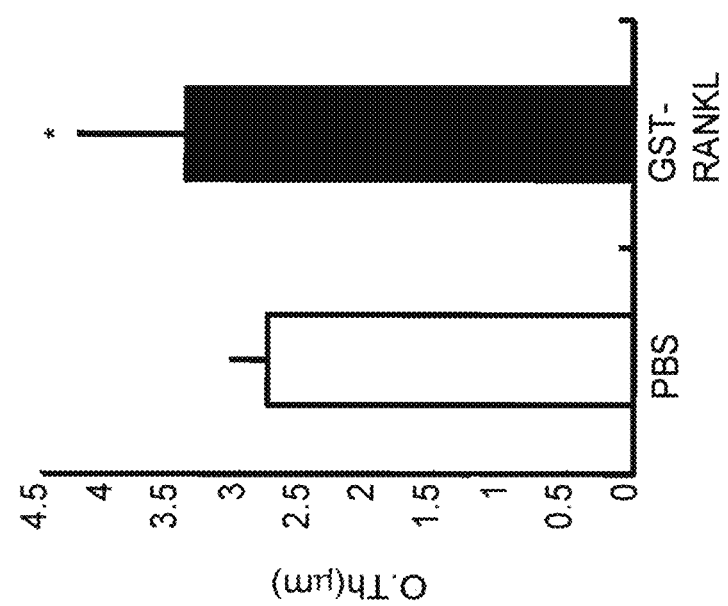
FIG. 32 shows a graph of osteoid thicknesses in mice subjected to administration of GST-RANKL and mice subjected to administration of PBS.
Figure 33:
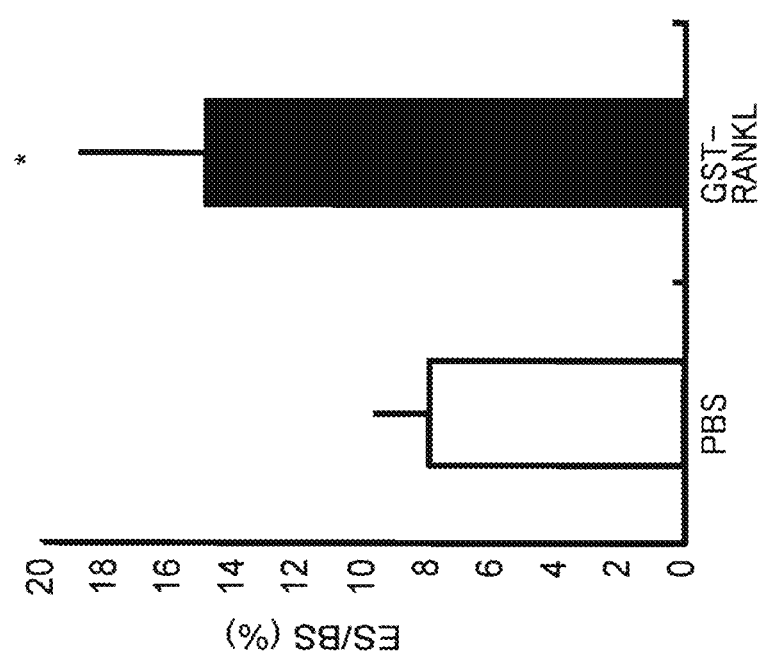
FIG. 33 shows a graph of eroded surface areas for mice subjected to administration of GST-RANKL and mice subjected to administration of PBS.
Figure 34:
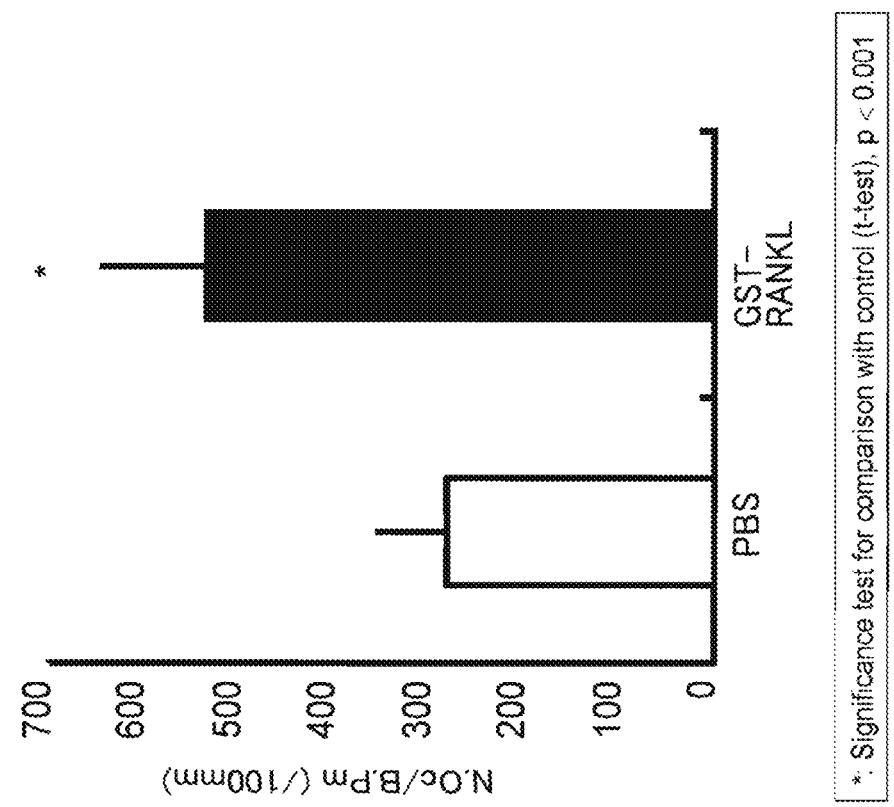
FIG. 34 shows a graph of the osteoclast numbers in mice subjected to administration of GST-RANKL and mice subjected to administration of PBS.
Figure 35:
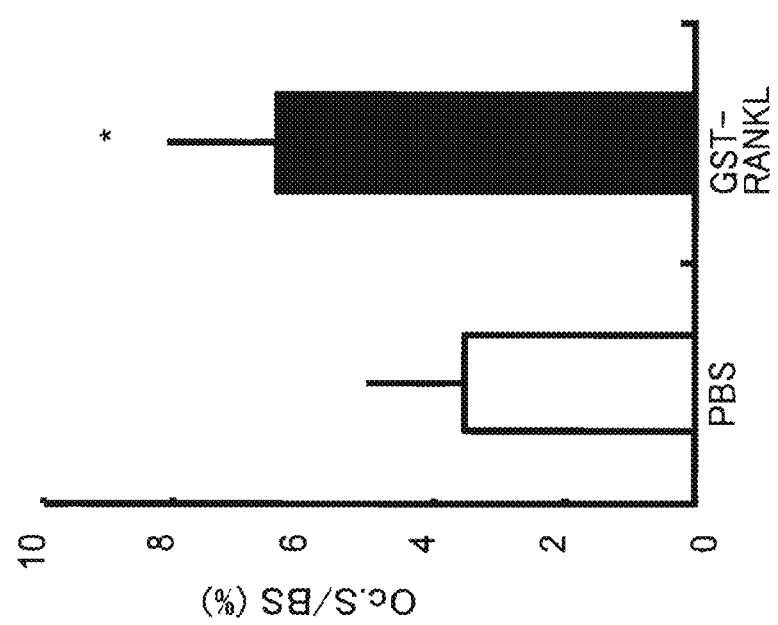
FIG. 35 shows a graph of osteoclast surface areas for mice subjected to administration of GST-RANKL and mice subjected to administration of PBS.
Figure 36:
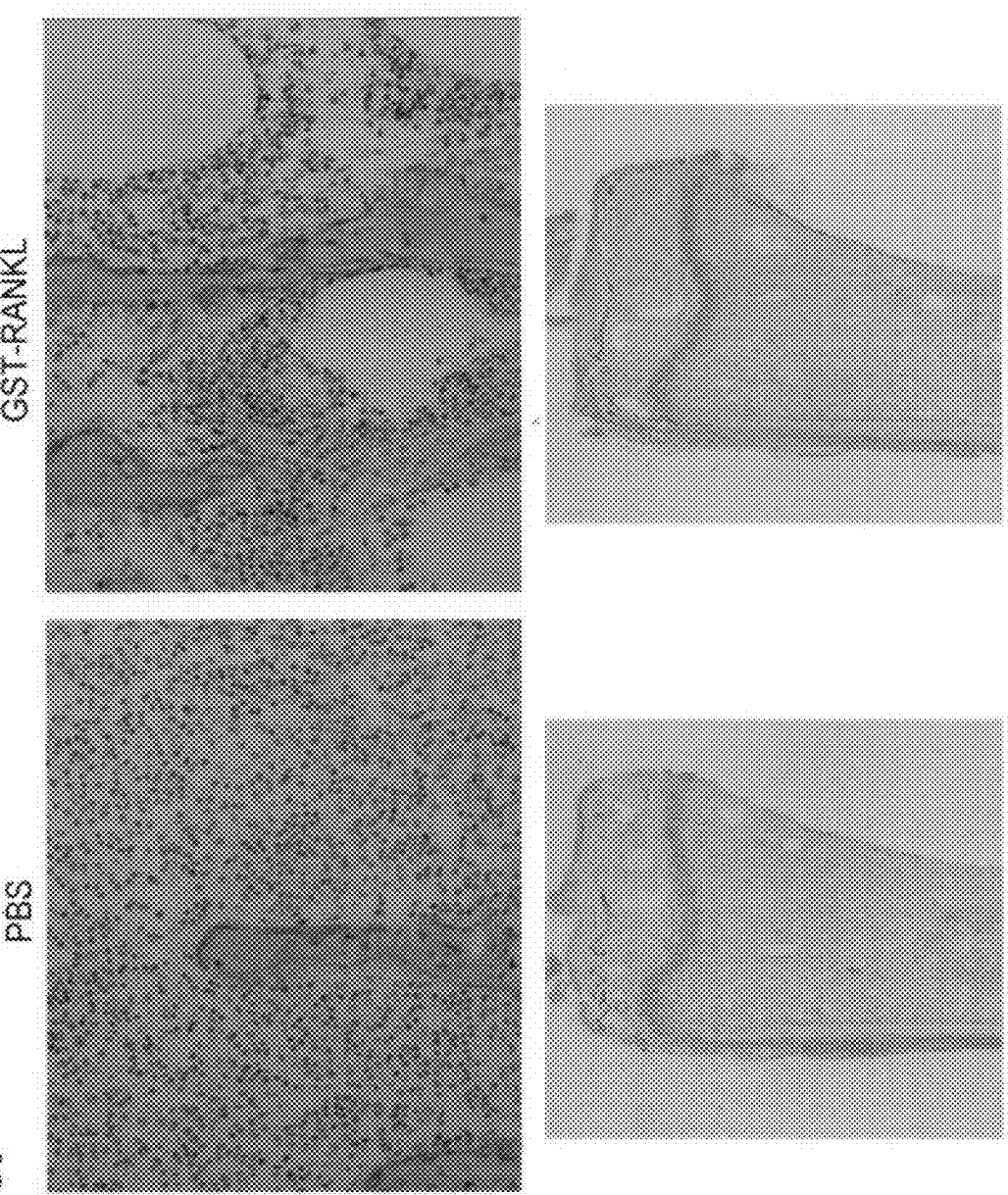
FIG. 36 shows TRAP staining images indicating osteoclast increases in mice subjected to administration of GST-RANKL and mice subjected to administration of PBS.

GST-RANKL was intraperitoneally administered 3 times to groups of 7-week-old female C57BL/6N mice at 2 mg/kg every 24 hours, followed by dissection. The tibia of each mouse was subjected to toluidine blue staining and morphology measurement. A solvent (PBS) was administered to the control group in the same manner as above. The GST-RANKL intraperitoneal administration group was subjected to tibial bone morphology measurement. The unit bone mass (BV/TV), the trabecular width (Tb.Th), and the trabecular number (Tb.N) decreased by approximately 30% (p<0.03), approximately 10% (P<0.03), and approximately 20% (p<0.05), respectively, compared with those for the control group (FIGS. 29 to 31). In addition, the osteoid thickness (O.Th), the eroded surface area (ES/BS), the osteoclast number (N.Oc/B.Pm), and the osteoclast surface area (Oc.S/BS) increased, respectively, to approximately 1.2-fold (p<0.04), approximately 1.8-fold (p<0.001), approximately 1.9-fold (p<0.001), and approximately 1.8-fold (p<0.001) as high as those for the control group (FIGS. 32 to 35). In addition, the sections obtained in this Example were subjected to TRAP staining. Accordingly, the osteoclast number observed was greater than that for the control group (FIG. 36). The results revealed that a bone mass decrease can be evaluated based on the osteoclast number, the osteoclast surface area, and the like obtained by bone morphology measurement, in addition to the serum and the bone density. Further, although the osteoid thickness significantly increased in the case of GST-RANKL administration, no increase in the osteoblast surface area was observed. Meanwhile, significant increases were observed in terms of items representing bone resorption, including the eroded surface area, the osteoclast number, and the osteoclast surface area. Accordingly, it was found that GST-RANKL did not act on osteoblasts but directly induced osteoclast differentiation and activation so as to cause osteopenia. That is, the osteopenia mechanism induced by GST-RANKL administration involves promotion of bone resorption, but not reduction in osteogenesis. However, the aforementioned coupling phenomenon causes promotion of osteogenesis depending on the GST-RANKL dose, the number of doses, and the period of time elapsed after administration, which might results in an increase in the osteoblast surface area.

Examination of Drug Evaluation with the Use of Bisphosphonate (Risedronate)

Risedronate was separately administered via a subcutaneous route to groups of 7-week-old female C57BL/6 mice at doses of 3, 10, and 30 µg/kg every 24 hours from the day before GST-RANKL administration to the end of the experimentation. The femur and serum were collected from each mouse 1.5 hours after the $3^{rd}$ administration of GST-RANKL. Measurement of TRAP-5b, calcium (Ca), and alkaline phosphatase (ALP) was carried out. Each femur was subjected to bone density measurement and image analysis with the use of pQCT.

Figure 37:
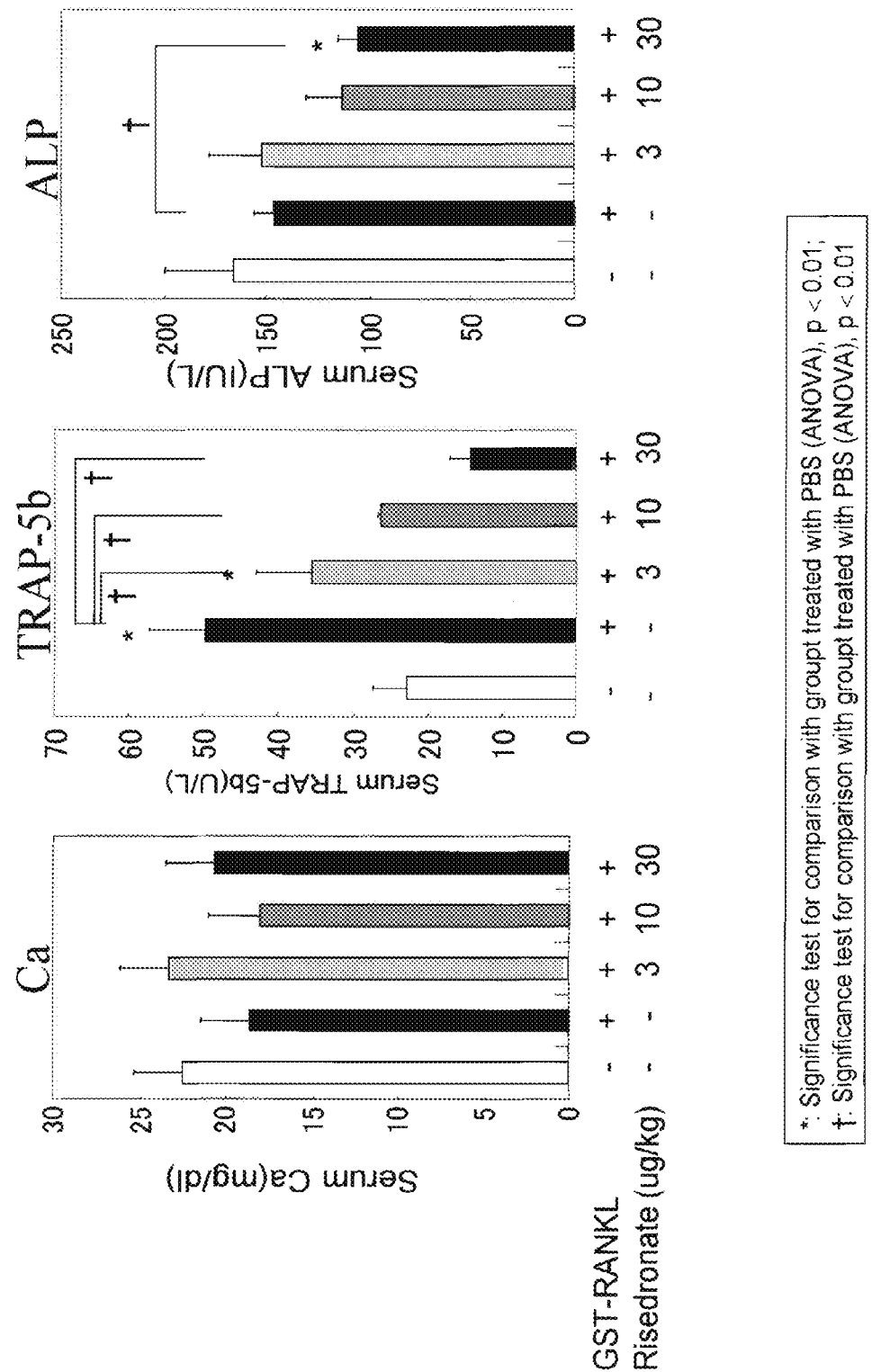
FIG. 37 shows graphs of serum Ca, TRAP-5b, and ALP concentrations in mice subjected to administration of GST-RANKL and then subjected to administration of risedronate.
Figure 38:
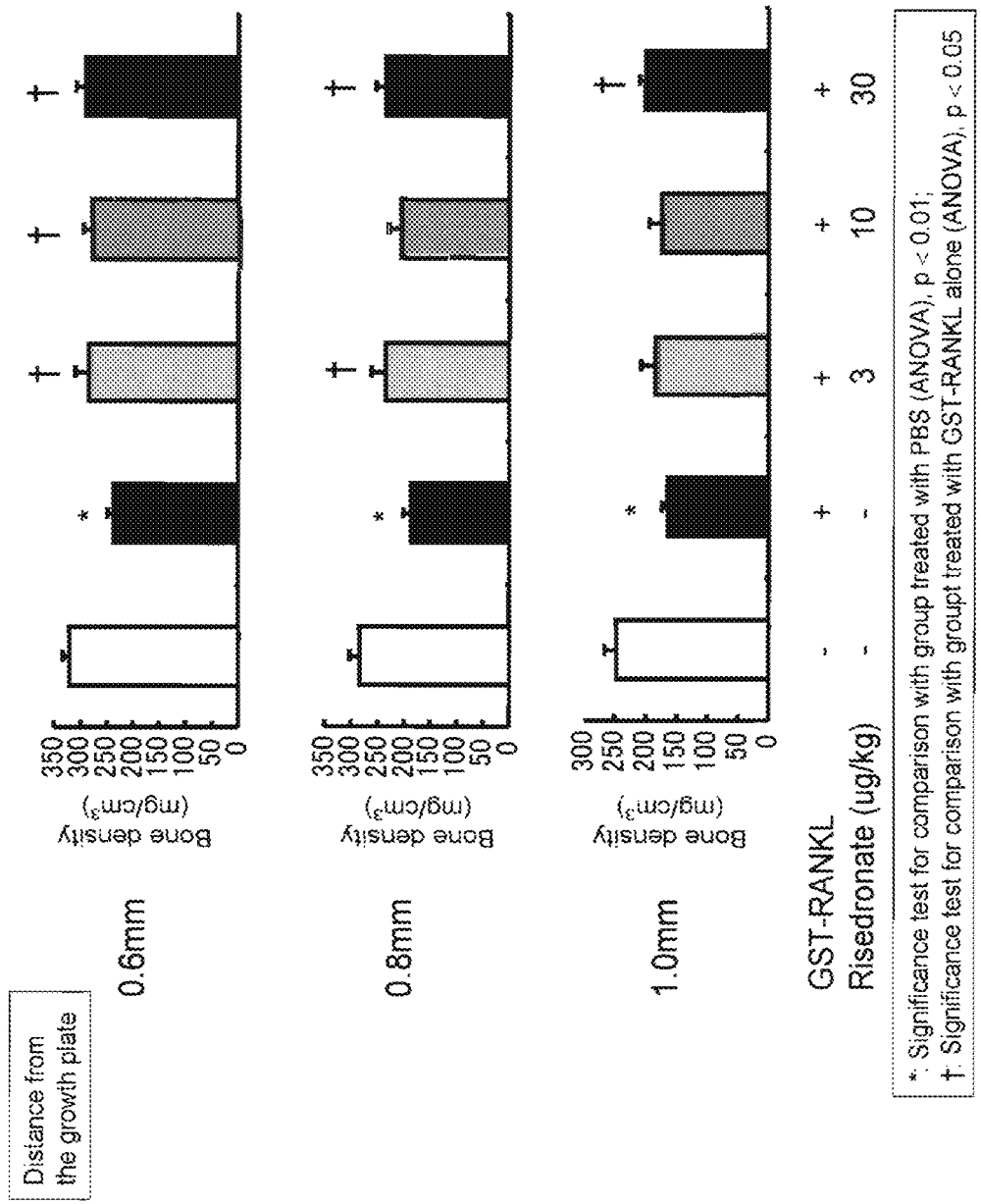
FIG. 38 shows graphs of bone densities in mice subjected to administration of GST-RANKL and then subjected to administration of risedronate.
Figure 39:
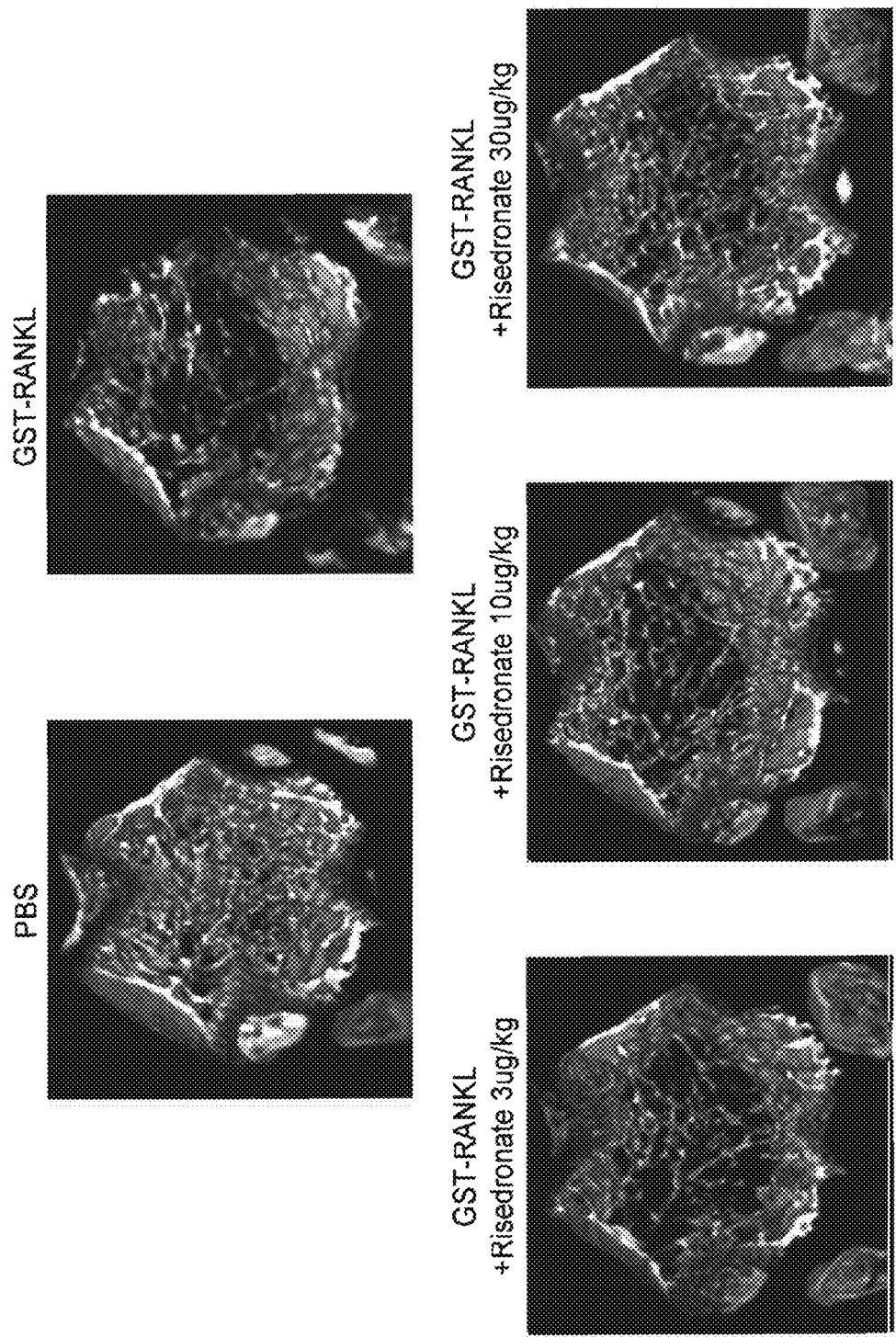
FIG. 39 shows images indicating image analysis results (obtained with micro CT) for mice subjected to administration of GST-RANKL and then subjected to administration of risedronate.

The Ca concentration did not obviously vary. However, the TRAP-5b concentration significantly increased to approximately 2-fold as high, as a result of RANKL administration (p<0.01). The TRAP-5b concentration increased in the above case decreased by approximately 30% (p<0.01), 50% (p<0.01), and 70% (p<0.01) in a dose-dependent manner upon risedronate administration, compared with that for the group subjected to administration of RANKL alone. In addition, the ALP concentration significantly decreased as a result of administration of risedronate at 30 µg/kg (p<0.01) compared with that for the group subjected to administration of RANKL alone (FIG. 37). The bone density was measured at points 0.6, 0.8, and 1.0 mm from the distal growth plate on the proximal side of the femur with the use of pQCT. The bone density decreased in the RANKL administration group by 27% (p<0.01), 35% (p<0.01), and 35% (p<0.01) at the above measurement points, compared with that for the PBS administration group. Such bone density decreases were suppressed to: 12% (p<0.05), 18% (p<0.05), and 24% (at the 0.6-, 0.8-, and 1.0-mm points, respectively); 13% (p<0.05), 28%, and 30% (at the 0.6-, 0.8-, and 1.0-mm points, respectively); and 10% (p<0.05), 18% (p<0.05), and 20% (p<0.05) (at the 0.6-, 0.8-, and 1.0-mm points, respectively) as a result of administration of risedronate at 3 µg/kg, 10 µg/kg, and 30 µg/kg, respectively (FIG. 38). Also, similar results were confirmed by image analysis with the use of micro CT (FIG. 39).

Examination of Drug Evaluation Involving Comparison of a Plurality of Bisphosphonates Etidronate, alendronate, and risedronate were separately administered 3 times via a subcutaneous route at doses of 3 and 30 mg/kg, at doses of 3, 30, and 300 µg/kg, and at doses of 1, 10, and 100 µg/kg, respectively, to groups of 7-week-old female C57BL/6 mice for every 24 hours from the day before GST-RANKL administration to the end of the experimentation. GST-RANKL was intraperitoneally administered 3 times at 1 mg/kg every 24 hours. The femur, tibia, and serum were collected from each mouse 1.5 hours after the $3^{rd}$ GST-RANKL administration. Measurement of TRAP-5b, calcium (Ca), and alkaline phosphatase (ALP) in the serum was carried out. Each femur was subjected to bone density measurement with pQCT and image analysis with micro CT.

Figure 40:
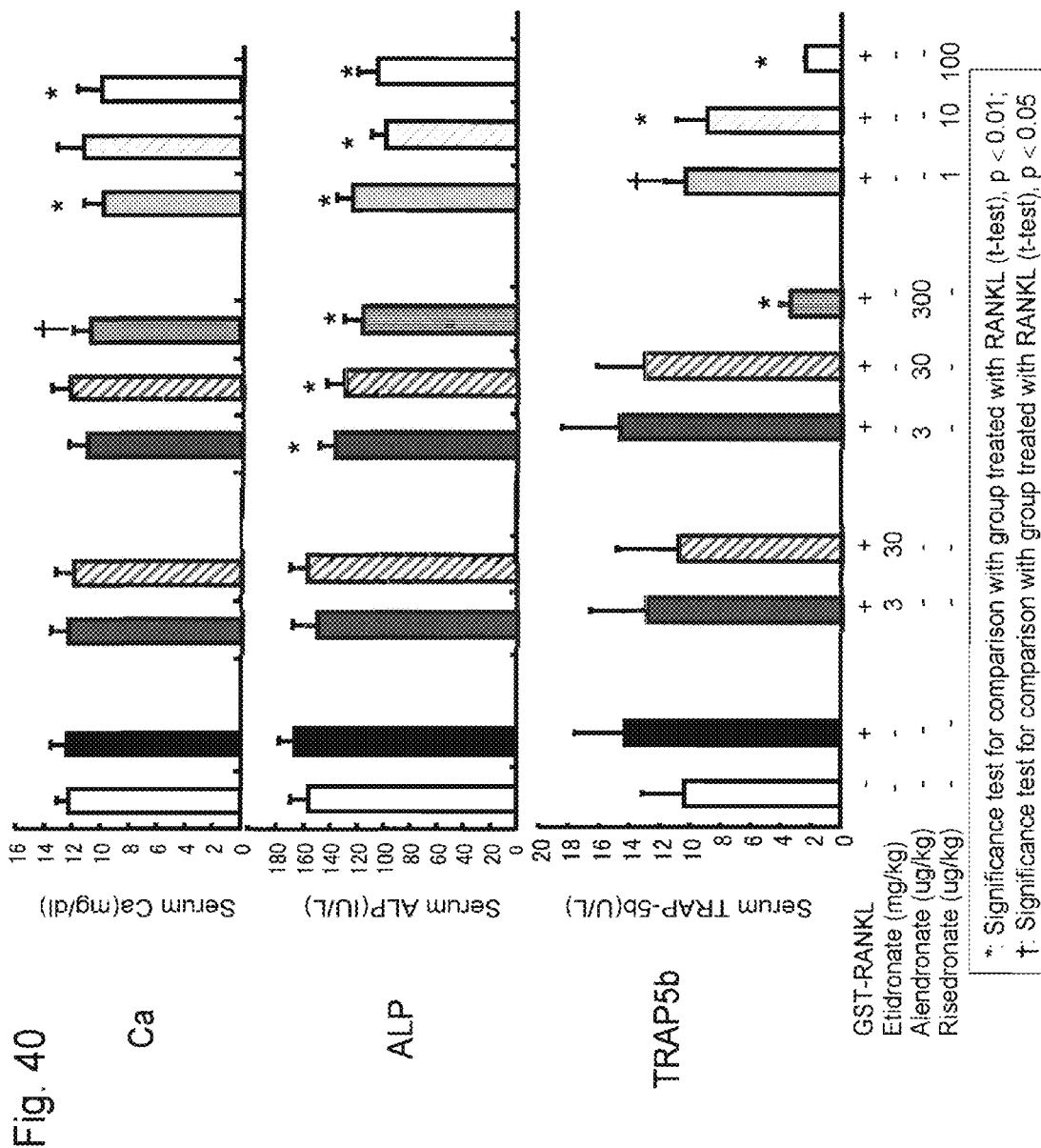
FIG. 40 shows graphs of serum Ca, ALP, and TRAP-5b concentrations in mice subjected to administration of GST-RANKL and then subjected to administration of etidronate, alendronate, or risedronate.

The Ca concentration significantly decreased in the case of administration of alendronate at 300 µg/kg and in the case of administration of risedronate at 1 and 100 µg/kg (p<0.05, p<0.01, and p<0.01, respectively) compared with the case of RANKL administration (FIG. 40).

Figure 41:
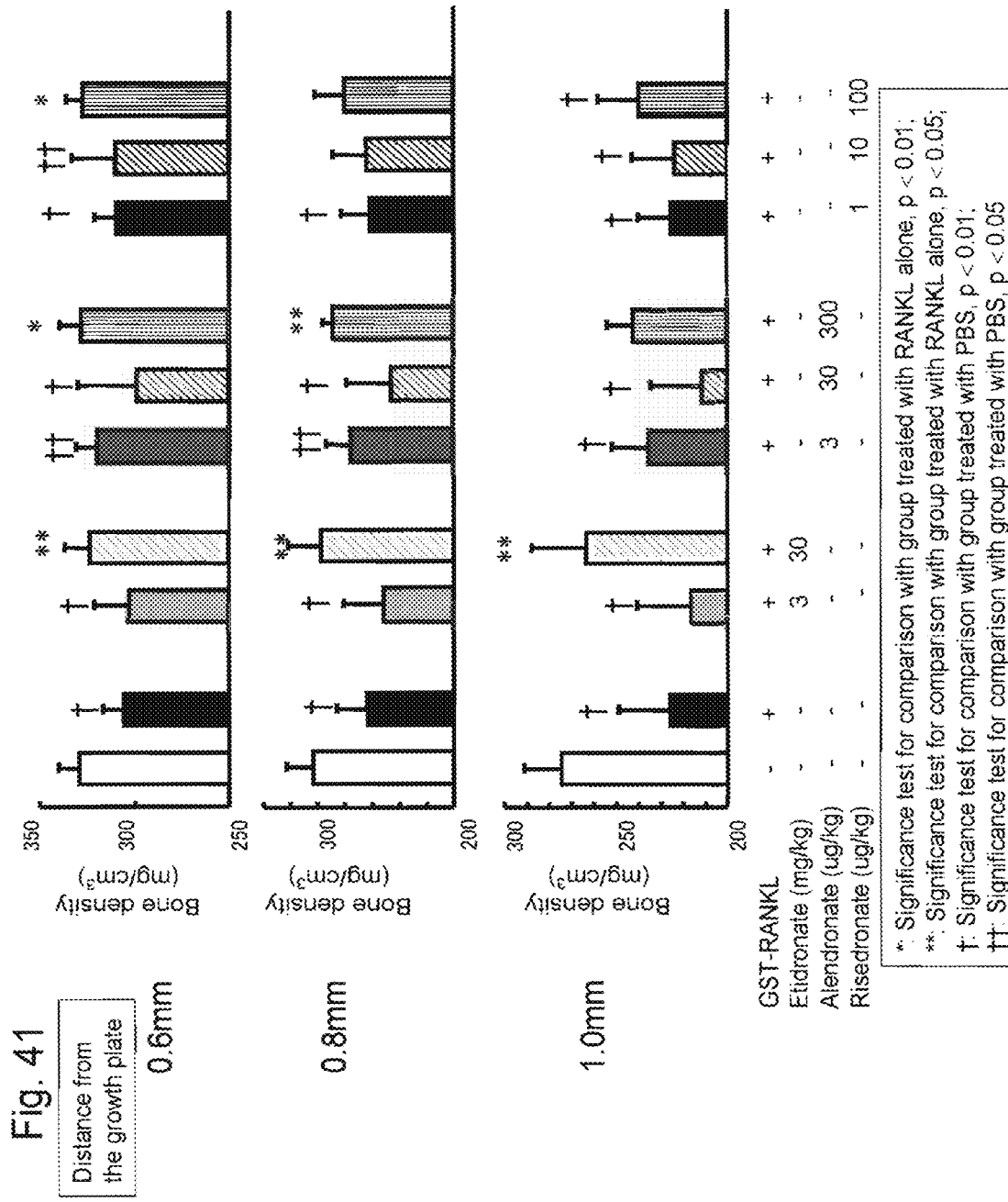
FIG. 41 shows graphs of bone densities in mice subjected to administration of GST-RANKL and then subjected to administration of etidronate, alendronate, or risedronate.
Figure 42:
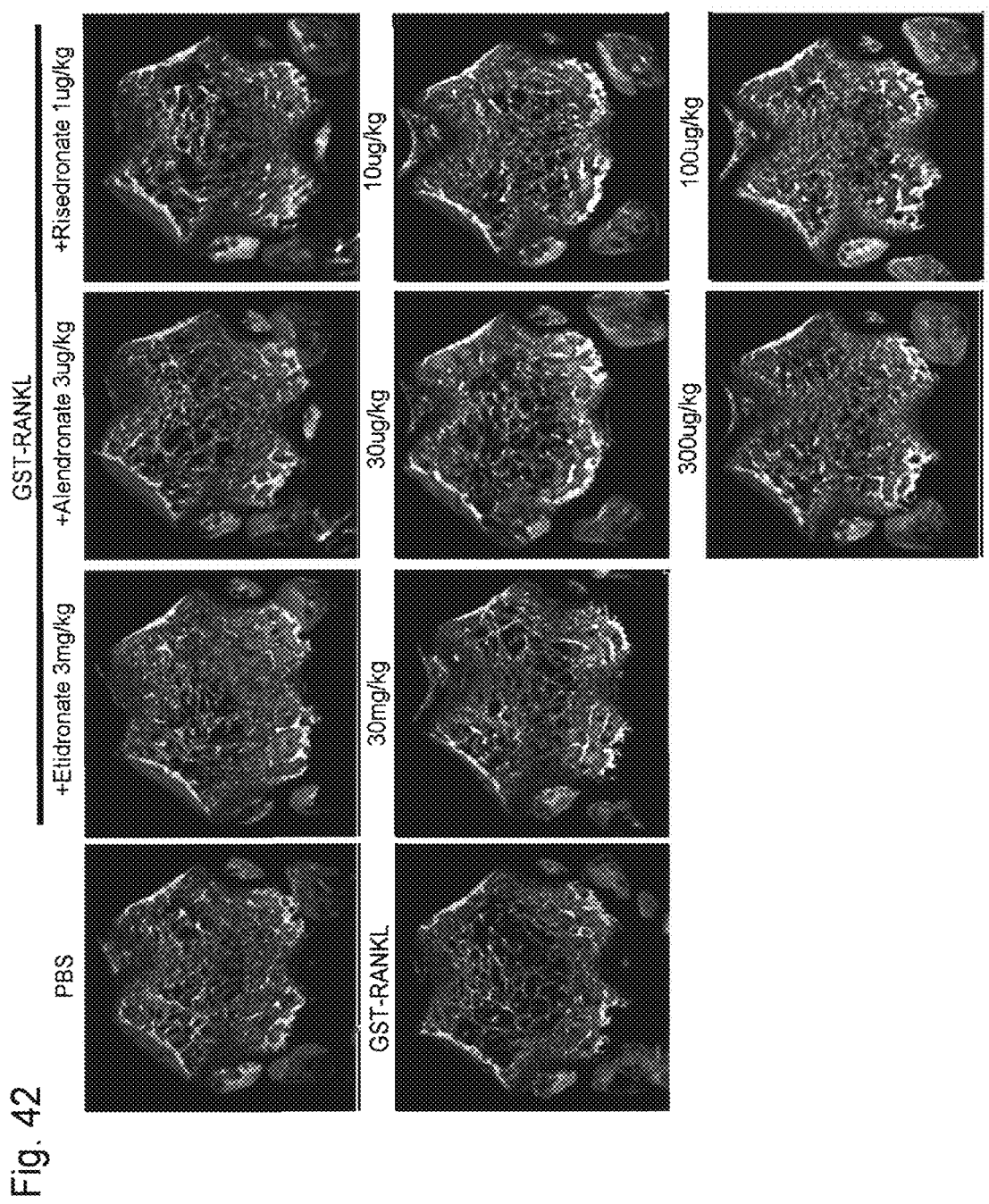
FIG. 42 shows images indicating image analysis results (obtained with micro CT) for mice subjected to administration of GST-RANKL and then subjected to administration of etidronate, alendronate, or risedronate.

The TRAP-5b concentration increased by approximately 40% in the case of RANKL administration; however, no significant difference was obtained. An increase in the TRAP-5b concentration was significantly suppressed by administration of alendronate at a dose of 300 μg/kg (p<0.01). In addition, an increase in the TRAP-5b concentration was significantly suppressed by administration of risedronate at doses of 1, 10, and 100 μg/kg (p<0.05, p<0.01, and p<0.01, respectively) (FIG. 40). The ALP concentration was found to decrease by approximately 20% to 30% (p<0.01) in a dose-dependent manner in the case of alendronate administration and in the case of risedronate administration compared with that for the RANKL administration group (FIG. 40). The bone density was measured with pQCT at points 0.6, 0.8, and 1.0 mm from the distal growth plate on the proximal side of the femur. The bone density decreased by 7% (p<0.01), 13% (p<0.01), and 18% (p<0.01) at the above points in the RANKL administration group compared with that for the PBS administration group. Such bone density decrease was suppressed to 2% to 4% (p<0.05) at every measurement point by administration of etidronate at 30 mg/kg. Similarly, such decrease was suppressed to 1% (p<0.01) at the 0.6-mm point and 5% (p<0.05) at the 0 8-mm point by administration of alendronate at a dose of 300 μg/kg. Also, in the case of risedronate administration, such decrease was suppressed to 1% (p<0.01) at the 0.6-mm point at a dose of 100 μg/kg (FIG. 41). Similar results were confirmed by image analysis with the use of micro CT (FIG. 42).

Based on the above results, preliminary administration of the $1^{st}$ to $3^{rd}$ generation bisphosphonates was carried out 1 day before RANKL administration such that pharmacological effects thereof could be evaluated. In addition, doses at which the effects were exhibited were 30 mg/kg for etidronate, 300 μg/kg for alendronate, and 100 g/kg for risedronate. The doses reflected the degrees of pharmacological effects of the drugs. The results indicate that an osteopenia model obtained by RANKL administration can be applied to screening for and evaluation of a novel drug with further intensified pharmacological effects. In addition, the time period between preliminary bisphosphonate administration and mouse dissection was as short as 73.5 hours, indicating that evaluation of pharmacological effects, including measurement of bone metabolism markers and bone density, took as short as 4 days. Therefore, such an osteopenia animal model obtained by RANKL administration was found to be applicable to a system for rapid evaluation of a bone resorption suppressant.

Method of Producing OVX Mice in a Short Period of Time 7-week-old female C57BL/6N mice were reared for 25 days. Then, GST-RANKL was intraperitoneally administered twice thereto at 1 mg/kg every 24 hours. Ovariectomy was carried out 24 hours after the $2^{nd}$ administration. Further, the femur, tibia, and serum were collected from each mouse 24 hours after ovariectomy. The obtained samples were compared with the samples obtained from a group that was reared for 4 weeks after ovariectomy. In addition, PBS was administered to control groups for comparison with GST-RANKL administration groups. The PBS administration groups were subjected to sham operation (Sham) for comparison with the groups subjected to ovariectomy.

Regarding bone metabolism markers, TRAP-5b, calcium (Ca), and alkaline phosphatase (ALP) in the serum were measured. Each femur was subjected to bone density measurement with pQCT and image analysis with micro CT. After the initiation of rearing, the date of implementation of OVX or sham operation was expressed as "day X."

Figure 43:
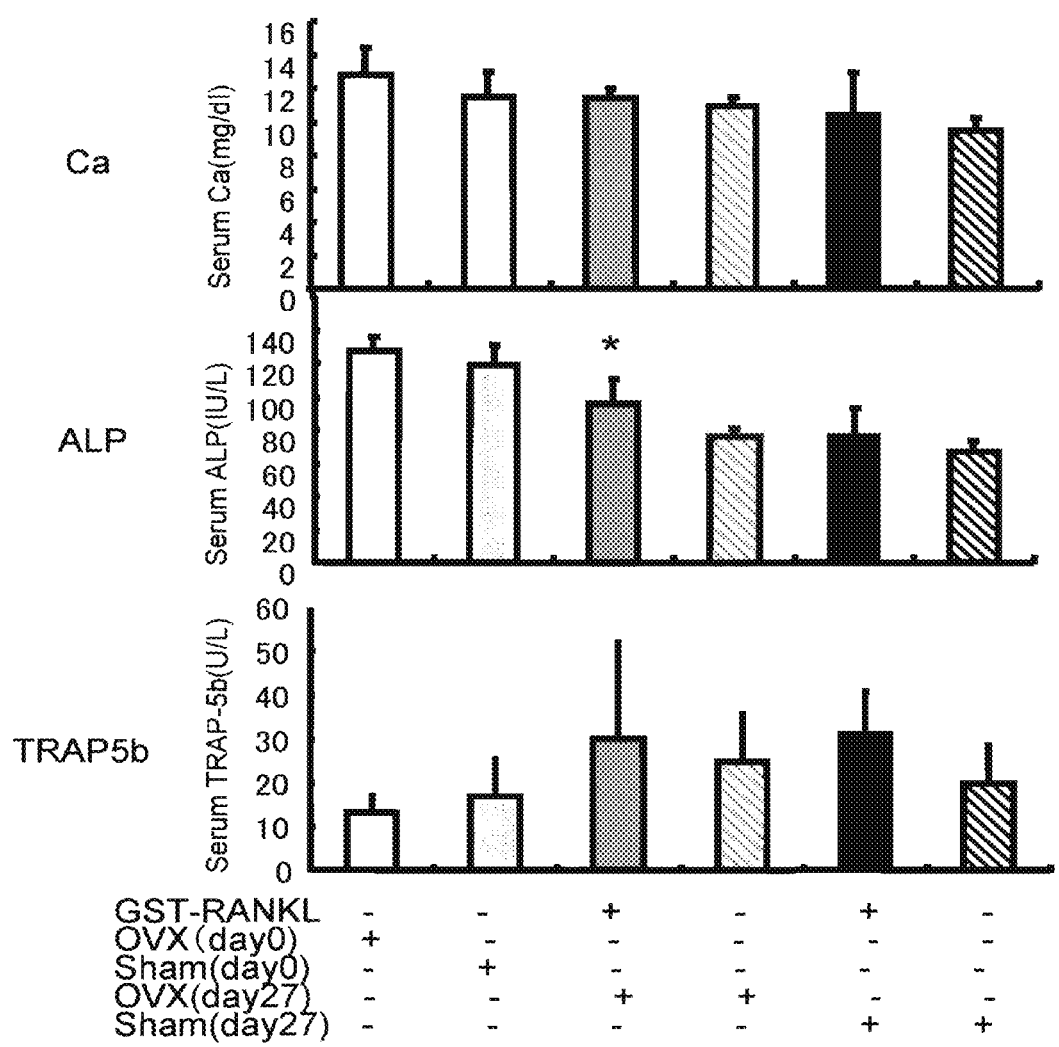
FIG. 43 shows graphs of serum Ca, TRAP-5b, and ALP concentrations in mice subjected to administration of GST-RANKL and then subjected to ovariectomy.

The TRAP-5b concentration for every GST-RANKL administration group increased to approximately 1.8-fold as high as that for the PBS administration+Sham (day 27) group; however, no significant difference was obtained. The Ca concentration for the OVX (day 0) group increased by approximately 11% compared with that for the Sham (day 0) group; however, there were no changes in every OVX treatment group. In addition, regarding the ALP concentration, there were no changes in the Sham (day 0) group or the OVX (day 0) group. The ALP concentration increased in the GST-RANKL administration OVX (day 27) group by approximately 40% (p<0.01) compared with that for the PBS administration+Sham (day 27) group (FIG. 43).

Figure 44:
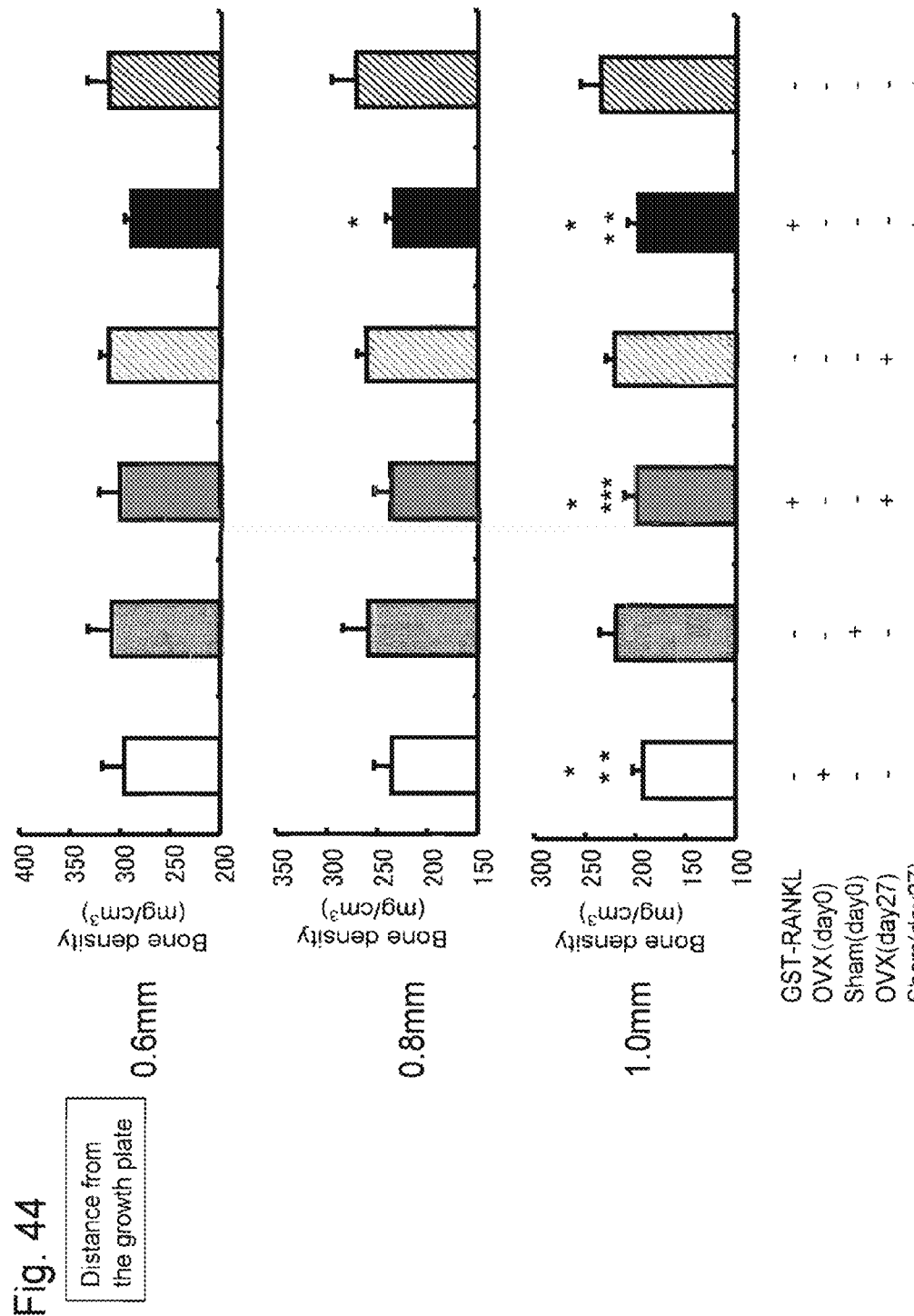
FIG. 44 shows graphs of bone densities in mice subjected to administration of GST-RANKL and then subjected to ovariectomy.
Figure 45:
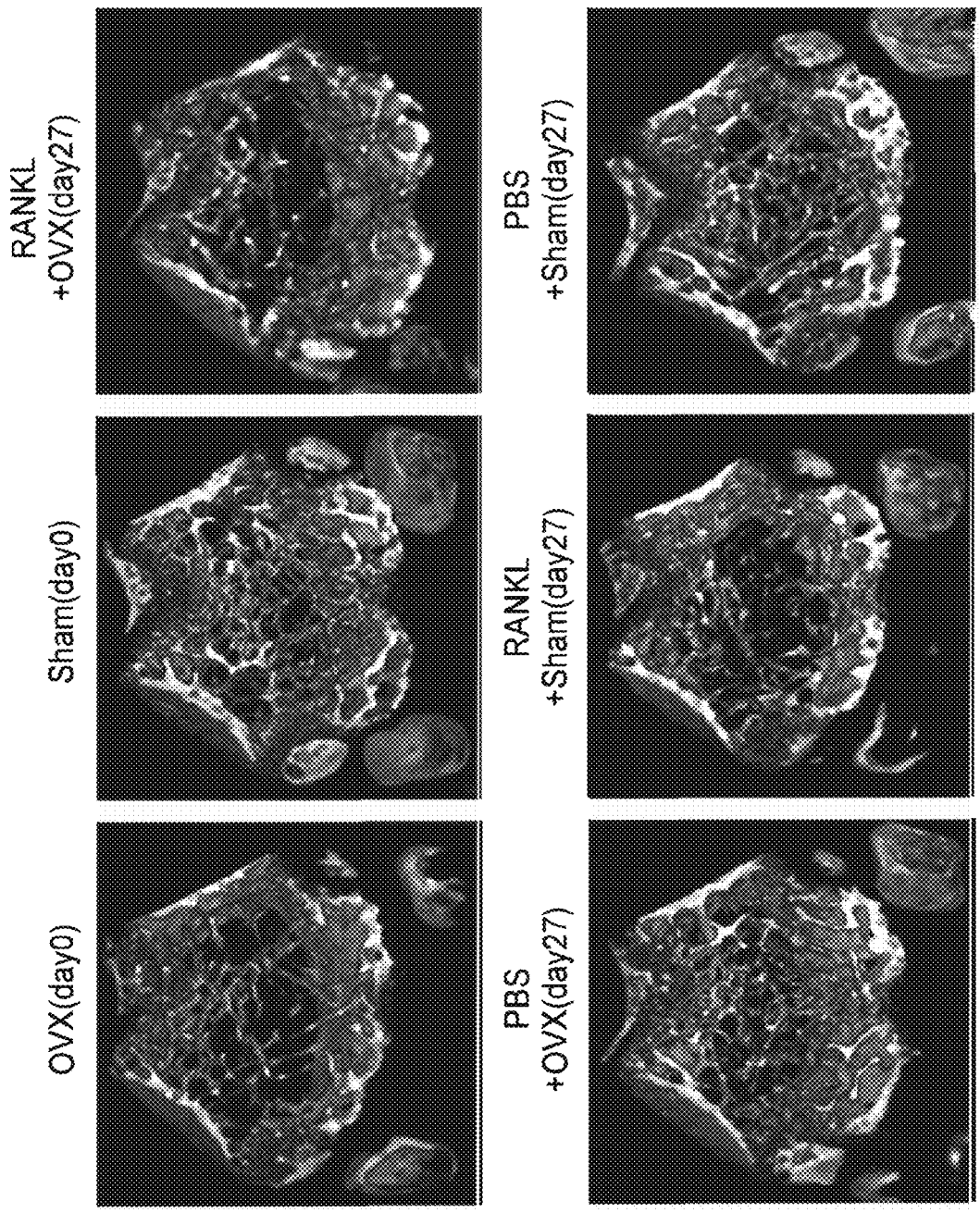
FIG. 45 shows images indicating image analysis results (obtained with micro CT) for mice subjected to administration of GST-RANKL and then subjected to ovariectomy.

The bone density was measured at points 0.6, 0.8, and 1.0 mm from the distal growth plate on the proximal side of the femur. As a result, the bone density for the GST-RANKL administration+Sham (day 27) group and that for the OVX (day 0) group decreased by approximately 7% and approximately 4% at the 0.6-mm point, approximately 14% (p<0.01) and approximately 9% at the 0.8-mm point, and approximately 16% (p<0.01) and approximately 12% (p<0.05) at the 1.0-mm point, respectively, compared with those for the PBS administration+Sham (day 27) group and the Sham (day 0) group serving as the respective control groups. The bone density for the GST-RANKL administration+OVX (day 27) group significantly decreased by approximately 4%, approximately 13%, and approximately 15% (p<0.01) at the aforementioned points compared with that for the PBS administration+Sham (day 27) group serving as the control group. However, there was no difference upon comparison with the GST-RANKL administration+Sham (day 27) group (FIG. 44). Also, the results were confirmed by image analysis with the use of micro CT (FIG. 45).

Based on the above results, the osteopenia mouse models produced by GST-RANKL administration were found to exhibit symptoms similar to those exhibited by conventional ovariectomized mice. In general, production of osteopenia mouse models by ovariectomy must take at least 4 weeks. However, the production time could be shortened to as short as 72 hours by carrying out ovariectomy following GST-RANKL administration. Such mice subjected to ovariectomy following GST-RANKL administration substantially lack estrogen on day 1 after ovariectomy, and thus the hormonal balance in such a mouse becomes similar to that in a conventional osteopenia mouse model subjected to ovariectomy. Thus, a mouse in a state substantially identical to the state of an osteopenia mouse model obtained by ovariectomy could be produced in a simple manner in a short period of time. Such a GST-RANKL/OVX model is an osteopenia model in a state physiologically similar to that of a postmenopausal woman, and it can be produced in a short period of 72 hours. Therefore, such model can be applied to rapid drug evaluation in consideration of hormonal balance.

Bone Healing

GST-RANKL was intraperitoneally administered twice to groups of 7-week-old female C57BL/6N mice at 1 mg/kg every 24 hours. The time point 24 hours after the $2^{nd}$ administration was designated as "week 0." The serum and femur were collected from each mouse separately at weeks 0, 1, 4, 6, and 8 and compared with those collected from mice subjected to PBS administration in a similar manner. Regarding bone metabolism markers, TRAP-5b, calcium (Ca), and alkaline phosphatase (ALP) in the serum were measured. Each femur was subjected to bone density measurement with pQCT and image analysis with micro CT.

Figure 46:
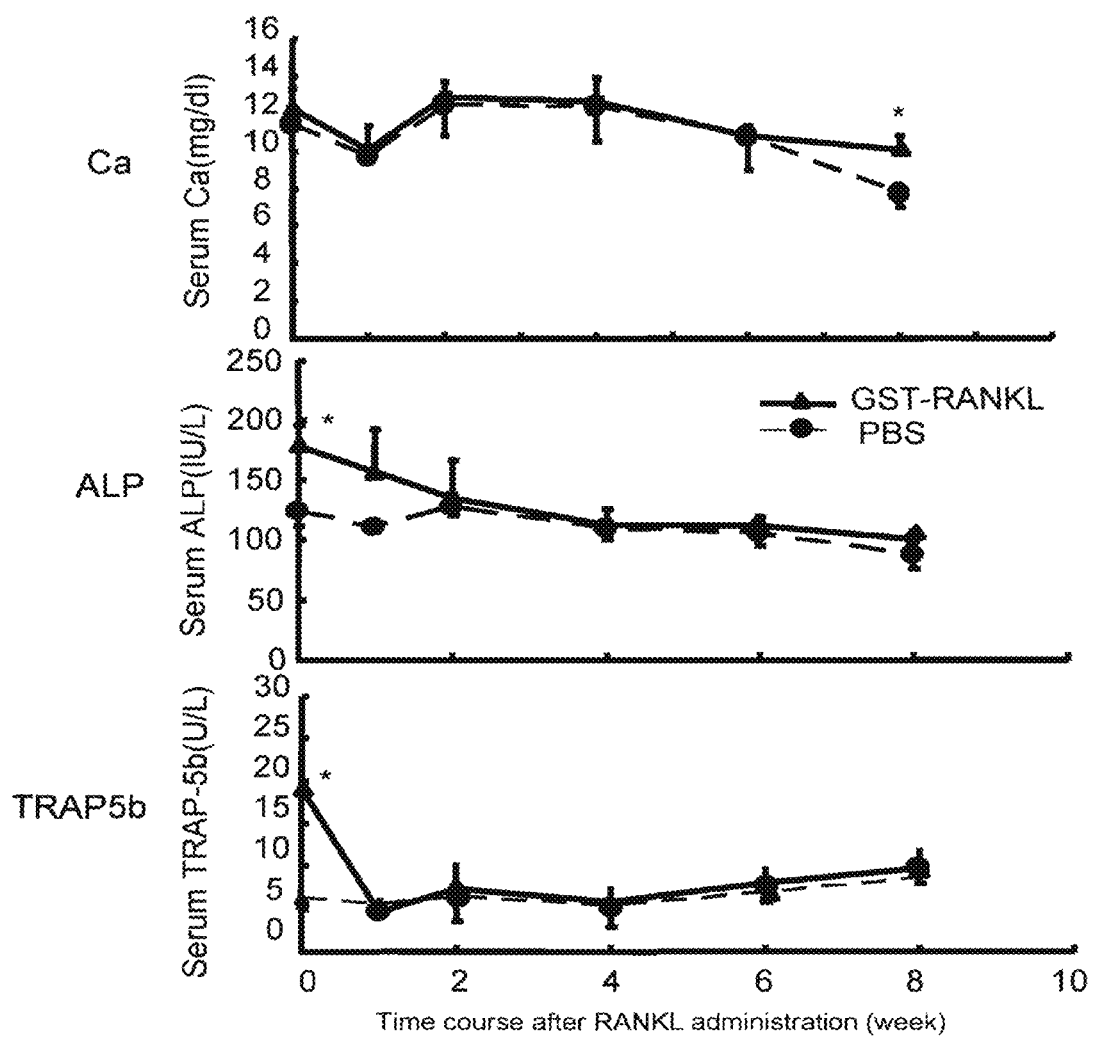
FIG. 46 shows graphs of serum Ca, ALP, and TRAP-5b concentrations in C57BL/6 mice subjected to administration of GST-RANKL and those subjected to administration of PBS.

There was no significant difference in terms of the serum Ca concentration. However, the TRAP-5b concentration measured 24 hours after RANKL administration (0 week) increased to approximately 3-fold as high as that for the PBS administration group. Then, changes in the TRAP-5b concentration were observed to be similar to those for the PBS administration group. The ALP concentration was found to increase to approximately 1.4-fold as high at weeks 0 and 1. Then, changes in the ALP concentration were observed to be similar to those for the PBS administration group (FIG. 46).

The bone density was measured at points 0.6 mm, 0.8 mm, 1.0 mm from the distal growth plate on the proximal side of the femur with the use of pQCT.

Figure 47:
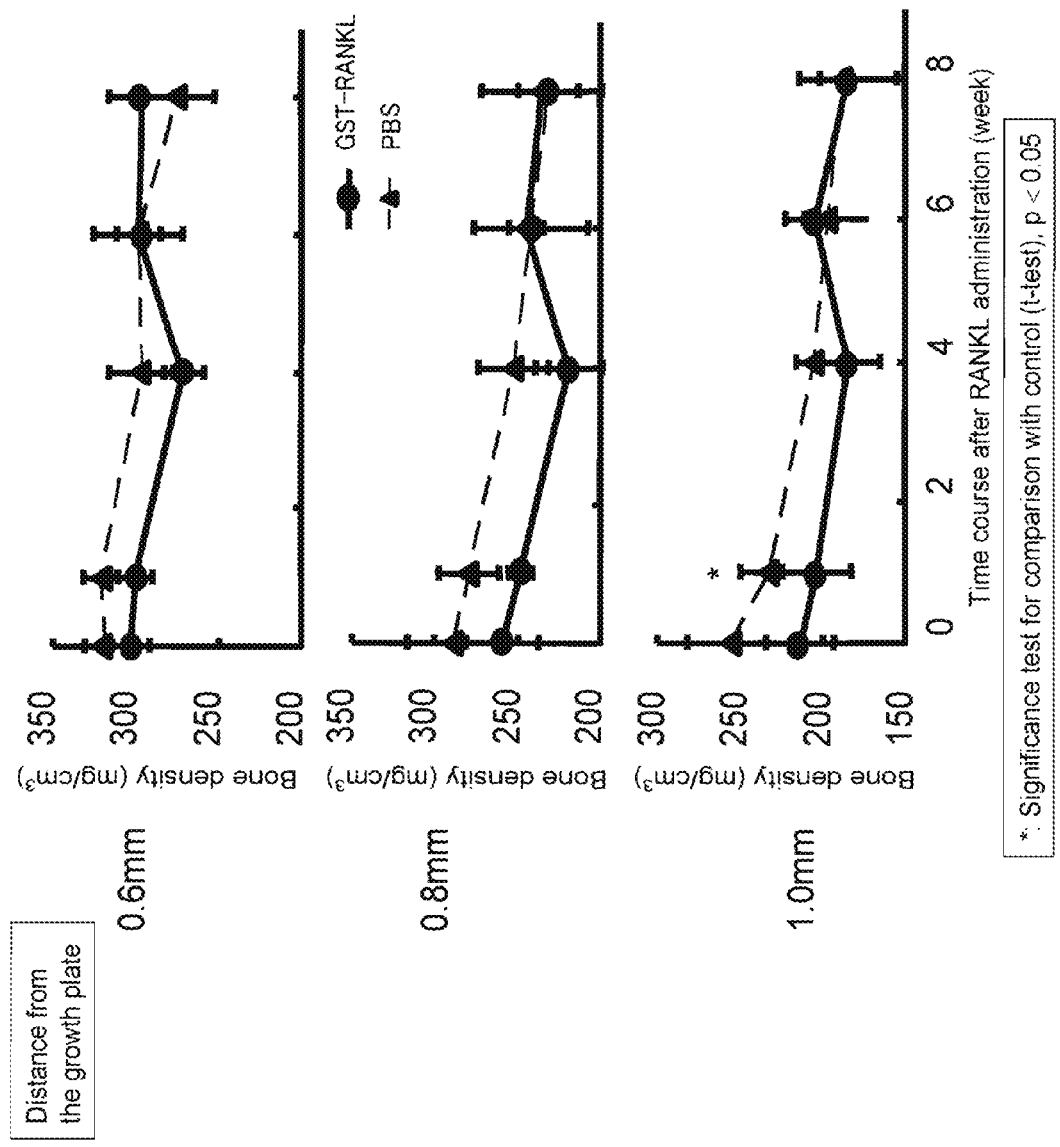
FIG. 47 shows graphs of bone densities in C57BL/6 mice subjected to administration of GST-RANKL and those subjected to administration of PBS.
Figure 48:
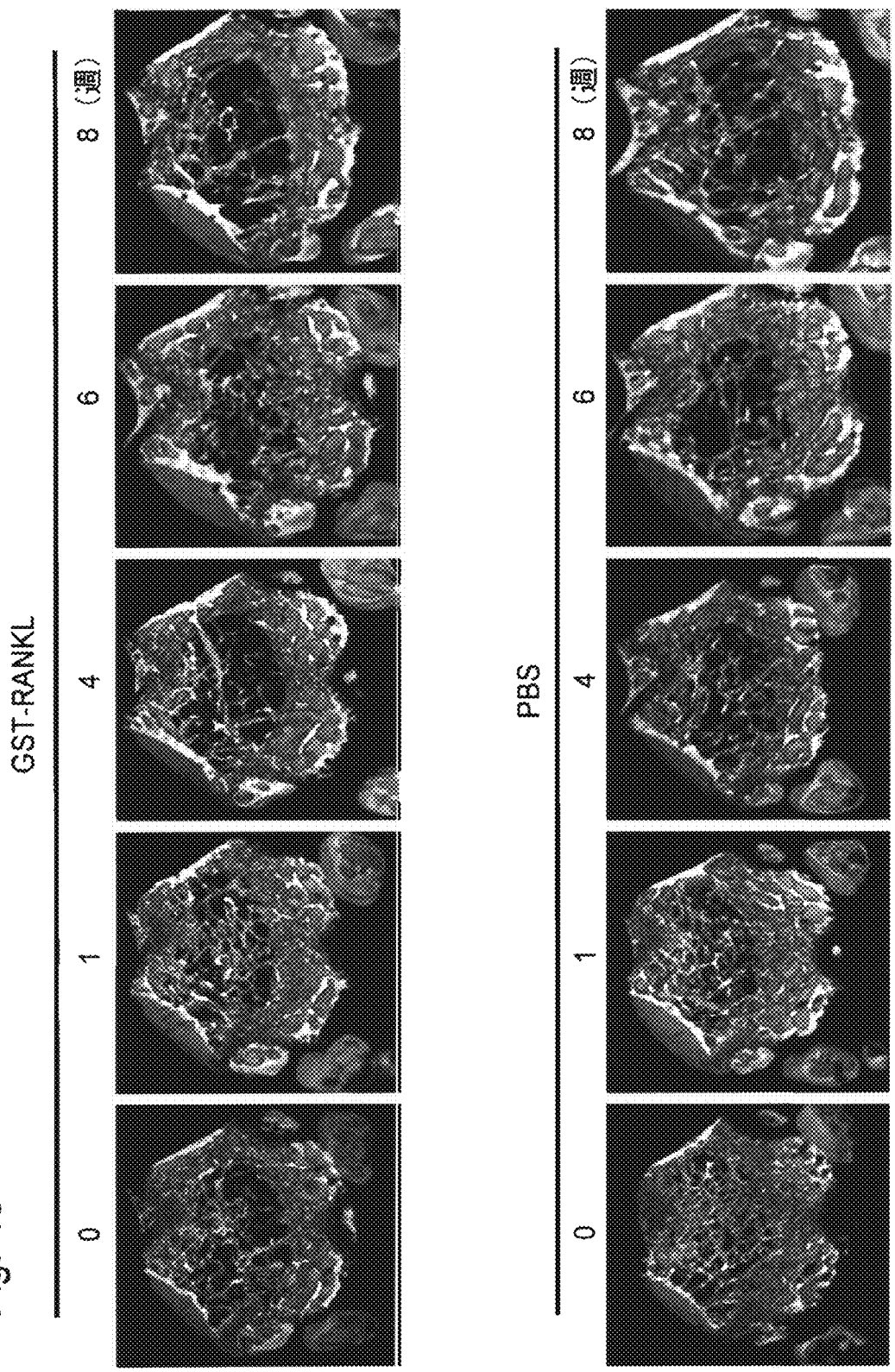
FIG. 48 shows images indicating image analysis results (obtained with micro CT) for C57BL/6 mice subjected to administration of GST-RANKL and those subjected to administration of PBS.

As a result of bone density measurement with pQCT, the bone density was found to have decreased to 5%, 7%, and 9% (at weeks 0, 1, and 4, respectively) at the 0.6-mm point, 10%, 11%, and 15% (at weeks 0, 1, and 4, respectively) at the 0.8-mm point, and 16%, 13%, and 11% (at weeks 0, 1, and 4, respectively) at the 1.0-mm point, compared with that for the PBS group. The bone density was found to decrease at the 0.6-, 0.8-, and 1.0-mm points 4 weeks after RANKL administration compared with that for the PBS administration group. Thereafter, the bone density returned to a level comparable to that for the PBS administration group at week 6 (FIG. 47). Also, the above results were confirmed by image analysis with micro CT (FIG. 48).

The results indicate that an osteopenia mouse model obtained by RANKL administration is useful for comparison of the degree of bone mass recovery. That is, it was found that it had become possible to evaluate a drug capable of promoting a bone mass increase within 6 weeks after the $2^{nd}$ RANKL administration.

Evaluation of a Bone Mass Increase with PTH

GST-RANKL was administered twice to groups of 7-week-old female C57BL/6N mice at 1 mg/kg every 24 hours. Ovariectomy was performed 24 hours after the $2^{nd}$ administration. In addition, parathyroid hormone (PTH) was subcutaneously administered thereto at 160 μg/kg from 24 hours after the ovariectomy for 10 consecutive days. Further, a group obtained by PBS administration and sham operation (Sham) was designated as a control group for comparison. The serum markers and the femur bone density were measured.

Figure 49:
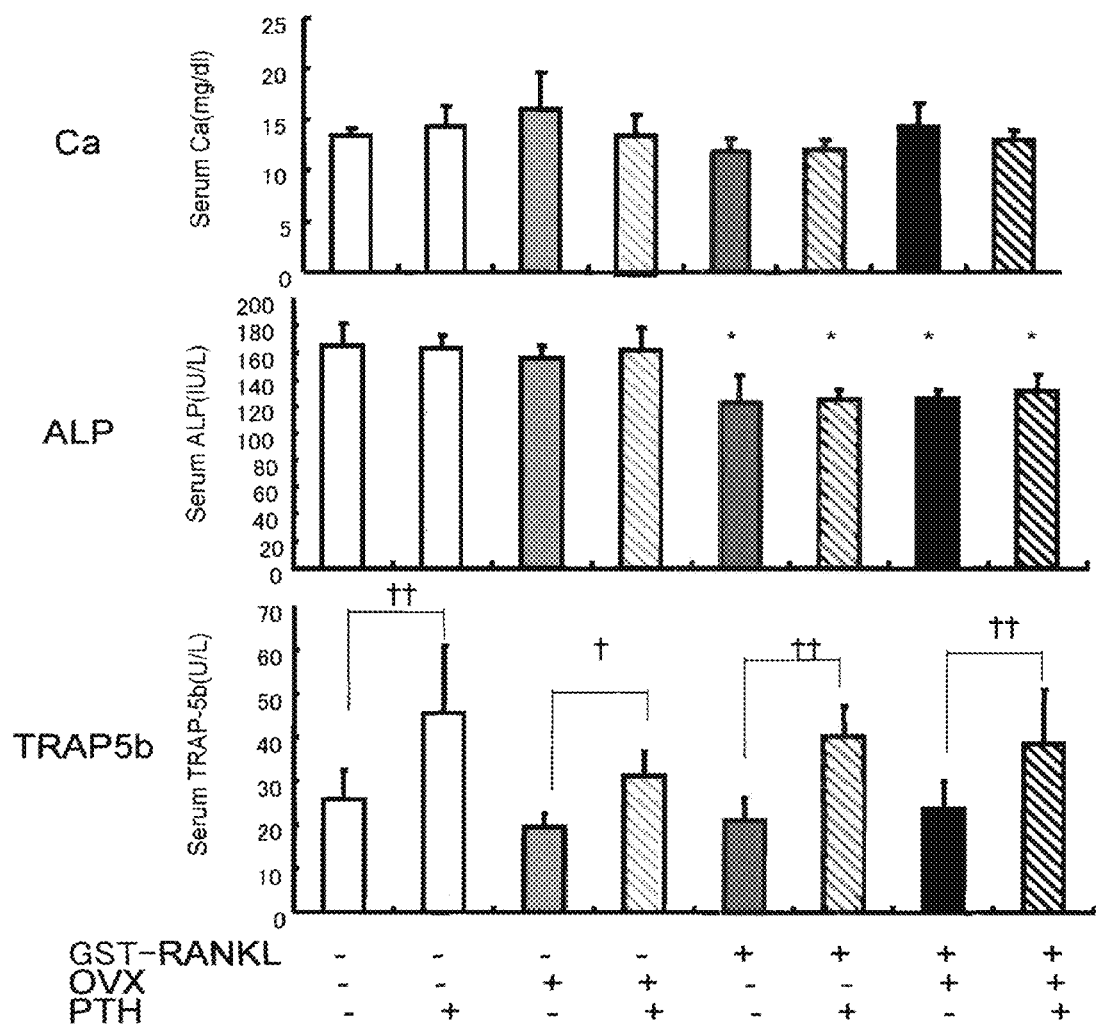
FIG. 49 shows graphs of serum Ca, ALP, and TRAP-5b concentrations in mice subjected to administration of GST-RANKL and then subjected to ovariectomy, to which PTH was further administered.

The serum ALP concentration decreased by approximately 24% in every GST-RANKL administration group; however, there were no changes in the Ca concentration. In addition, the TRAP-5b concentration for every PTH administration group significantly increased to approximately 1.5-fold ($p<0.05$) as high as that for the relevant group not treated with PTH (FIG. 49). Further, there were no changes between the PBS administration+Sham group and the PBS administration+OVX group and between the same and the RANKL administration+Sham group.

Figure 50:
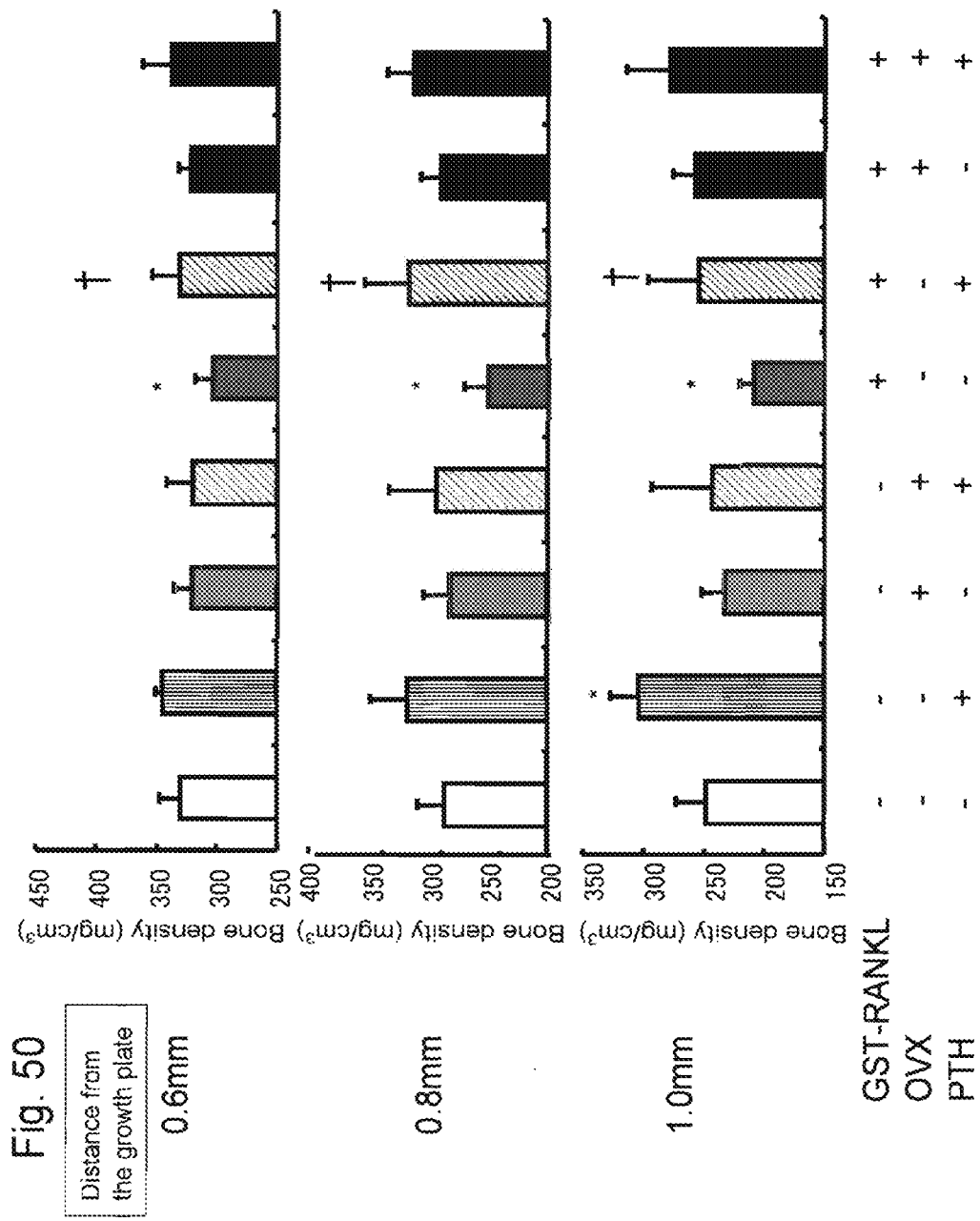
FIG. 50 shows graphs of bone densities in mice subjected to administration of GST-RANKL and then subjected to ovariectomy, to which PTH was further administered.
Figure 51:
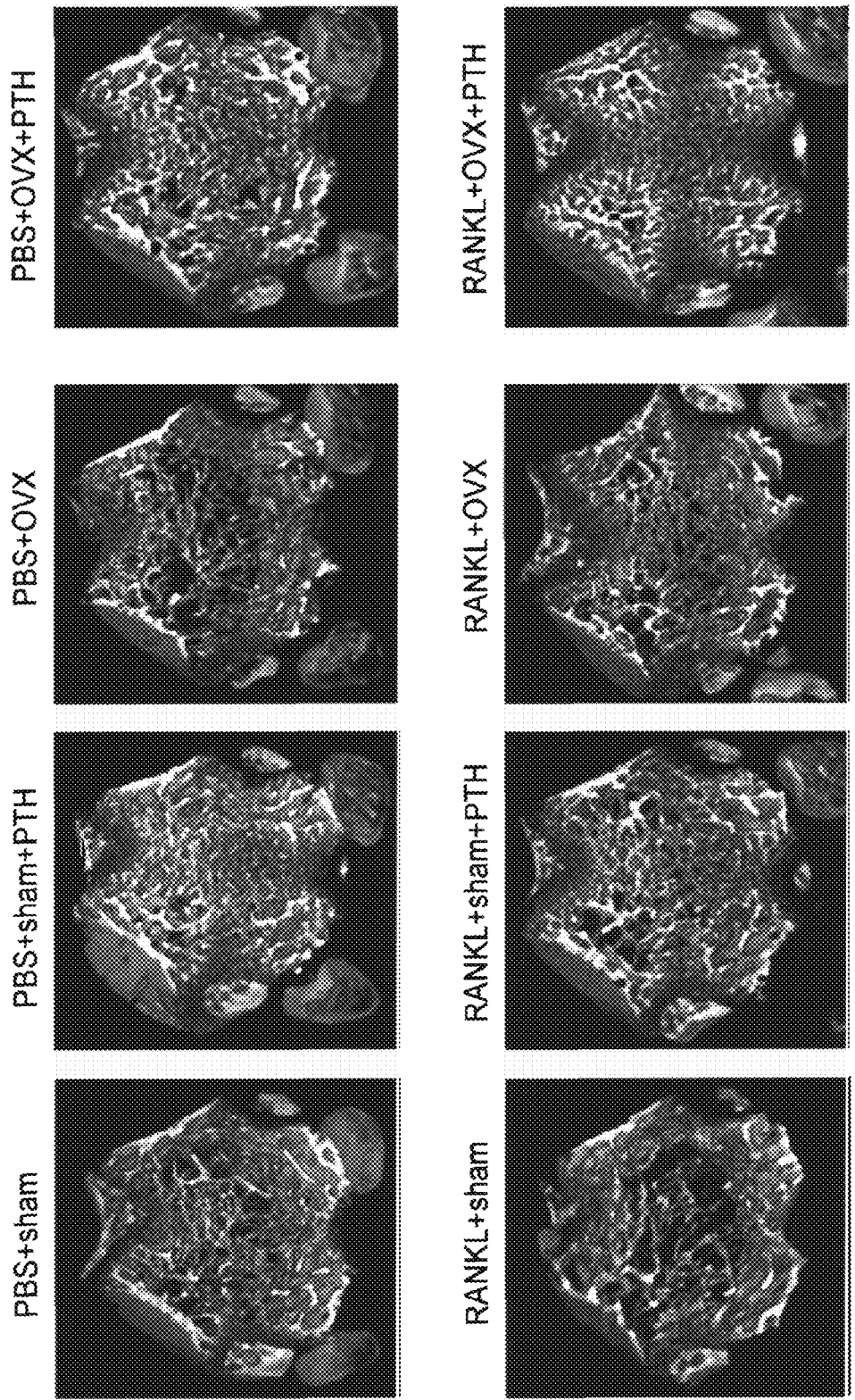
FIG. 51 shows images indicating image analysis results (obtained with micro CT) for mice subjected to administration of GST-RANKL and then subjected to ovariectomy, to which PTH was further administered.

The bone density was measured at points 0.6 mm, 0.8 mm, and 1.0 mm from the distal growth plate on the proximal side. The bone density for the GST-RANKL+Sham group decreased by approximately 17% ($p<0.05$), 15% ($p<0.05$), and 18% ($p<0.05$) at the aforementioned points compared with that for the PBS+Sham group. In addition, the bone density for the OVX group decreased by approximately 5%, 4%, and 8%; however, a sufficient decrease in the bone density was not observed during 10 days after OVX. No bone density decrease was observed in the GST-RANKL+OVX group compared with the PBS+Sham group. In the case in which PTH was administered to the PBS+Sham group, the bone density significantly increased exclusively at the 1.0-mm point ($p<0.05$). Also, the bone density was found to increase in the OVX group even with the administration of PTH; however, no significant difference was obtained. Meanwhile, in the case in which PTH was administered to the GST-RANKL+Sham group, a bone density decrease was significantly suppressed ($p<0.05$), and thus the bone density was higher than that for the PBS+Sham group (FIG. 50). Also, the above results were confirmed by image analysis with micro CT (FIG. 51).

The above results indicate that an osteopenia mouse model obtained by GST-RANKL administration can be used for evaluation of osteogenesis promoters such as PTH, in addition to bone resorption suppressants such as bisphosphonate, by changing the time point and the time period for evaluation. In addition, it was found that GST-RANKL administration results in osteogenesis activation such that PTH evaluation can be carried out in a shorter time period with high sensitivity.

Evaluation of Male Mice

GST-RANKL was intraperitoneally administered 3 times to groups of 7-week-old male C57BL/6N mice at 1 mg/kg every 24 hours. The femur and serum were collected from each mouse 1.5 hours after the $3^{rd}$ administration and compared with those of the PBS administration group. Regarding bone metabolism markers, TRAP-5b, calcium (Ca), and alkaline phosphatase (ALP) in the serum were measured. Each femur was subjected to bone density measurement with pQCT and image analysis with micro CT.

Figure 52:
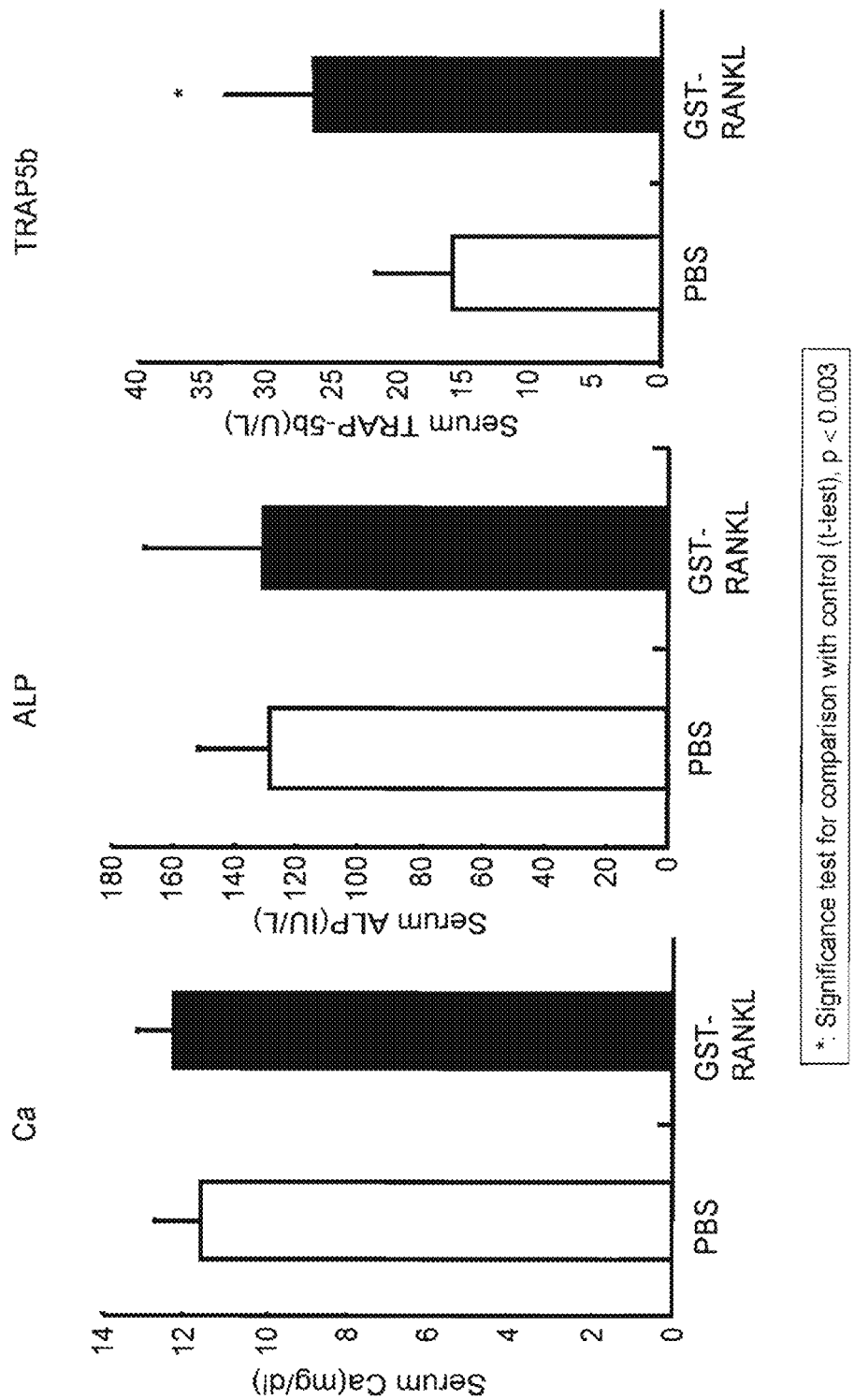
FIG. 52 shows graphs of serum Ca, ALP, and TRAP-5b concentrations in male mice subjected to administration of GST-RANKL and those subjected to administration of PBS.
Figure 53:
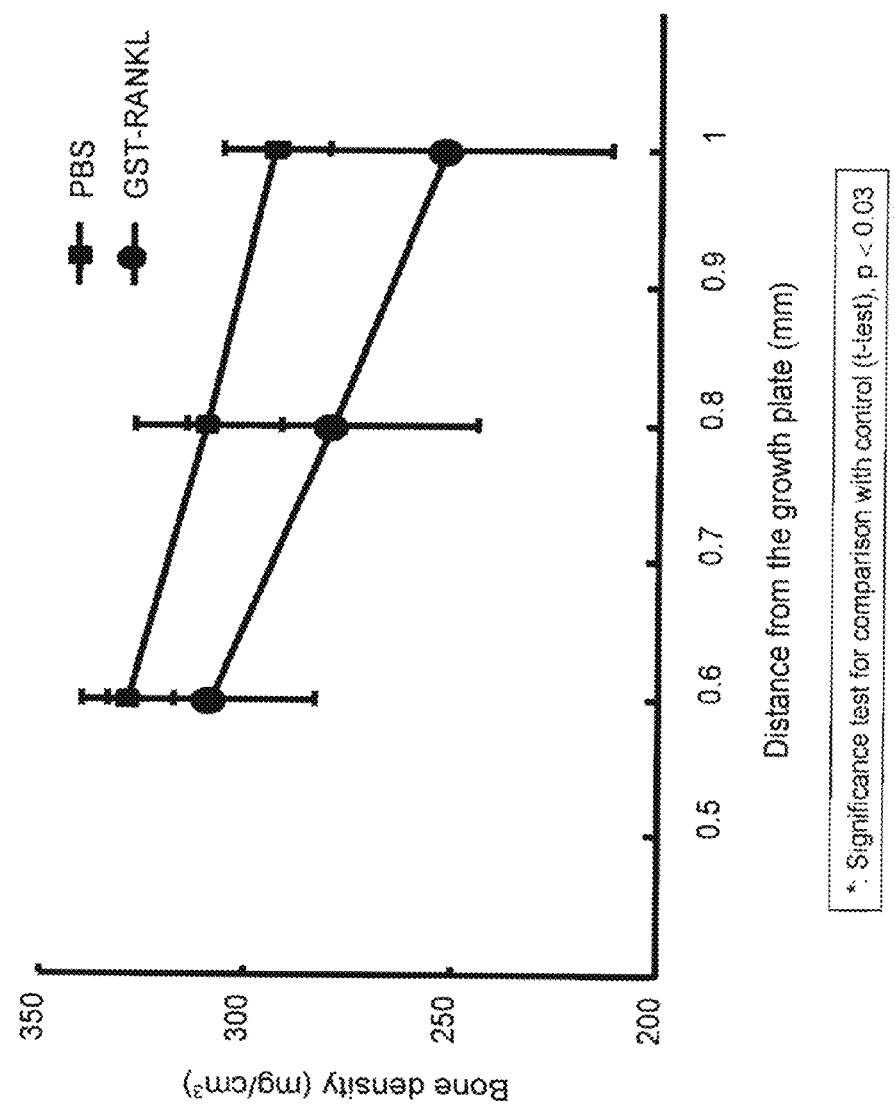
FIG. 53 shows a graph of bone densities in male mice subjected to administration of GST-RANKL and those subjected to administration of PBS.

The Ca concentration increased by 7% compared with that for the PBS administration group; however, no significant difference was obtained. The TRAP-5b concentration significantly increased by approximately 65% ($p<0.003$). In addition, no changes were observed in terms of the ALP concentration (FIG. 52). The bone density was measured at points 0.6, 0.8, and 1.0 mm from the distal growth plate on the proximal side of the femur. The bone density was found to decrease by approximately 6%, approximately 10%, and approximately 15% ($p<0.03$) at the 0.6-, 0.8-, and 1.0-mm points, respectively (FIG. 53). Also, the results were confirmed by image analysis with micro CT (FIG. 54).

The above results indicate that an osteopenia mouse model obtained by GST-RANKL administration can be used regardless of gender, unlike conventional ovariectomized mouse models. In addition, it has been known that it is possible to obtain male mice, which can be used as osteopenia mouse models, by means of hindlimb suspension, low-calcium diet, neurectomy, or the like. However, osteopenia mouse models obtained by GST-RANKL administration are superior to such mouse models in terms of short production time.

Evaluation of Mice of the Other Lineages

GST-RANKL was intraperitoneally administered 3 times to groups of 7-week-old female ICR mice at 1 mg/kg every 24 hours. The femur and serum were collected from each mouse 1.5 hours after the $3^{rd}$ administration and compared with those of the PBS administration group. Regarding bone metabolism markers, TRAP-5b, calcium (Ca), and alkaline phosphatase (ALP) in the serum were measured. Each femur was subjected to bone density measurement with pQCT and image analysis with micro CT.

Figure 55:
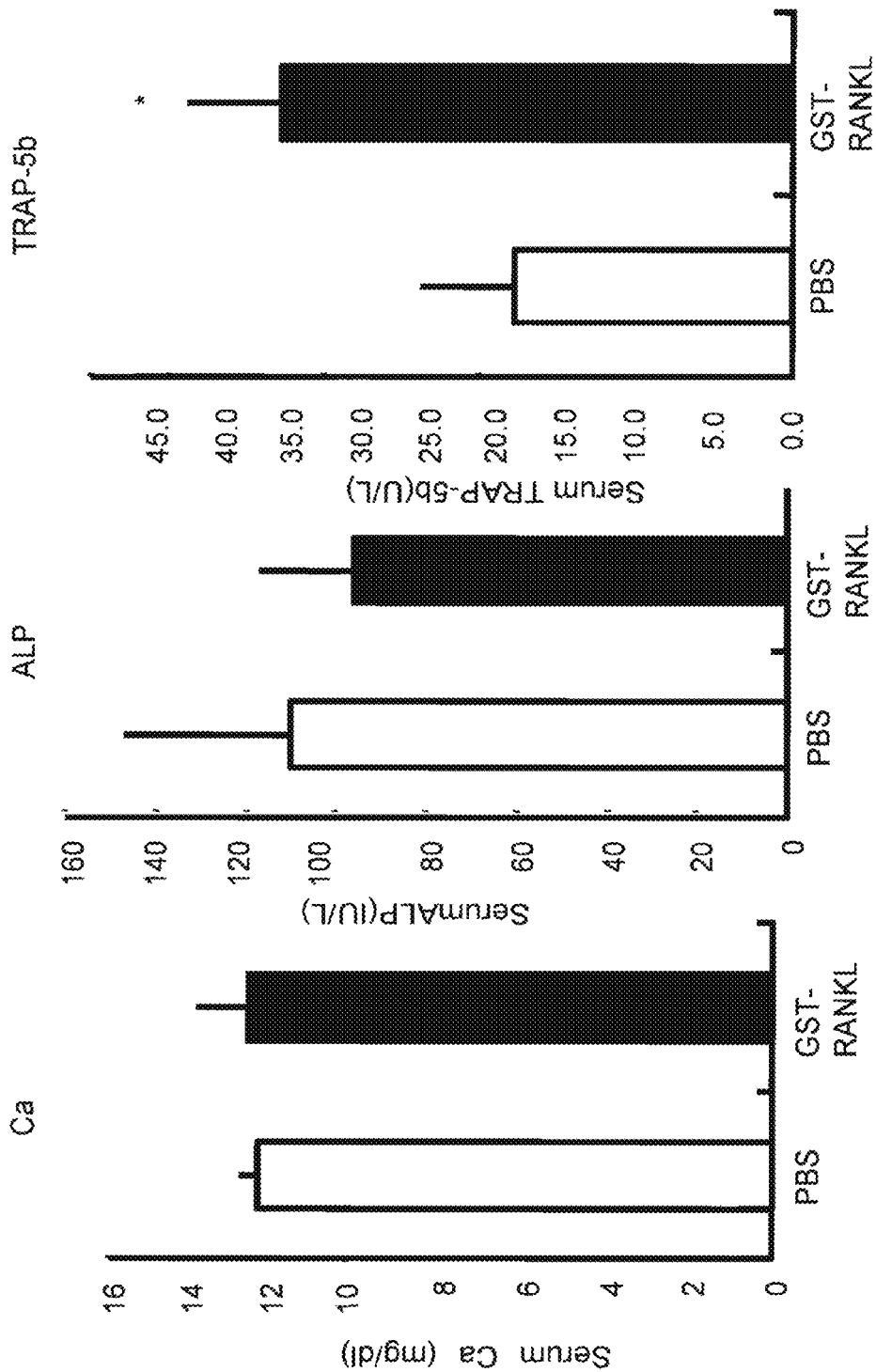
FIG. 55 shows graphs of serum Ca, ALP, and TRAP-5b concentrations in ICR mice treated with GST-RANKL and those treated with PBS.
Figure 56:
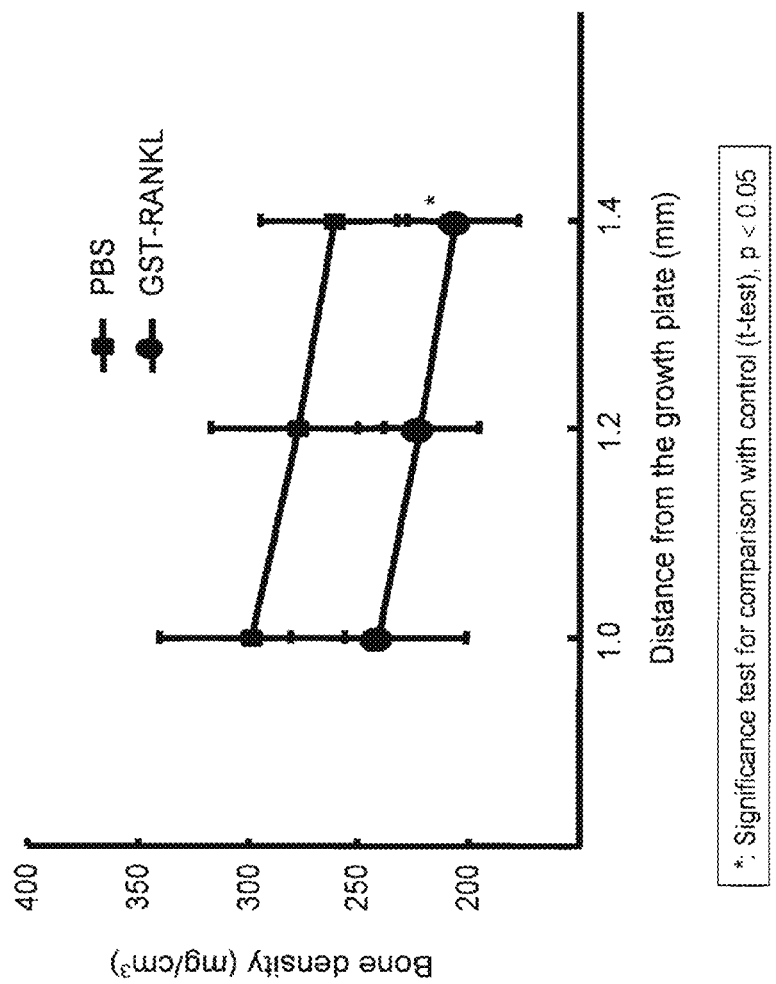
FIG. 56 shows a graph of bone densities in ICR mice subjected to administration of GST-RANKL and those subjected to administration of PBS.
Figure 57:
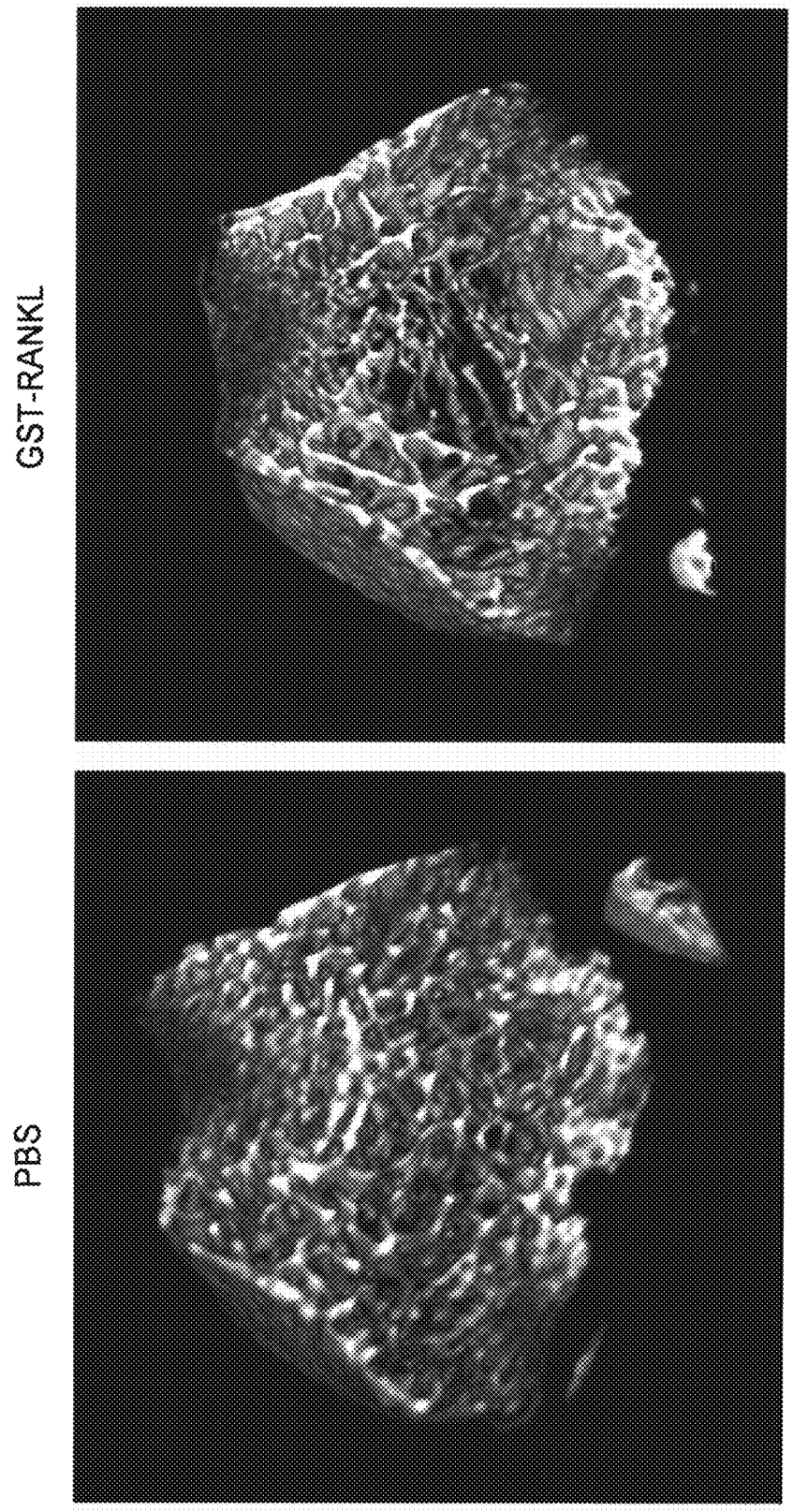
FIG. 57 shows images indicating image analysis results (obtained with micro CT) for an ICR mouse subjected to administration of GST-RANKL and those subjected to administration of PBS.

There were no changes in the serum Ca concentration in the GST-RANKL administration group compared with that for the control group. However, the TRAP-5b concentration increased to 1.8-fold as high as that for the PBS administration group ($p<0.01$). In addition, there were no changes in the ALP concentration (FIG. 55). The bone density was measured at points 1.0, 1.2, and 1.4 mm from the distal growth plate on the proximal side of the femur. The bone density decreased by approximately 20%, approximately 20%, and approximately 22% ($p<0.05$) at the 1.0-, 1.2-, and 1.4-mm points, respectively, compared with that for the control group (FIG. 56). Also, the above results were confirmed by image analysis with micro CT (FIG. 57). The results indicate that osteopenia mouse models can be produced by RANKL administration not only from C57BL/6 mice but also from mice of the other lineages.

Examination with the Use of Fischer Rats

GST-RANKL was intraperitoneally administered 3 times to 7-week-old female Fischer rats at 1 mg/kg every 24 hours. The serum and femur were collected from each mouse 1.5 hours after the $3^{rd}$ administration, followed by comparison with the PBS administration group. The serum of each mouse was subjected to measurement (with the use of an SB-TR102 kit, IDS Ltd.) of the Ca and TRAP-5b concentrations serving as bone resorption markers and the ALP concentration serving as an osteogenesis marker. Each femur was subjected to bone density measurement with pQCT and image analysis with micro CT.

Figure 58:
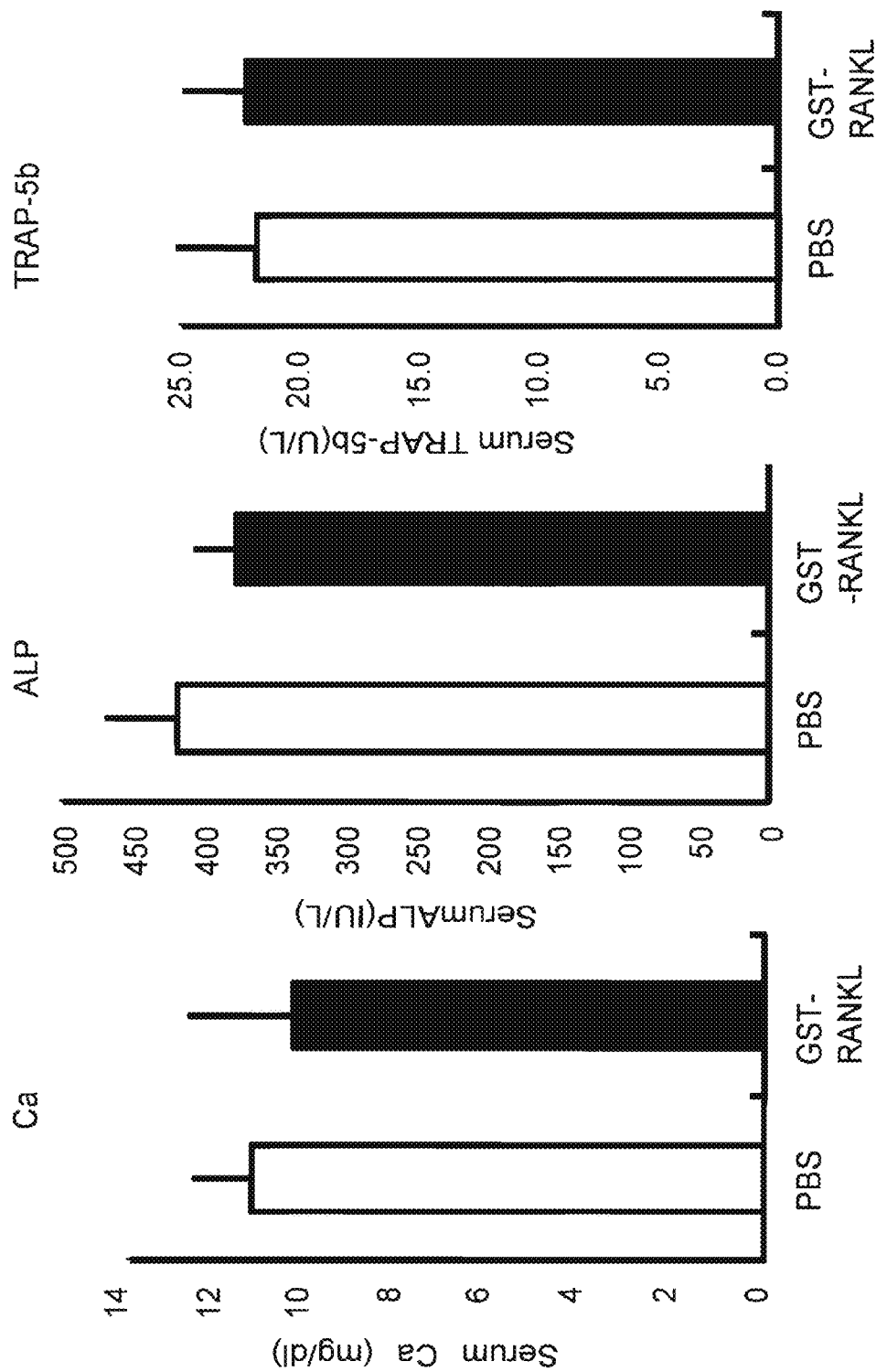
FIG. 58 shows graphs of serum Ca, ALP, and TRAP-5b concentrations in Fischer rats subjected to administration of GST-RANKL and those subjected to administration of PBS.
Figure 59:
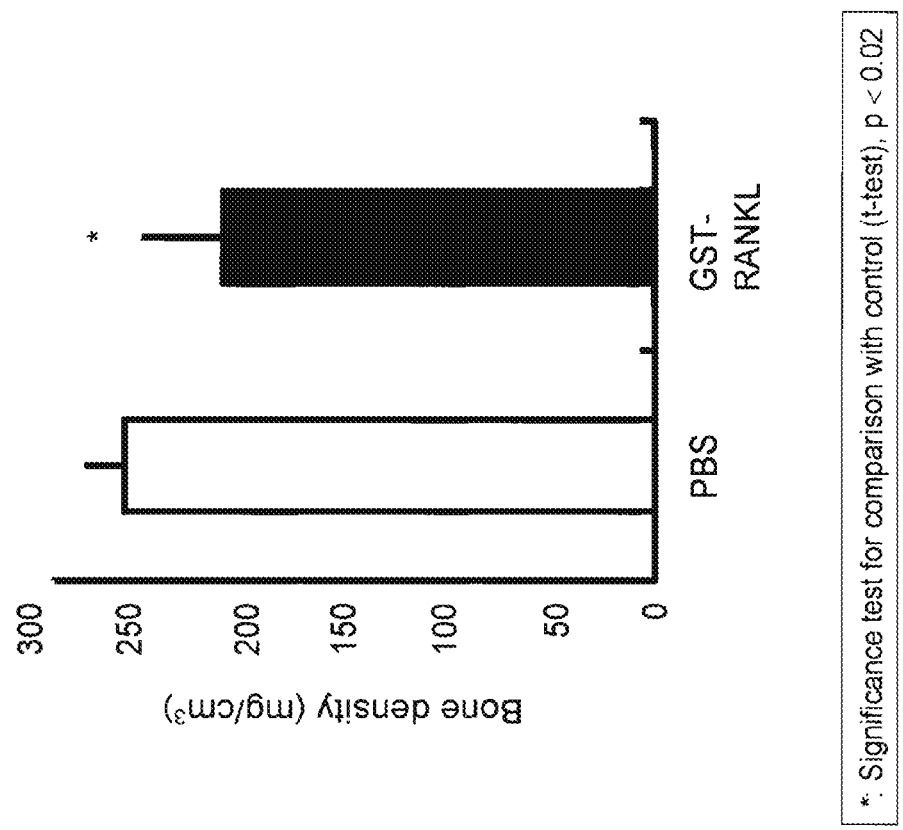
FIG. 59 shows a graph of bone densities in Fischer rats subjected to administration of GST-RANKL and those subjected to administration of PBS.

There were no changes in the serum TRAP-5b, Ca, and ALP concentrations compared with those for the control group (FIG. 58). However, the bone density was found to have decreased by approximately 20% ($p<0.02$) as a result of measurement at the point 3 mm from the distal growth plate on the proximal side of the femur (FIG. 59). Also, the above results were confirmed by image analysis with micro CT (FIG. 60). The results revealed that osteopenia models can be produced by RANKL administration not only from mice but also from the other animals such as rats.

Single-Dose Administration of GST-RANKL

GST-RANKL was intraperitoneally administered to groups of 7-week-old female C57BL/6N mice at 1 mg/kg. The bone resorption markers and the osteogenesis markers in the serum were measured 12, 24, and 48 hours thereafter. Blood sampling was carried out before and immediately after GST-RANKL administration and 2, 4, 8, 12, 24, 48, and 72 hours after administration, followed by measurement of the serum human RANKL concentration by ELISA. In addition, 24 and 48 hours after administration, the femur bone density was measured with pQCT.

Figure 61:
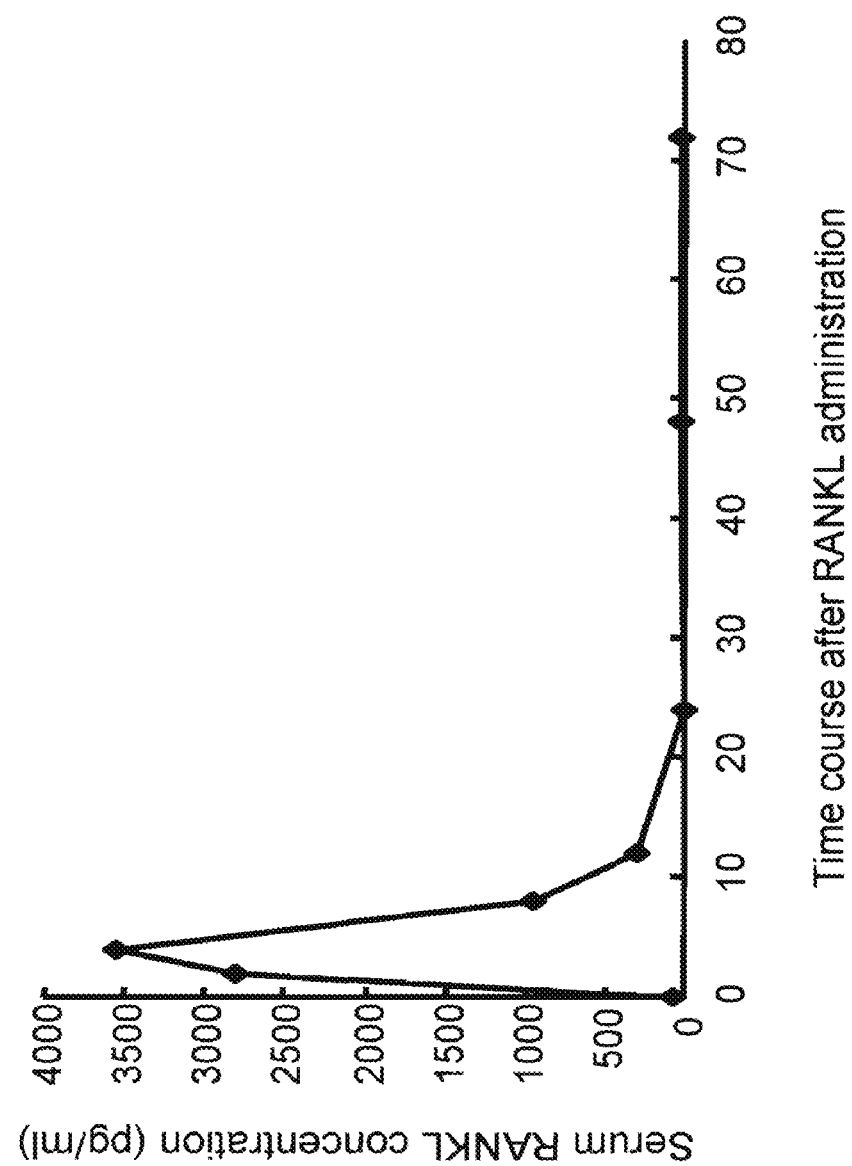
FIG. 61 shows a graph of serum RANKL concentrations in mice subjected to single-dose administration of GST-RANKL.
Figure 62:
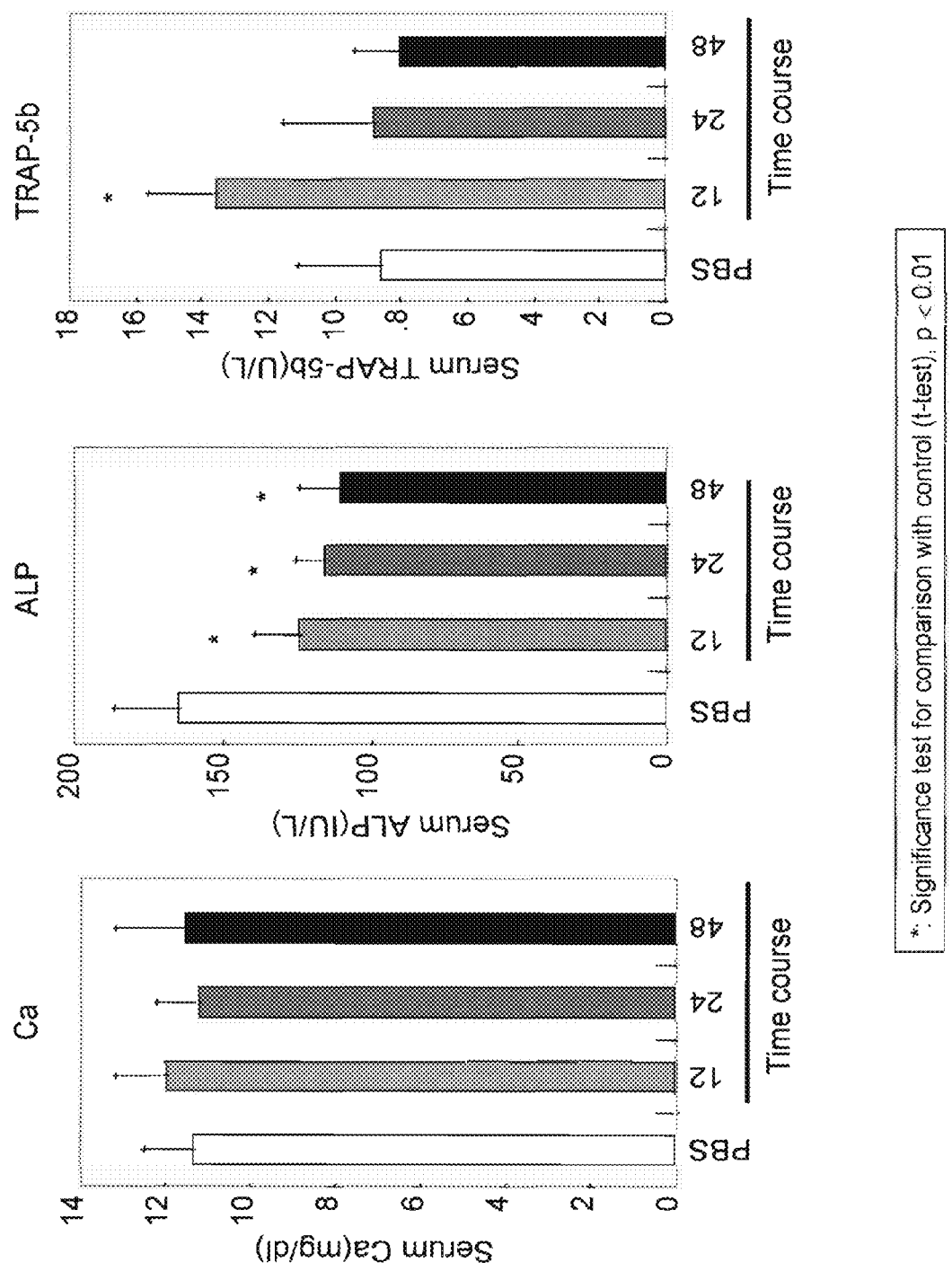
FIG. 62 shows graphs of serum Ca, ALP, and TRAP-5b concentrations in mice subjected to single-dose administration of GST-RANKL and mice subjected to single-dose administration of PBS.
Figure 63:
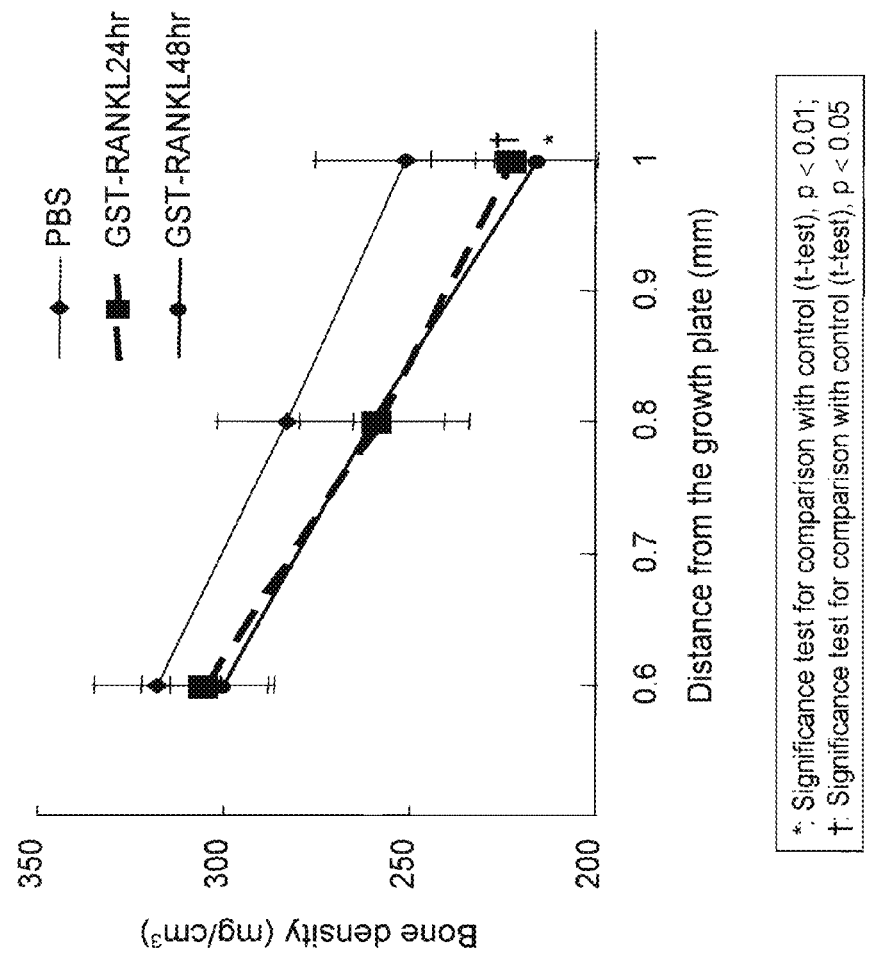
FIG. 63 shows a graph of bone densities in mice subjected to single-dose administration of GST-RANKL and mice subjected to single-dose administration of PBS.
Figure 64:
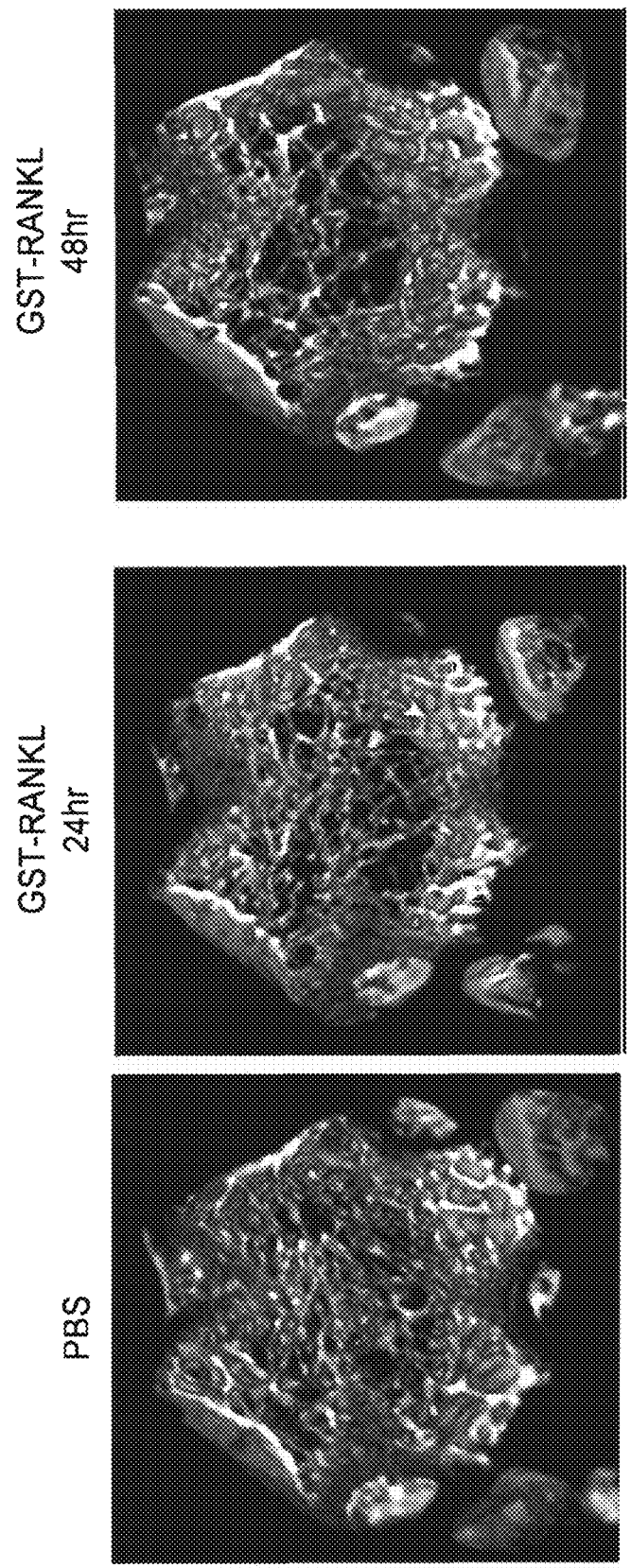
FIG. 64 shows images indicating image analysis results (obtained with micro CT) for mice subjected to single-dose administration of GST-RANKL and a mouse subjected to single-dose administration of PBS.

The serum human RANKL concentration quickly increased after administration and reached its peak 4 hours later. Then, the concentration sharply decreased and became undetectable 24 hours later (FIG. 61). There were no changes in the serum Ca concentration. The TRAP-5b concentration significantly increased to approximately 1.7-fold ($p<0.01$) as high as that for the control group 12 hours after administration. In addition, the ALP concentration significantly decreased by approximately 30% ($p<0.01$) in the GST-RANKL administration group (FIG. 62). The bone density was measured at points 0.6, 0.8, and 1.0 mm from the distal growth plate on the proximal side of the femur. The bone density at 24 hours later and that at 48 hours later decreased by approximately 4% and approximately 5%, respectively, at the 0.6-mm point, approximately 9% and approximately 9%, respectively, at the 0.8-mm point, and approximately 12% ($p<0.05$) and approximately 15% ($p<0.01$), respectively, at the 1.0-mm point, compared with those for the control group (FIG. 63). Also, the above results were confirmed by image analysis with micro CT (FIG. 64).

The results indicate that single-dose administration of GST-RANKL at 1 mg/kg would result in significant bone mass decreases. Meanwhile, based on comparison of the results of single-dose administration and those of double-dose administration, it is considered that double-dose administration is preferable because a significant bone density decrease was observed at the points 0.6, 0.8, and 1.0 mm from the distal growth plate on the proximal side. However, the results indicate that even single-dose administration can cause a sufficient bone density decrease. In the case of double-dose administration of GST-RANKL, bone mass decreasing effects were promoted at a dose of 2 mg/kg compared with those obtained at doses of 0.5 mg/kg and 1 mg/kg. Thus, even in the case of single-dose administration, the degree of osteopenia can be arbitrarily controlled by increasing the dose. That is to say, even in the case of single-dose administration, it can be expected that a significant bone density decrease would be observed at a dose of, for example, 2 mg/kg at the 3 points 0.6, 0.8, and 1.0 mm from the distal growth plate on the proximal side.

Administration of GST-RANKL for 7 Consecutive Days

GST-RANKL was intraperitoneally administered to groups of 7-week-old female C57BL/6 mice at 2 mg/kg/day for 7 consecutive days. The serum and femur were collected from each mouse 1.5 hours after the $7^{th}$ administration. The serum and femur obtained from each mouse were subjected to measurement of serum markers and bone density measurement with pQCT, respectively.

Figure 65:
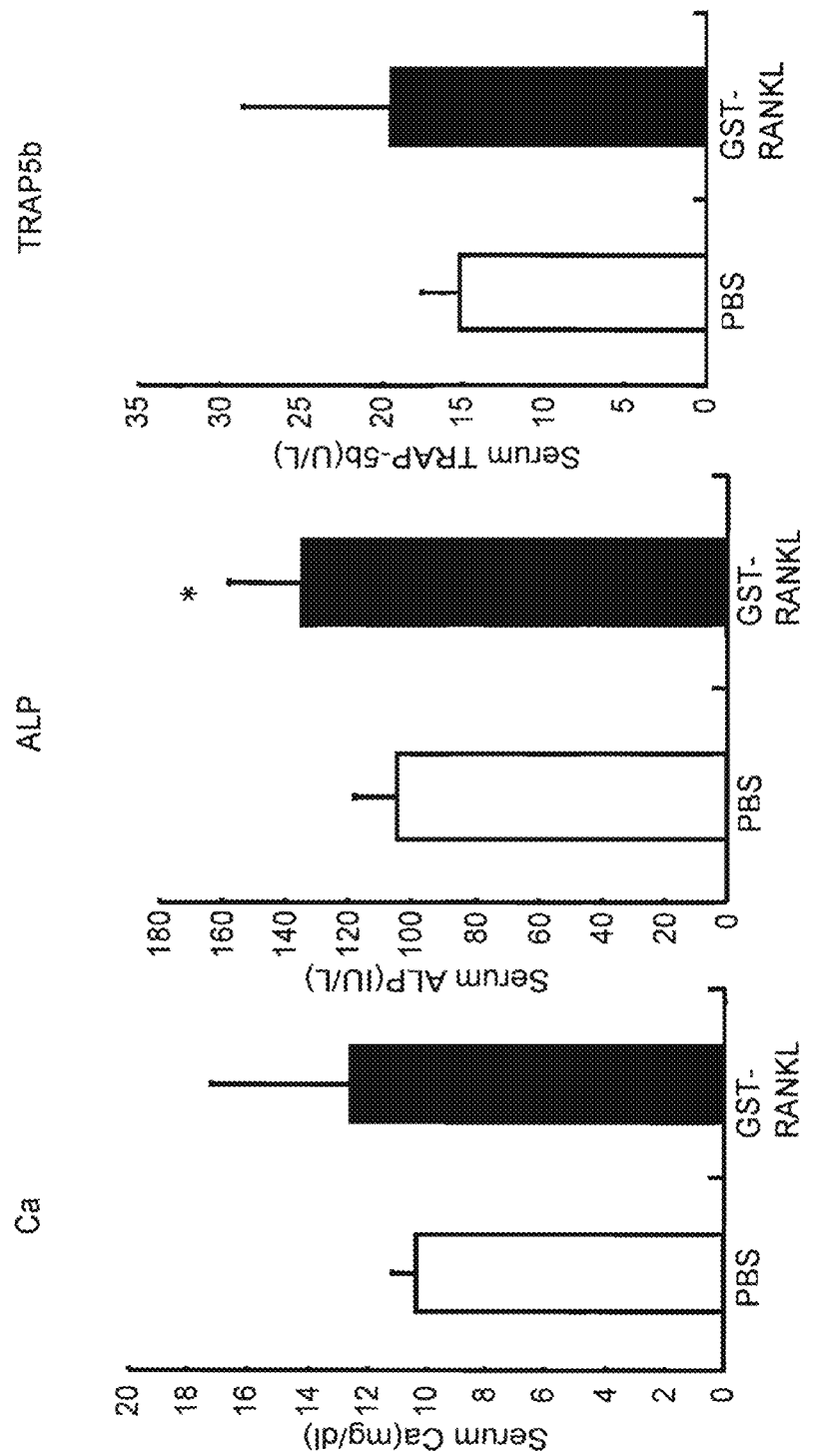
FIG. 65 shows graphs of serum Ca, ALP, and TRAP-5b concentrations in mice subjected to administration of GST-RANKL and mice subjected to administration of PBS for 7 consecutive days.
Figure 66:
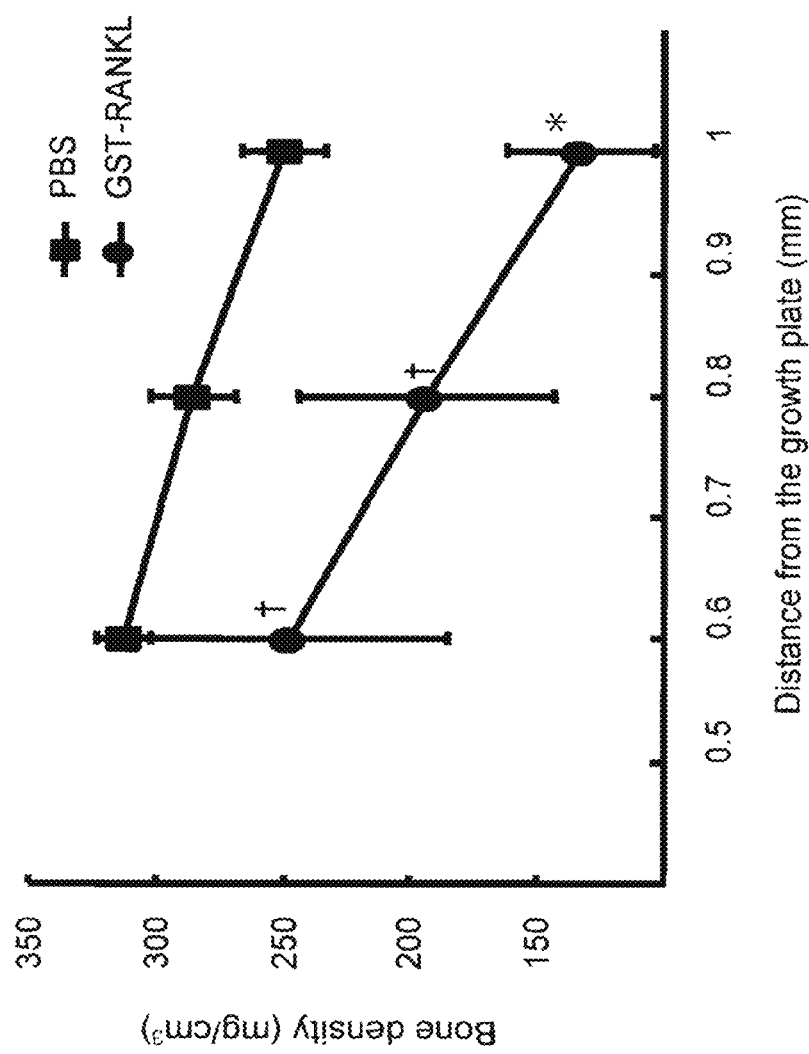
FIG. 66 shows a graph of bone densities in mice subjected to administration of GST-RANKL and mice subjected to administration of PBS for 7 consecutive days.

The Ca concentration serving as a bone resorption marker increased by approximately 20%; however, no significant difference was obtained. Also, the TRAP-5b concentration tended to increase by approximately 30%; however, no significant difference was obtained. Further, the ALP concentration significantly increased by approximately 30% ($p<0.02$) (FIG. 65). The bone density was measured at points 0.6, 0.8, and 1.0 mm from the distal growth plate on the proximal side of the femur. The bone density decreased by approximately 21% ($p<0.05$), approximately 32% ($p<0.05$), and approximately 47% ($p<0.01$) at the 0.6-, 0.8-, and 1.0-mm points, respectively, compared with that for the control group (FIG. 66). Also the above results were confirmed by image analysis with micro CT (FIG. 67).

Based on the above results, it can be assumed that a coupling phenomenon induced by bone resorption and osteogenesis took place. This is because the osteogenesis markers increased, in addition to the bone resorption markers, as a result of administration for 7 consecutive days. Therefore, such a mouse model was found to be applicable for elucidation of the above coupling phenomenon, as well as for studies of osteopenia and osteoporosis.

Administration of GST-RANKL to Mouse Calvaria

GST-RANKL was administered to the calvaria of groups of 8-week-old female C57BL/6N mice for 3 days. The femur was collected from each mouse on day 5 day after the initiation of experimentation. The femur bone density was evaluated with pQCT. Experimentation was conducted with the use of the following three experimental groups: the experimental group 1 subjected to administration of GST-RANKL at 0.5 mg/kg twice daily; the experimental group 2 subjected to administration of GST-RANKL at 1 mg/kg once daily; and the PBS group serving as a control group for comparison and being subjected to PBS administration. Cancellous bone density measurement was carried out at points 0.6 mm, 0.8 mm, and 1.0 mm from the distal growth plate on the proximal side of the collected femur with pQCT.

Figure 68:
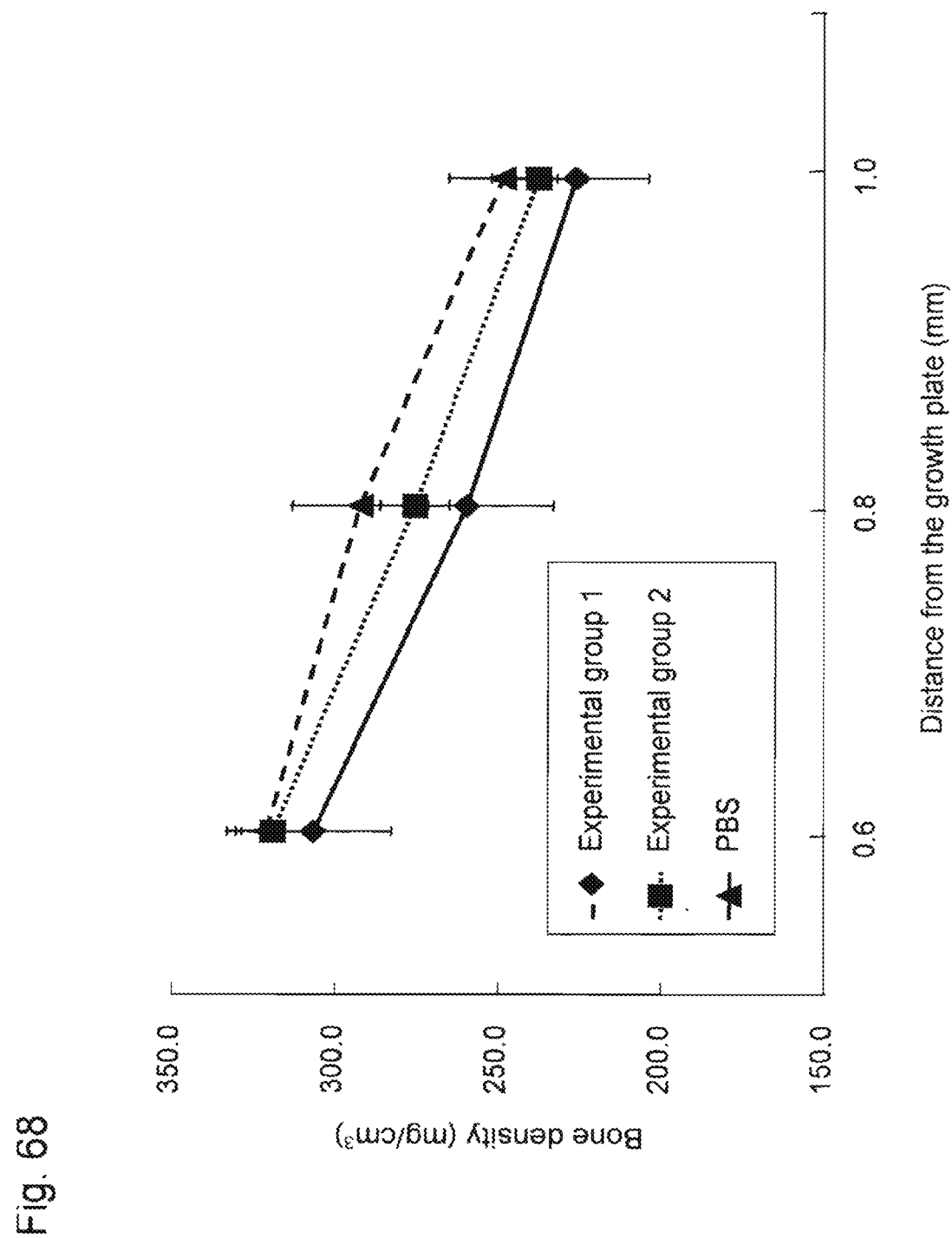
FIG. 68 shows a graph of bone densities in mice each subjected to administration of GST-RANKL or PBS to the calvarium.

As a result of bone density measurement with pQCT, a bone density decrease was observed at the measurement points in the experimental group 1, compared with the PBS group. A bone density decrease was observed at the points 0.8 mm and 1.0 mm from the distal growth plate on the proximal side in the experimental group 2 (FIG. 68).

In addition, the bone density for the experimental group 1 was found to have become smaller than that for the experimental group 2 upon comparison between the experimental groups 1 and 2. Accordingly, it was found that an obvious bone density decrease can be obtained at an identical GST- RANKL dose per day in the case of multiple-dose administration, compared with the case of single-dose administration.

Example 6

Evaluation of RANKL-Signal-Inhibiting Compounds with the Use of Osteopenia Mouse Models GST or GST-RANKL (20 μg) was administered 3 times to 7-week-old female C57BL/6N mice every 24 hours. LFM-A13 (20 mg/kg body weigh) or physiological saline was administered thereto 1 hour before GST-RANKL administration. Measurement of the serum Ca concentration and bone morphology measurement was carried out 1.5 hours after the $3^{rd}$ GST-RANKL administration. In addition, 3D image analysis was carried out with micro CT.

It has been suggested based on analysis with the use of KO mice and the like that Tec and Btk, which are Tec family kinases, play important roles in osteoclast differentiation. LFM-A13 is a drug capable of inhibiting Tec kinase activity by specifically binding to the ATP-binding region of Btk serving as a Tec family kinase (Mahajan et al., J. Biol. Chem., 274, 9587-9599, 1999; Fernandes et al., J. Leukoc. Biol., 78, 524-532, 2005).

Figure 69:
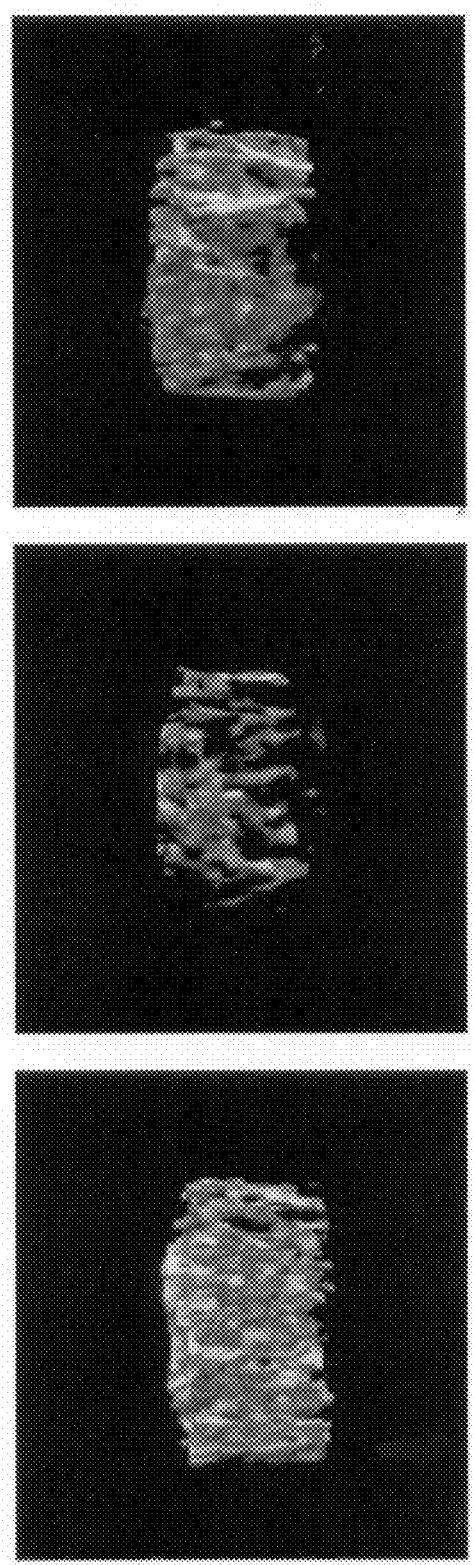
FIG. 69 shows bone mass images of a mouse subjected to administration of GST-RANKL and then subjected to administration of LFM-A13.
Figure 70:
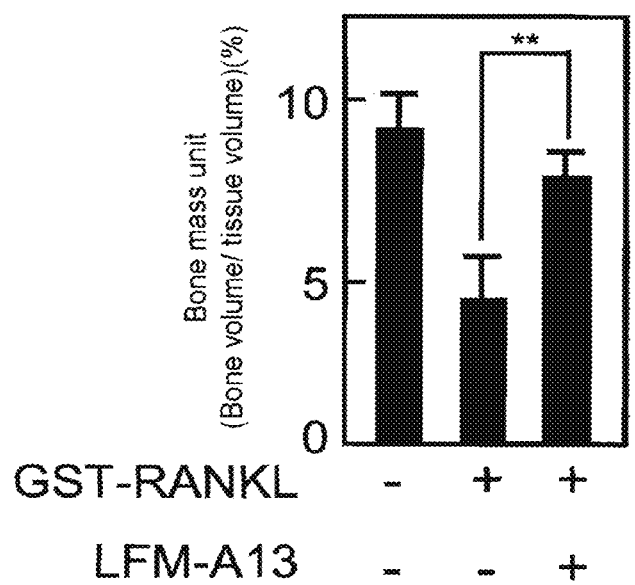
FIG. 70 shows a graph of unit bone masses (bone volume/tissue volume) in mice subjected to administration of GST-RANKL and then subjected to administration of LFM-A13.
Figure 71:
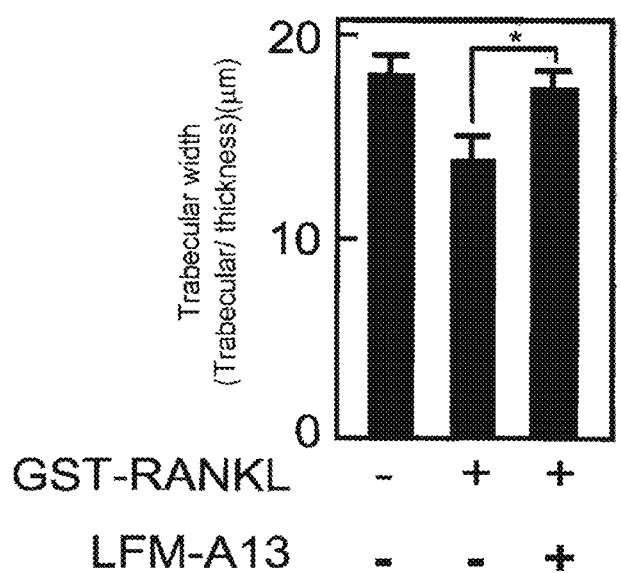
FIG. 71 shows a graph of trabecular widths (trabecular thickness) in mice treated with GST-RANKL and then with LFM-A13.
Figure 72:
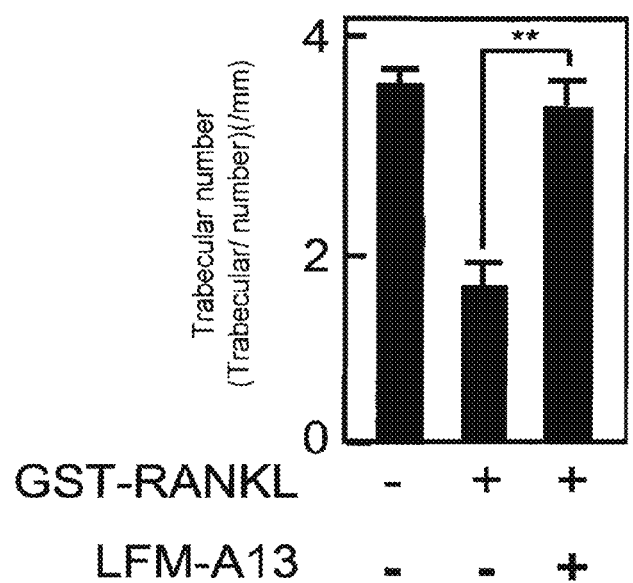
FIG. 72 shows a graph of the trabecular numbers (trabecular number) in mice subjected to administration of GST-RANKL and then subjected to administration of LFM-A13.
Figure 73:
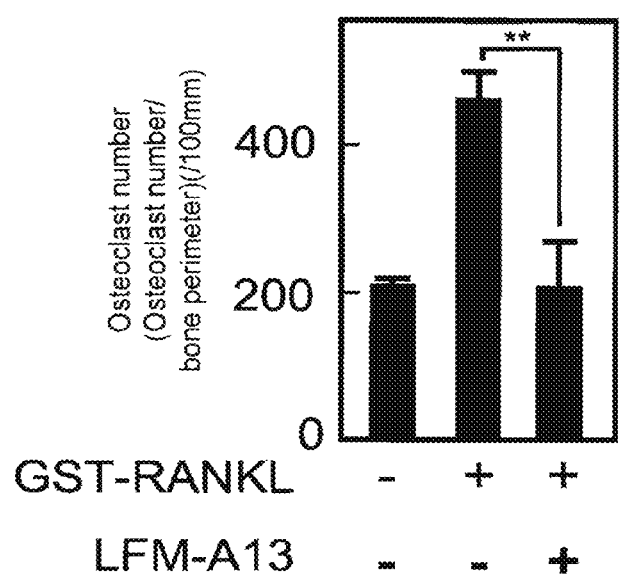
FIG. 73 shows a graph of the osteoclast numbers (osteoclast number/bone perimeter) in mice subjected to administration of GST-RANKL and then subjected to administration of LFM-A13.
Figure 74:
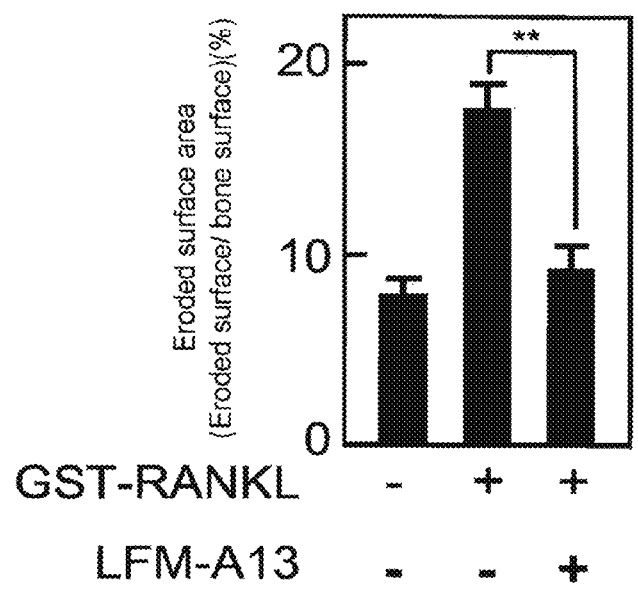
FIG. 74 shows a graph of eroded surface areas (eroded surface area/bone surface area) for mice subjected to administration of GST-RANKL and then subjected to administration of LFM-A13.
Figure 75:
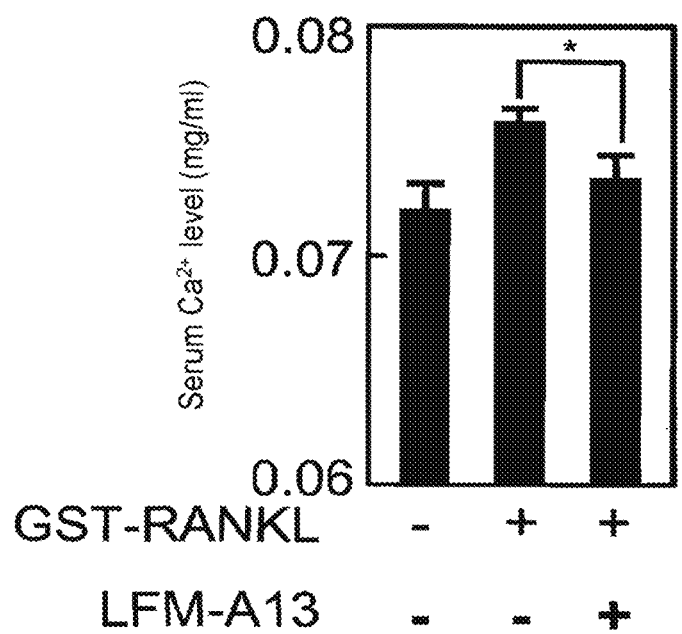
FIG. 75 shows a graph of serum Ca concentrations in mice subjected to administration of GST-RANKL and then subjected to administration of LFM-A13.

The results of image analysis with micro CT indicate that a bone mass decrease caused by GST-RANKL administration was suppressed by LFM-A13 administration (FIG. 69). In addition, upon bone morphology measurement, a decrease in unit bone mass (BV/TV) caused by GST-RANKL administration was found to have been significantly suppressed by LFM-A13 administration ($p<0.01$) (FIG. 70). Decreases in the trabecular width (Tb.Th) and the trabecular number (Tb.N) resulting from GST-RANKL administration were significantly suppressed by LFM-A13 administration ($p<0.05$ and $p<0.01$, respectively) (FIGS. 71 and 72). Increases in the osteoclast number (N.Oc/B.Pm) and the eroded surface area (ES/BS) resulting from GST-RANKL administration were significantly suppressed by LFM-A13 administration ($p<0.01$) (FIGS. 73 and 74). An increase in the serum Ca concentration resulting from GST-RANKL administration was significantly suppressed by LFM-A13 administration ($p<0.05$) (FIG. 75).

The above results revealed that osteopenia models obtained by GST-RANKL administration can be applied to evaluation of drugs capable of inhibiting RANKL signals and studies of mechanisms involving osteoclast differentiation and the like.

Example 7

Examination of Drug Evaluation with the Use of a Selective Estrogen Receptor Modulator (Raloxifene)

GST-RANKL was intraperitoneally administered twice to groups of 7-week-old female C57BL/6N mice at 1 mg/kg every 24 hours. Ovariectomy (OVX) or sham operation (Sham) was carried out 24 hours after the $2^{nd}$ administration. 24 hours later, raloxifene was orally administered at 1 mg/kg or 10 mg/kg every 24 hours for 14 consecutive days. In addition, PBS (i.p.) and ultrapure water (p.o.) were used as control substances for comparison with GST-RANKL and raloxifene, respectively, upon administration. The serum and femur were collected from each mouse 24 hours after raloxifene administration on day 14.

The serum collected from each mouse was subjected to measurement of serum bone resorption markers (Ca and TRAP-5b) and an osteogenesis marker (ALP). Each femur was subjected to measurement of the bone density, the bone mineral content, and the cortical bone thickness with pQCT at points 0.6, 0.8, 1.0 mm from the distal growth plate on the proximal side. In addition, image analysis was carried out with micro CT.

Figure 76:
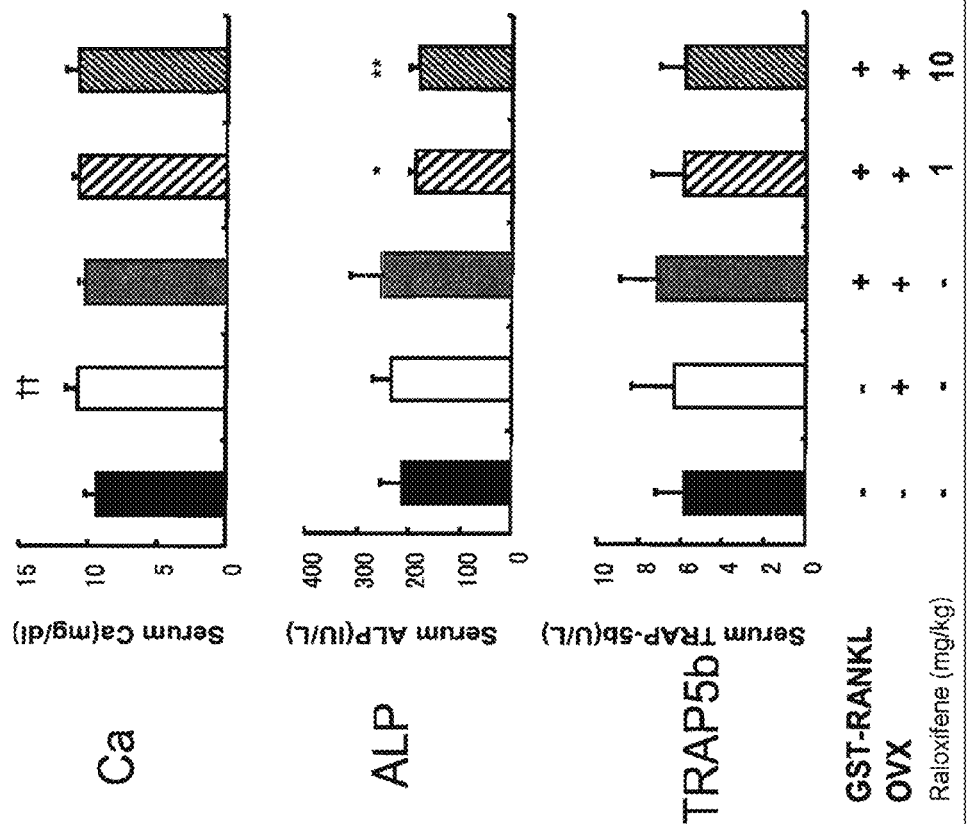
FIG. 76 shows graphs of serum Ca, ALP, and TRAP-5b concentrations in mice subjected to administration of GST-RANKL and then subjected to ovariectomy, to which raloxifene was further administered.
Figure 77:
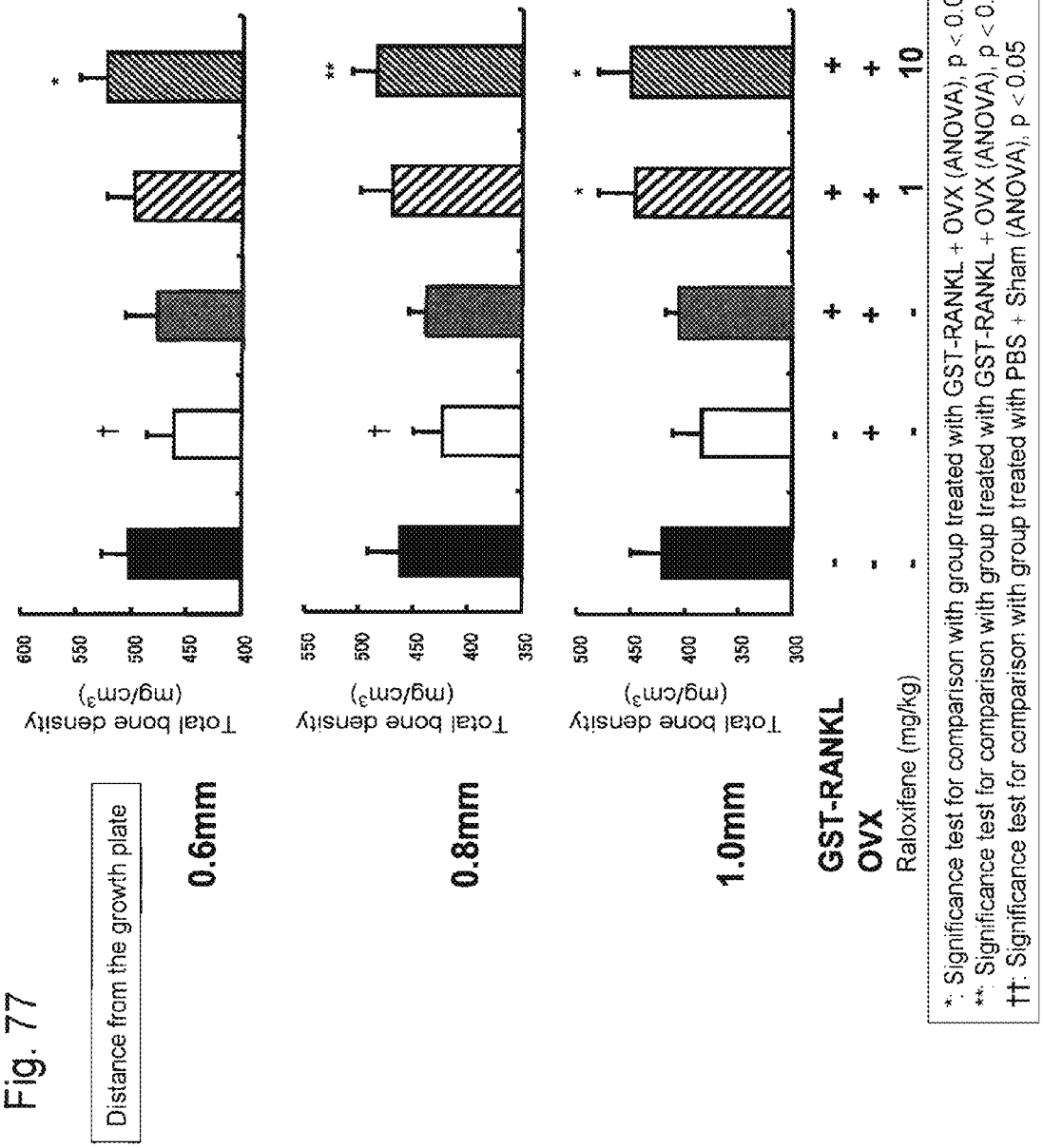
FIG. 77 shows graphs of total bone densities in mice subjected to administration of GST-RANKL and then subjected to ovariectomy, to which raloxifene was further administered.
Figure 78:
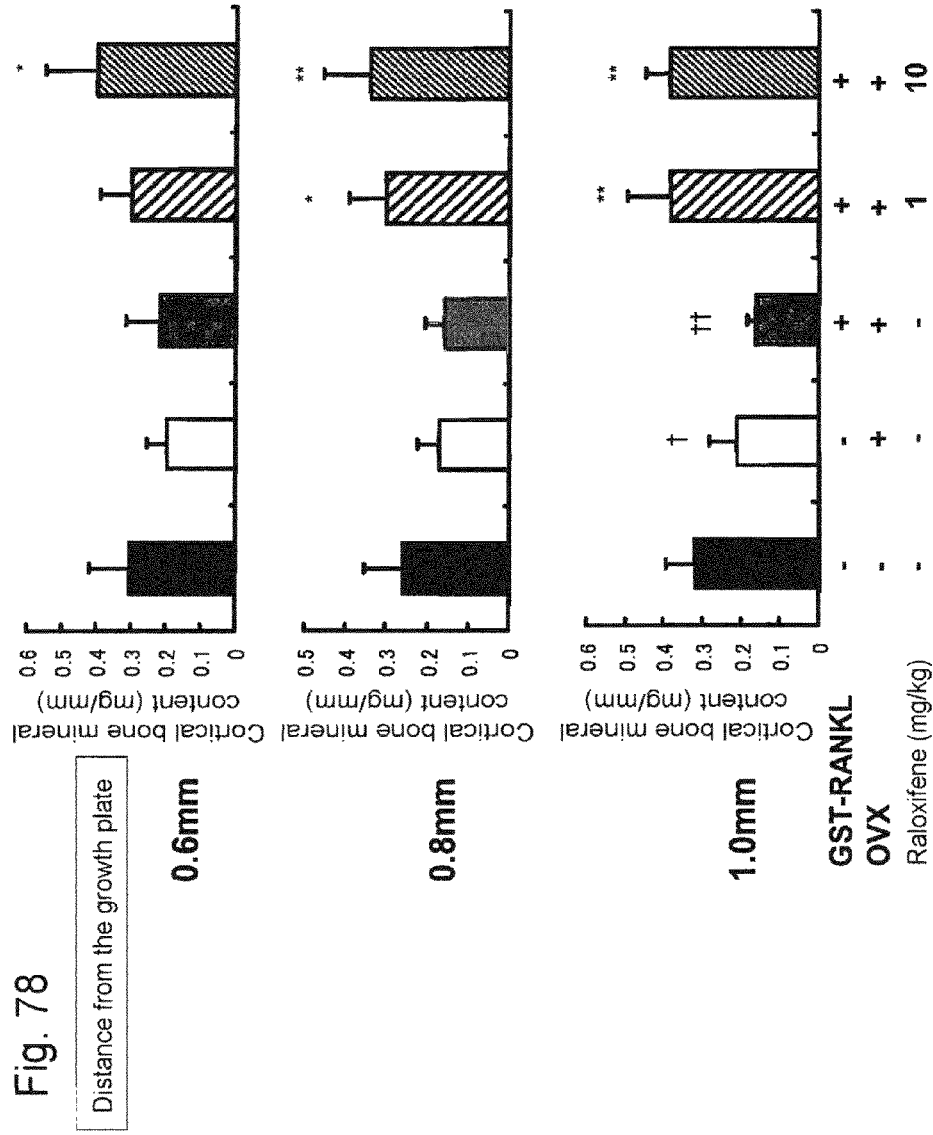
FIG. 78 shows graphs of cortical bone mineral contents in mice subjected to administration of GST-RANKL and then subjected to ovariectomy, to which raloxifene was further administered.
Figure 79:
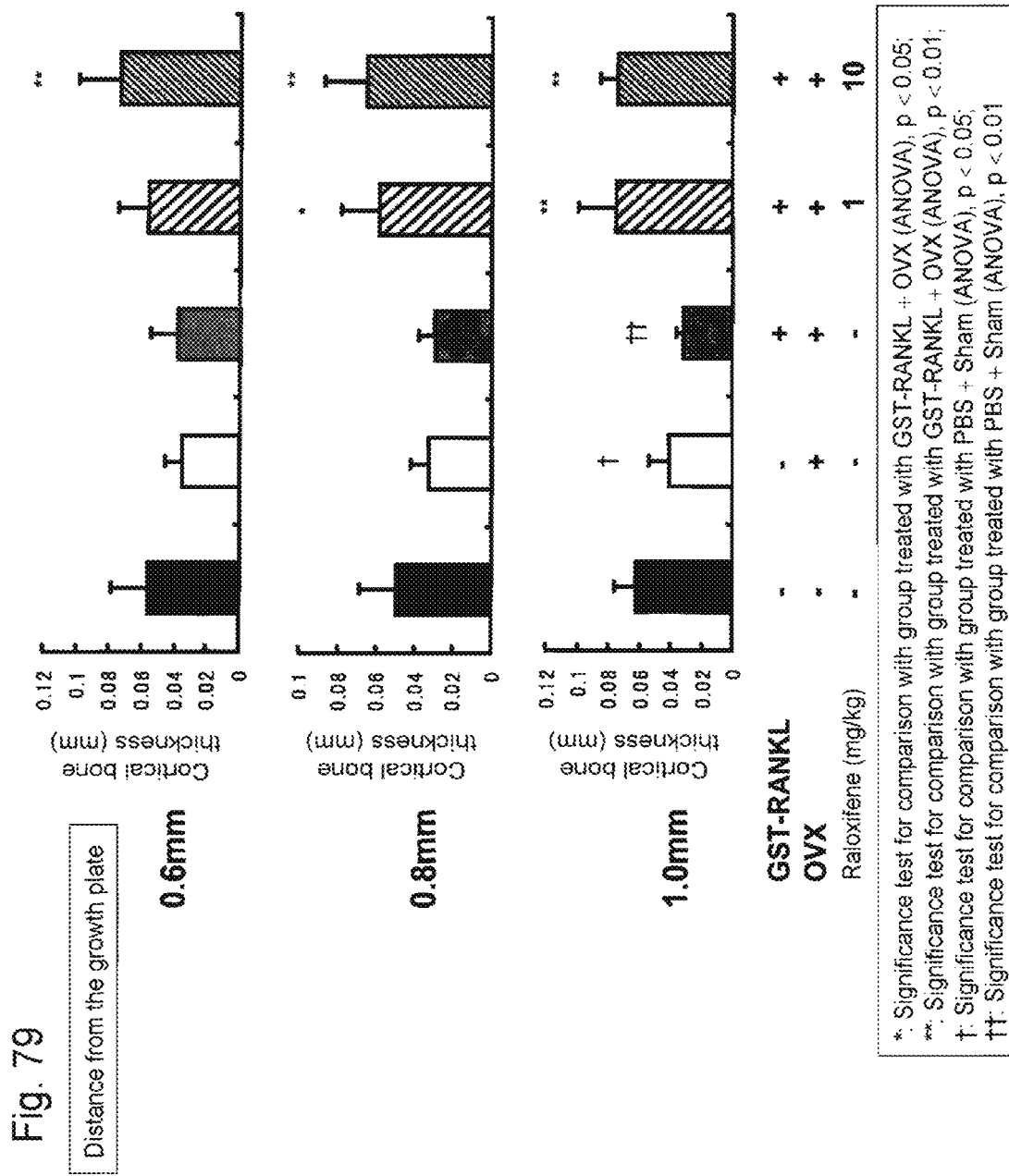
FIG. 79 shows graphs of cortical bone thicknesses in mice subjected to administration of GST-RANKL and then subjected to ovariectomy, to which raloxifene was further administered.
Figure 80:
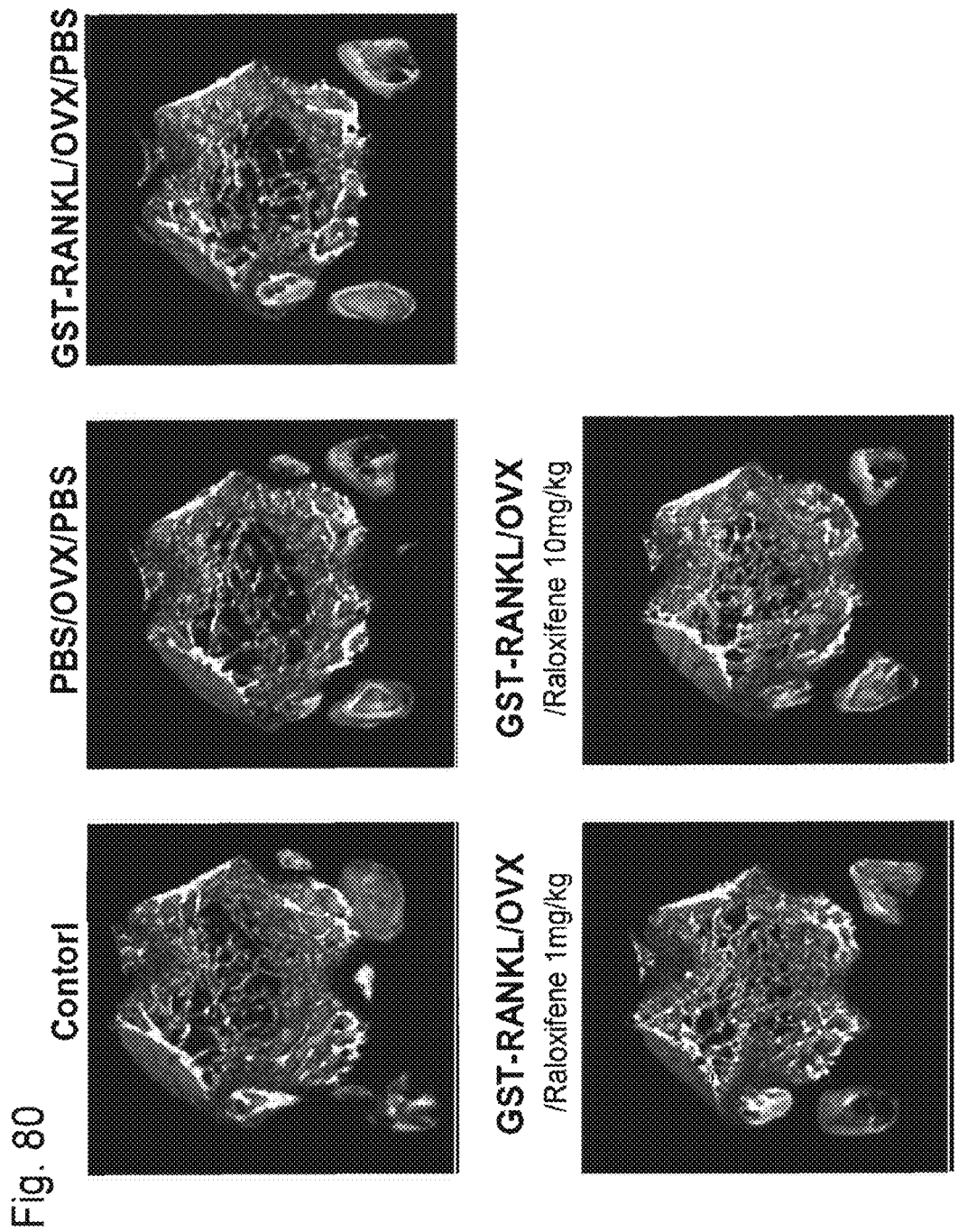
FIG. 80 shows images indicating image analysis results (obtained with micro CT) for mice subjected to administration of GST-RANKL and then subjected to ovariectomy, to which raloxifene was further administered.

There were no significant changes in the serum Ca and TRAP-5b concentrations. The Ca concentration significantly increased exclusively in the PBS administration+OVX group compared with that for the PBS administration+Sham group (FIG. 76). The ALP concentration tended to increase in the GST-RANKL administration+OVX group compared with that for the PBS administration+Sham group. However, the ALP concentration significantly decreased as a result of administration of raloxifene at 1 mg/kg and 10 mg/kg ($p<0.05$ and $p<0.01$, respectively) (FIG. 76). Upon cancellous bone density measurement with the use of pQCT, there were no significant differences among the all groups. Meanwhile, the total bone density significantly decreased in the PBS administration+OVX group compared with that for the PBS administration+Sham group. However, no significant difference was observed in the GST-RANKL administration+OVX group, although the total bone density tended to decrease. The total bone density for the GST-RANKL administration+OVX group increased by 10% ($p<0.05$) and 11% ($p<0.05$) at the point 1.0 mm from the distal growth plate on the proximal side as a result of administration of raloxifene at 1 mg/kg and 10 mg/kg, respectively (FIG. 77). In addition, the total bone density for the GST-RANKL administration+OVX group increased by 10% ($p<0.05$) and 11% ($p<0.05$) at the points 0.6 and 0.8 mm from the distal growth plate on the proximal side, respectively, as a result of administration of raloxifene at 10 mg/kg (FIG. 77). The cortical bone mineral content obtained by measurement with pQCT decreased (at the point 1.0 mm from the distal growth plate on the proximal side of the femur) by 34% ($p<0.05$) and 49% ($p<0.01$) in the PBS administration+OVX group and the GST-RANKL administration+OVX group, respectively, compared with that for the PBS administration+Sham group (FIG. 78). The cortical bone mineral content in the GST-RANKL administration+OVX group increased by 87% ($p<0.05$), 118% ($p<0.01$), and 137% ($p<0.01$) at the points 0.6, 0.8, and 1.0 mm from the distal growth plate on the proximal side, respectively, as a result of administration of raloxifene at 10 mg/kg (FIG. 78). In addition, the cortical bone mineral content in the GST-RANKL administration+OVX group increased by 93% ($p<0.05$) and 136% ($p<0.01$) at the points 0.8 and 1.0 mm from the distal growth plate on the proximal side, respectively, as a result of administration of raloxifene at 1 mg/kg (FIG. 78). Similarly, the cortical bone thickness obtained by measurement with pQCT significantly decreased (at the point 1.0 mm from the distal growth plate on the proximal side) by 35% ($p<0.05$) and 49% ($p<0.01$) in the PBS administration+OVX group and the GST-RANKL administration+OVX group, respectively, compared with that for the PBS administration+Sham group (FIG. 79). The cortical bone thickness in the GST-RANKL administration+OVX group increased by 92% ($p<0.01$), 123% ($p<0.01$), and 133% ($p<0.01$) at the points 0.6, 0.8, and 1.0 mm from the distal growth plate on the proximal side, respectively, as a result of administration of raloxifene at 10 mg/kg (FIG. 79). In addition, the cortical bone thickness in the GST-RANKL administration+OVX group increased by 101% ($p<0.05$) and 137% ($p<0.01$) at the points 0.8 and 1.0 mm from the distal growth plate on the proximal side, respectively, as a result of administration of raloxifene at 1 mg/kg (FIG. 79). Similar results were confirmed by image analysis with the use of micro CT (FIG. 80). The above results revealed that osteopenia mouse models obtained by RANKL administration can be used for drug evaluation for selective estrogen receptor modulators such as raloxifene.

Example 8

Evaluation of a Bone Mass Increase with the Use of Low-Dose PTH

GST-RANKL was intraperitoneally administered 2 times to groups of 7-week-old female C57BL/6N mice at 1 mg/kg every 24 hours. PTH was subcutaneously administered thereto at 40 or 80 μg/kg from 24 hours after the $2^{nd}$ administration every 24 hours for 10 consecutive days. In addition, PBS was administered to a group serving as the control group for the GST-RANKL and PTH administration groups for comparison. The serum and femur were collected from each mouse 24 hours after the end of administration for 10 days.

The serum collected from each mouse was subjected to measurement of serum bone resorption markers (Ca and TRAP-5b) and an osteogenesis marker (ALP). Each femur was subjected to measurement of the total bone density, the cortical bone density, the cortical bone thickness, the cortical bone mineral content, and the cortical bone density in the diaphysis with pQCT at points 0.6, 0.8, and 1.0 mm from the distal growth from the distal growth plate on the proximal side. In addition, image analysis was carried out with micro CT.

Figure 81:
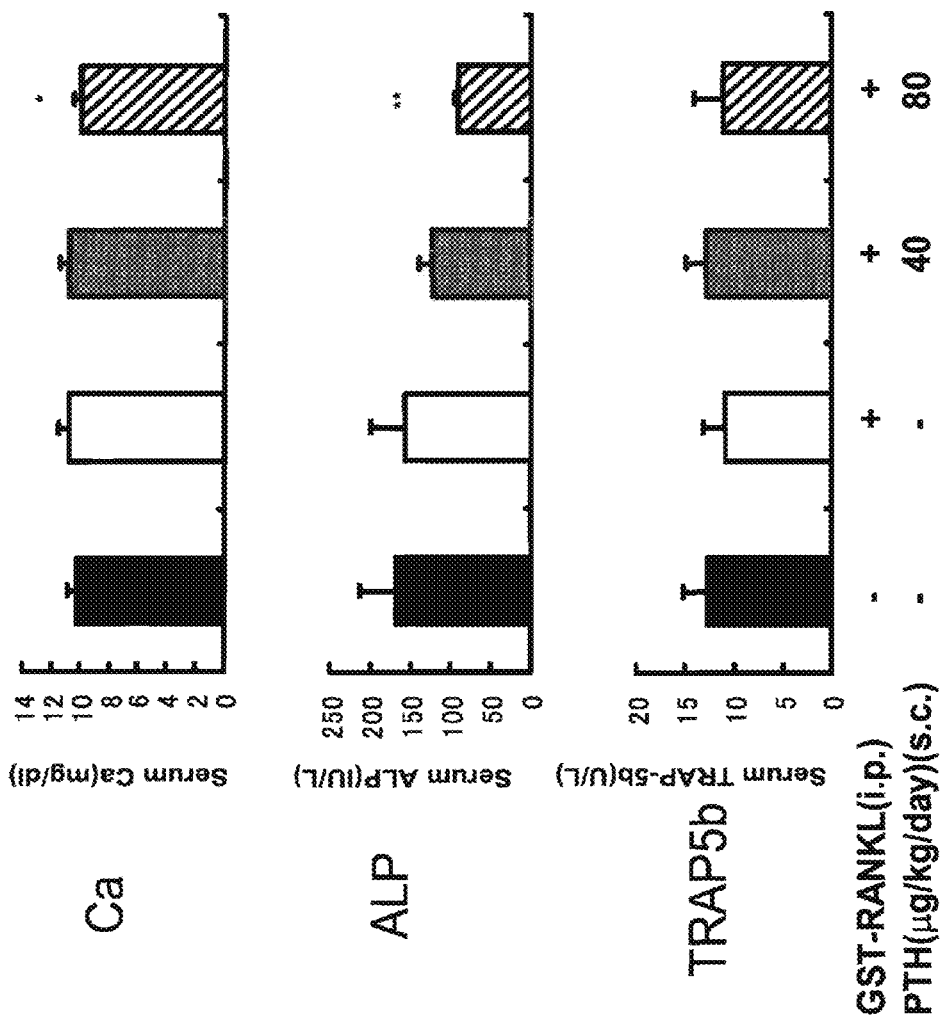
FIG. 81 shows graphs of serum Ca, ALP, and TRAP-5b concentrations in mice subjected to administration of GST-RANKL and then subjected to ovariectomy, to which raloxifene was further administered.
Figure 82:
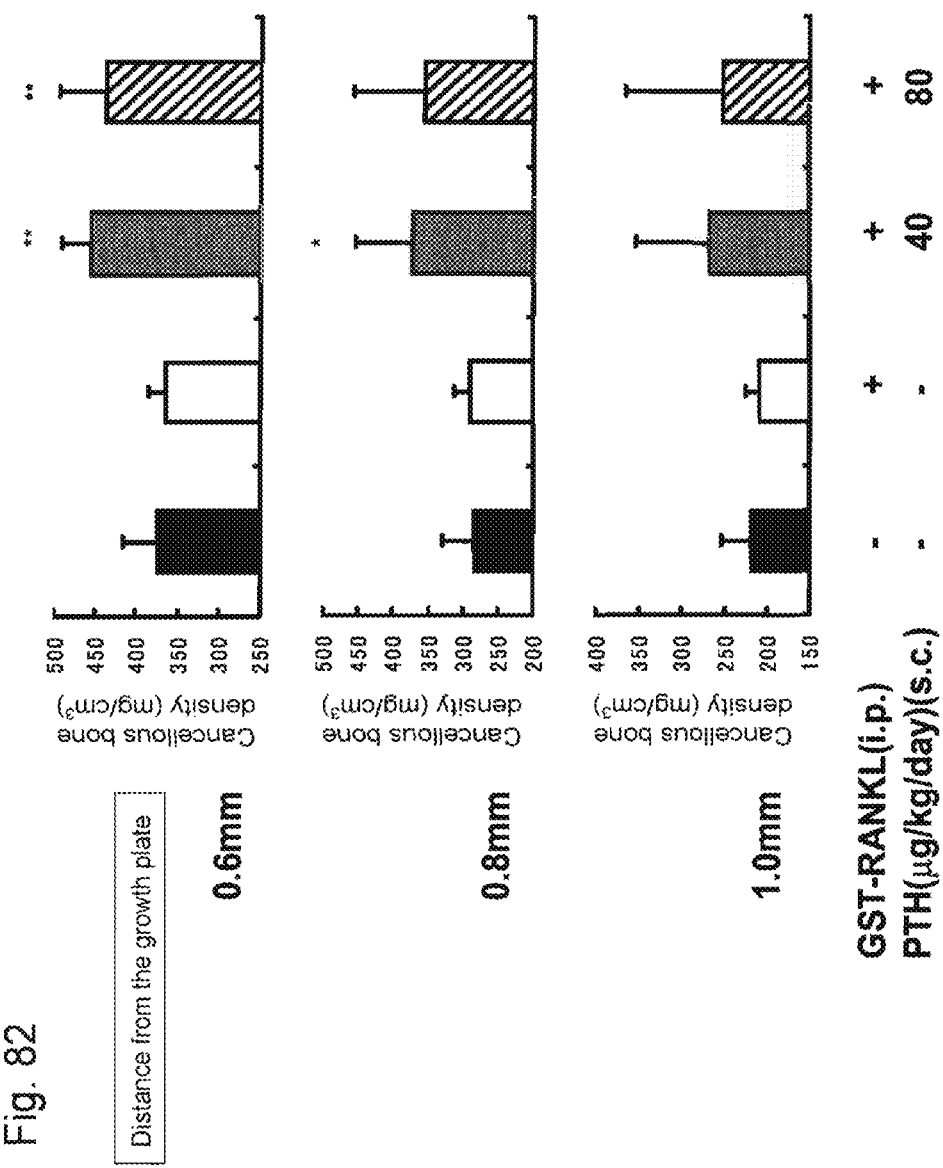
FIG. 82 shows graphs of cancellous bone densities in mice subjected to administration of GST-RANKL and then subjected to ovariectomy, to which raloxifene was further administered.
Figure 83:
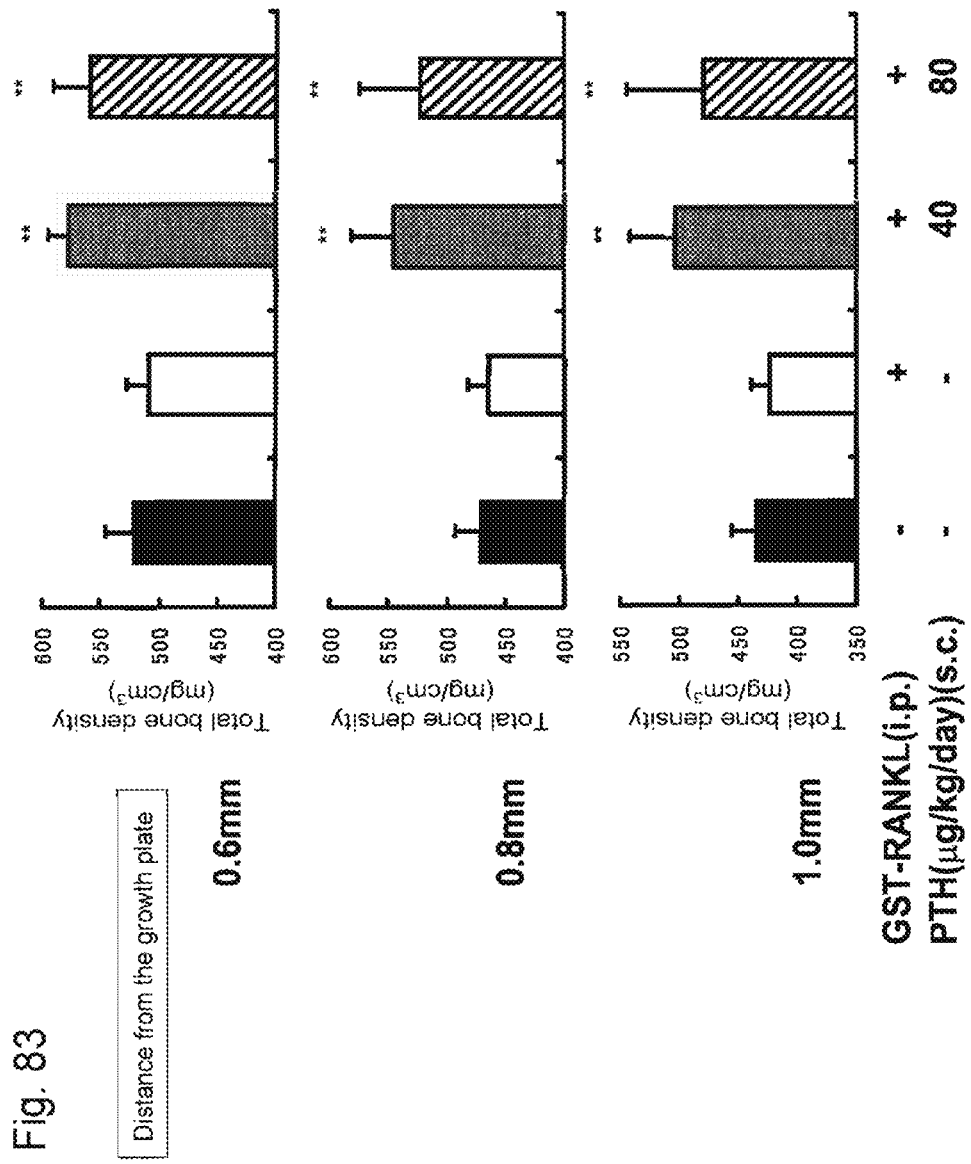
FIG. 83 shows graphs of total bone densities in mice subjected to administration of GST-RANKL and then subjected to administration of PTH.
Figure 84:
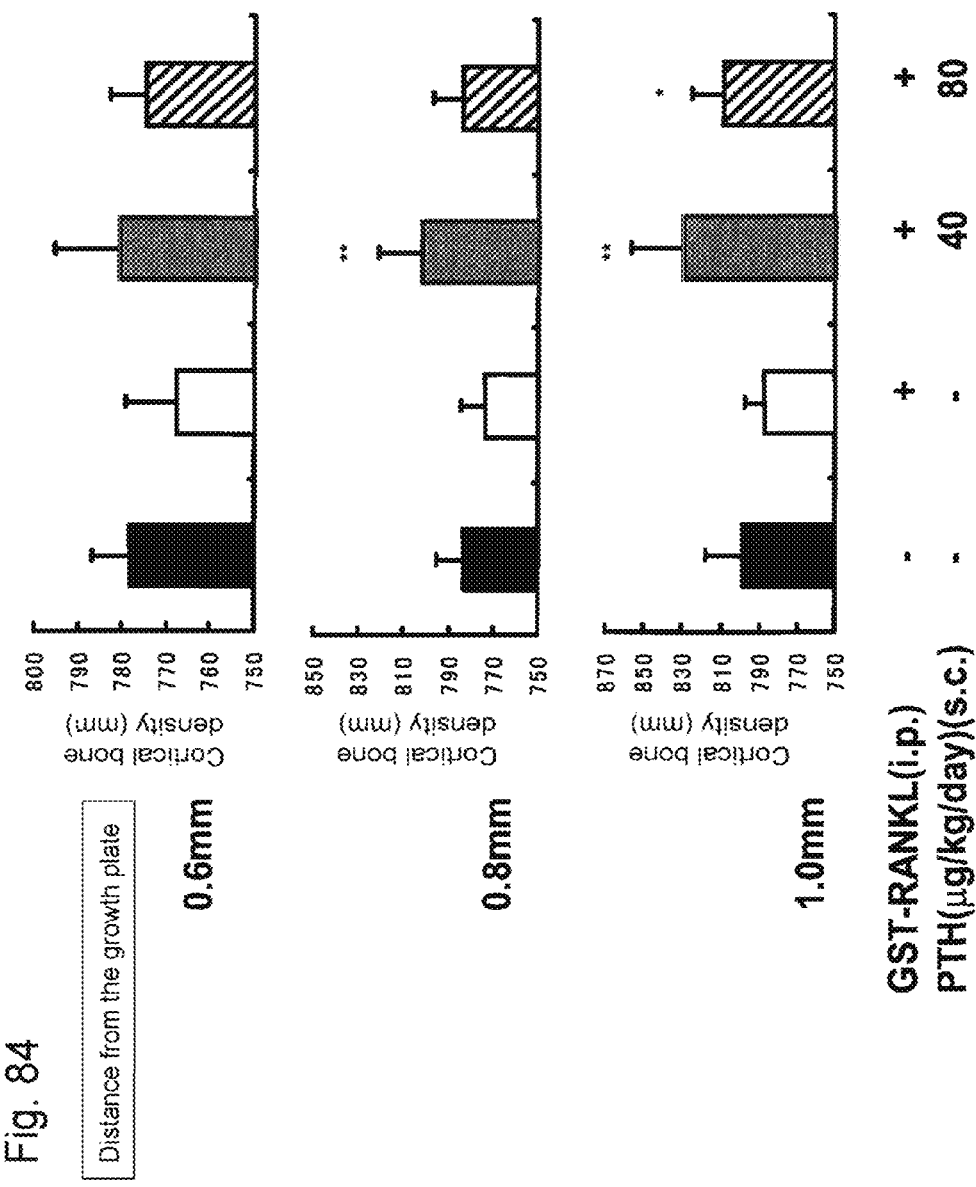
FIG. 84 shows graphs of cortical bone densities in mice subjected to administration of GST-RANKL and then subjected to administration of PTH.
Figure 85:
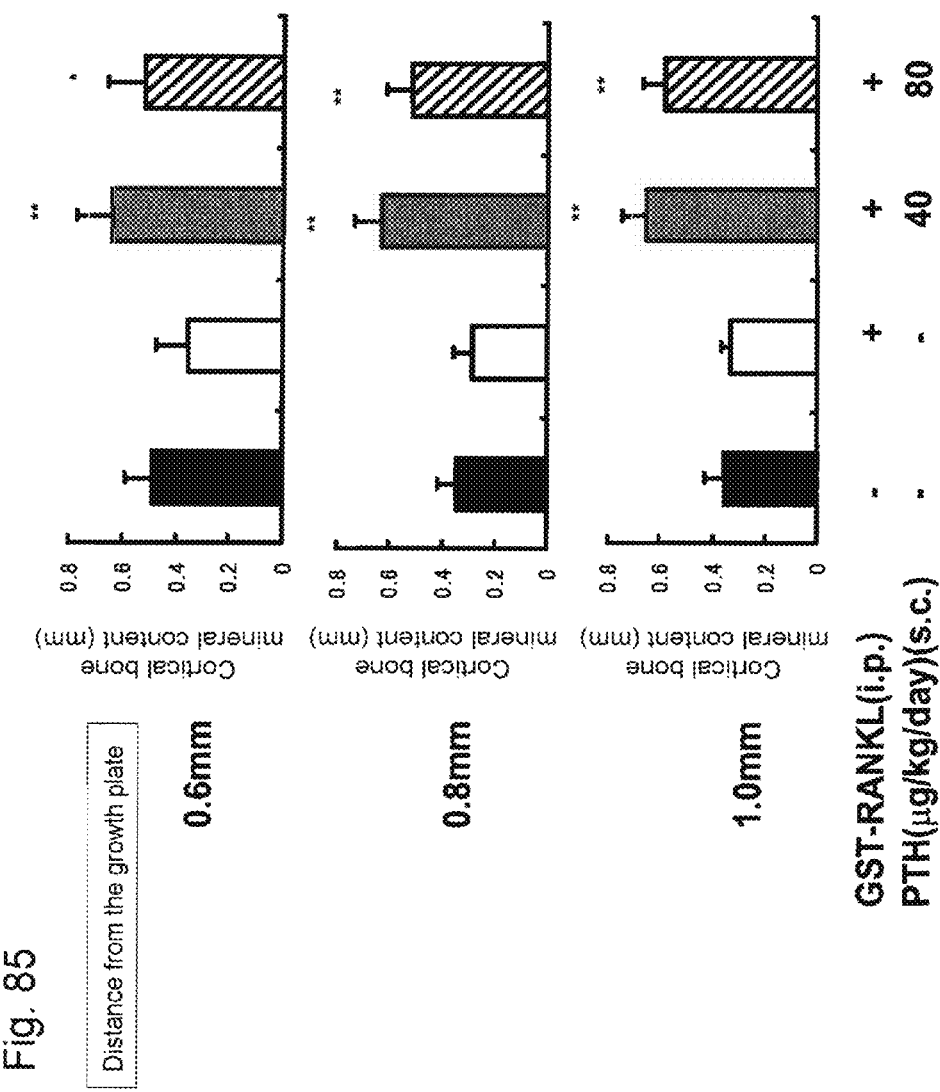
FIG. 85 shows graphs of cortical bone mineral contents in mice subjected to administration of GST-RANKL and then subjected to administration of PTH.
Figure 86:
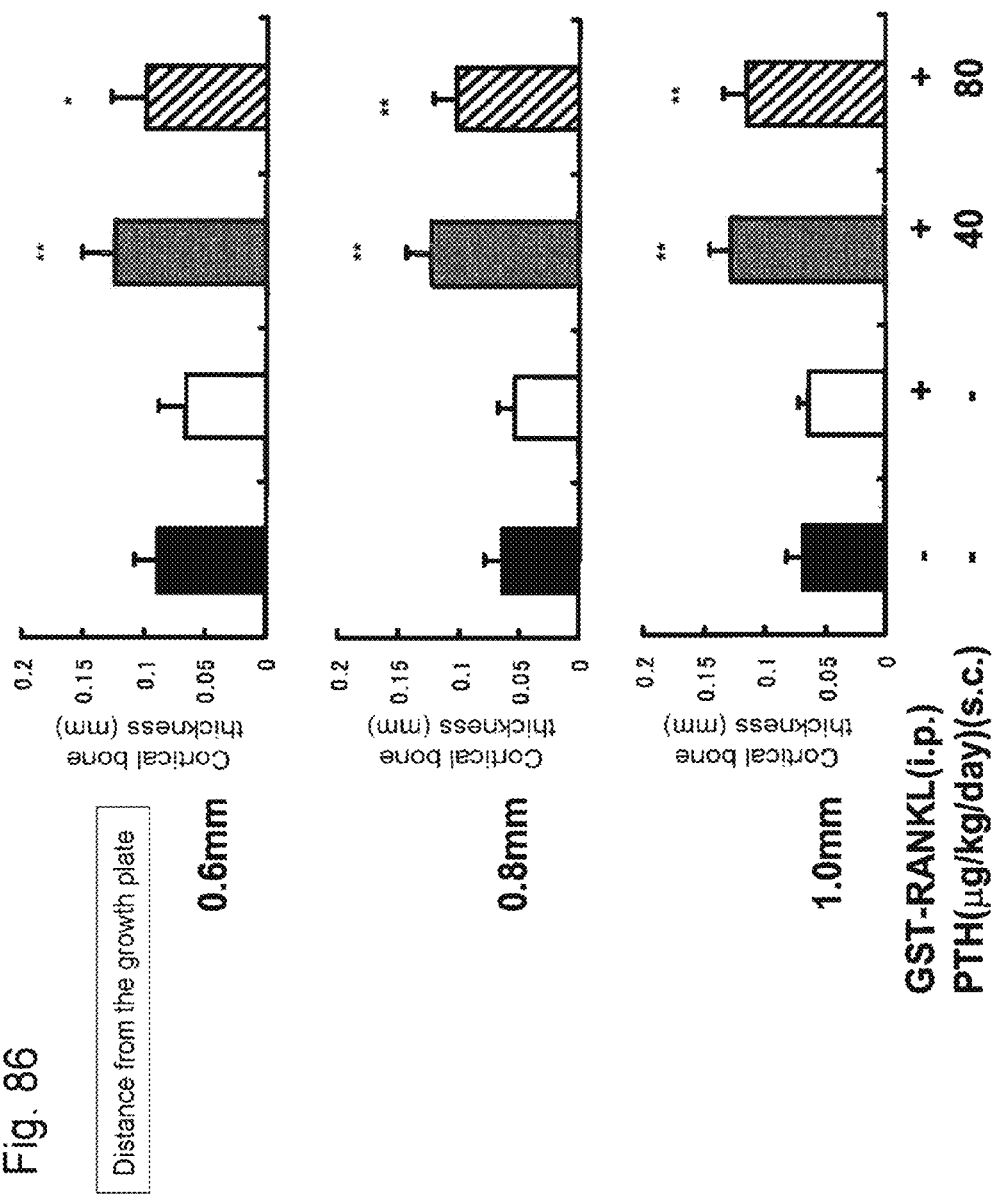
FIG. 86 shows graphs of cortical bone thicknesses in mice subjected to administration of GST-RANKL and then subjected to administration of PTH.
Figure 87:
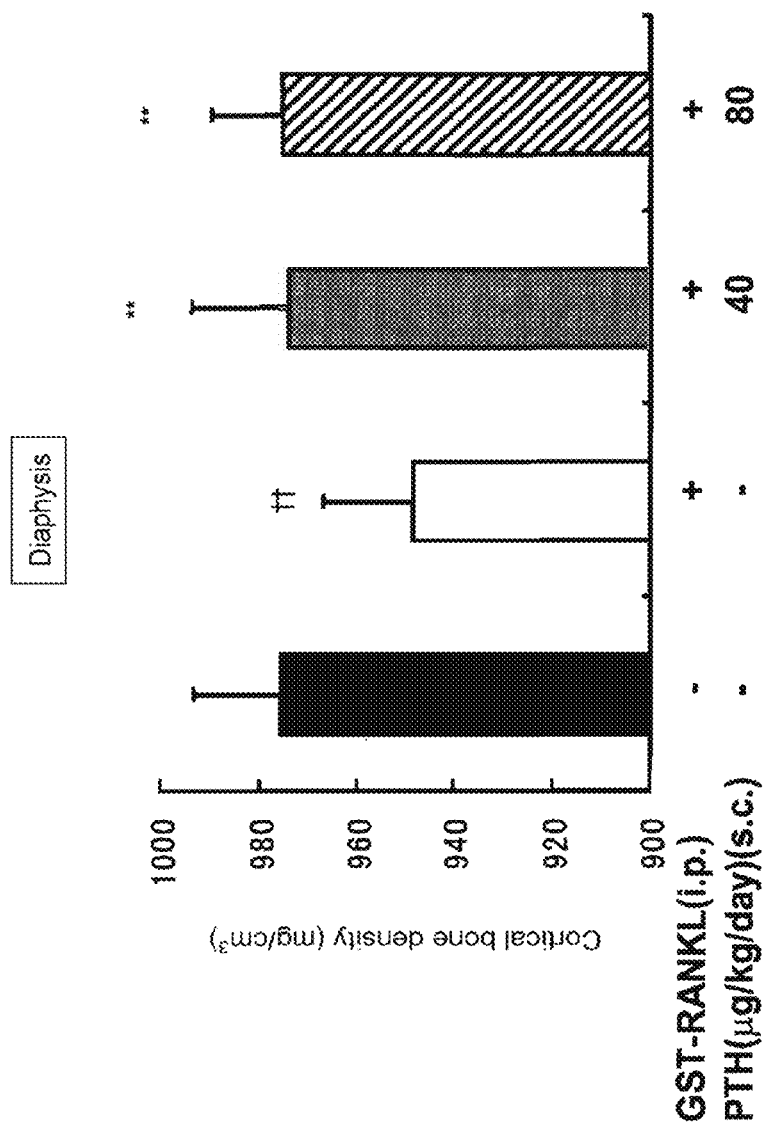
FIG. 87 shows a graph of cortical bone densities the cortical bone density in the diaphyses of mice subjected to administration of GST-RANKL and then subjected to administration of PTH.
Figure 88:
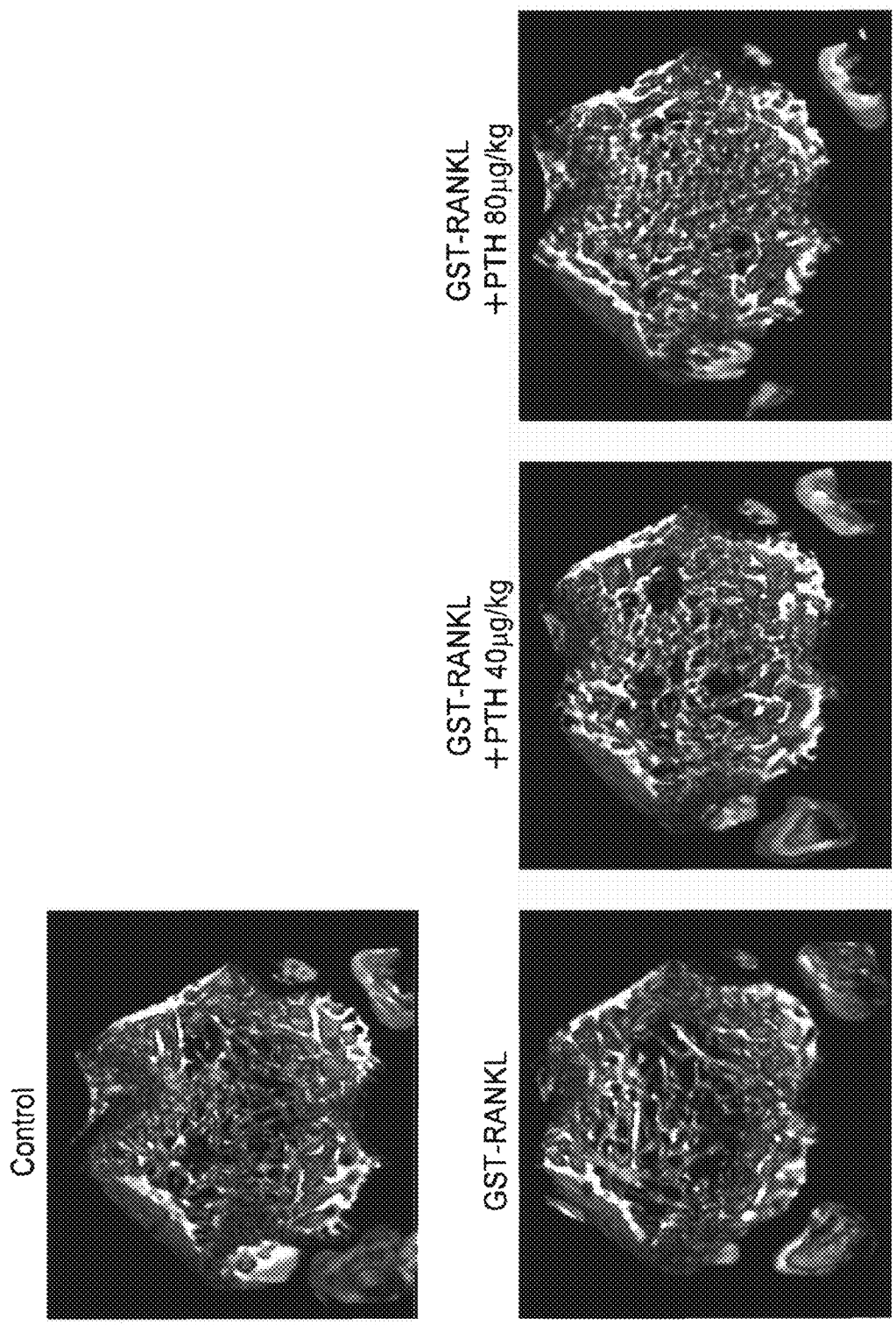
FIG. 88 shows images indicating image analysis results (obtained with micro CT) for mice subjected to administration of GST-RANKL and then subjected to administration of PTH.

There were no significant changes in the serum Ca and TRAP-5b concentrations. Regarding the Ca concentration, a slightly significant decrease was observed in the GST-RANKL administration group as a result of PTH administration at 80 μg/kg ($p<0.05$) (FIG. 81). Meanwhile, the ALP concentration significantly decreased in the GST-RANKL administration group as a result of PTH administration at 80 μg/kg ($p<0.01$). Also, the concentration tended to decrease as a result of PTH administration at 40 μg/kg (FIG. 81). The cancellous bone density for the GST-RANKL administration group increased by 25% ($p<0.01$) and 28% ($p<0.05$) at the points 0.6 and 0.8 mm from the distal growth from the distal growth plate on the proximal side, respectively, as a result of PTH administration at 40 μg/kg, compared with that for the PBS administration group (FIG. 82). In addition, the cancellous bone density for the GST-RANKL administration group increased by 20% ($p<0.01$) at the point 0.6 mm from the distal growth from the distal growth plate on the proximal side as a result of PTH administration at 80 μg/kg (FIG. 82). Meanwhile, the total bone density increased in the GST-RANKL administration group by 14% ($p<0.01$), 17% ($p<0.01$), and 19% ($p<0.01$) at the points 0.6, 0.8, and 1.0 mm from the distal growth from the distal growth plate on the proximal side, respectively, as a result of PTH administration at 40 μg/kg, compared with that for the PBS administration group (FIG. 83). In addition, the total bone density similarly increased in the GST-RANKL administration group by 10% ($p<0.01$), 13% ($p<0.01$), and 13% ($p<0.01$) at the above points as a result of PTH administration at 80 μg/kg (FIG. 83). The cortical bone density for the GST-RANKL administration group increased by 4% ($p<0.01$) and 5% ($p<0.01$) at the points 0.8 and 1.0 mm from the distal growth from the distal growth plate on the proximal side, respectively, as a result of PTH administration at 40 μg/kg, compared with that for the PBS administration group (FIG. 84). In addition, the cortical bone density for the GST-RANKL administration+OVX group increased by 3% ($p<0.05$) at the point 1.0 mm from the distal growth from the distal growth plate on the proximal side as a result of PTH administration at 80 μg/kg (FIG. 84). The cortical bone mineral content for the GST-RANKL administration group increased by 80% ($p<0.01$), 123% ($p<0.01$), and 100% ($p<0.01$) at the points 0.6, 0.8, and 1.0 mm from the distal growth plate on the proximal side, respectively, as a result of PTH administration at 40 μg/kg, compared with that for the PBS administration group. Also, the cortical bone mineral content increased by 46% ($p<0.05$), 83% ($p<0.01$), and 77% ($p<0.01$) at the above points as a result of PTH administration at 80 μg/kg (FIG. 85). Similarly, the cortical bone thickness for the GST-RANKL administration group increased by 86% ($p<0.01$), 127% ($p<0.01$), and 98% ($p<0.01$) at the points 0.6, 0.8, and 1.0 mm from the distal growth plate on the proximal side, respectively, as a result of PTH administration at 40 μg/kg, compared with that for the PBS administration group. Also, the cortical bone thickness increased by 50% ($p<0.05$), 89% ($p<0.01$), and 79% ($p<0.01$) at the above points as a result of PTH administration at 80 μg/kg (FIG. 86). Meanwhile, the cortical bone density in the diaphysis decreased by 3% ($p<0.01$) as a result of GST-RANKL administration, compared with that for the control group obtained by PBS administration (FIG. 87). The cortical bone density in the diaphysis for the GST-RANKL administration group increased by 3% ($p<0.01$) and 3% ($p<0.01$) as a result of PTH administration at 40 and 80 μg/kg, respectively, compared with that for the group obtained by PBS administration (FIG. 87). Similar results were confirmed by image analysis with the use of micro CT (FIG. 88).

The above results revealed that bone mass increasing effects of low-dose PTH can be detected in osteopenia mouse models obtained by RANKL administration in a short period of time.

Example 9

Production of Osteopenia Mouse Models Obtained by Administering a Fused Protein of Soluble RANKL with GST to 12-Week-Old Mice GST-RANKL was intraperitoneally administered 3 times to 12-week-old male and female C57BL/6N mice at 1 mg/kg every 24 hours. The serum and femur were collected from each mouse 1.5 hours after the $3^{rd}$ administration. The serum collected from each mouse was subjected to measurement of serum bone resorption markers (Ca and TRAP-5b) and an osteogenesis marker (ALP). Each femur was subjected to bone density measurement by dual energy X-ray absorptiometry (DEXA) and image analysis with micro CT.

Figure 89:
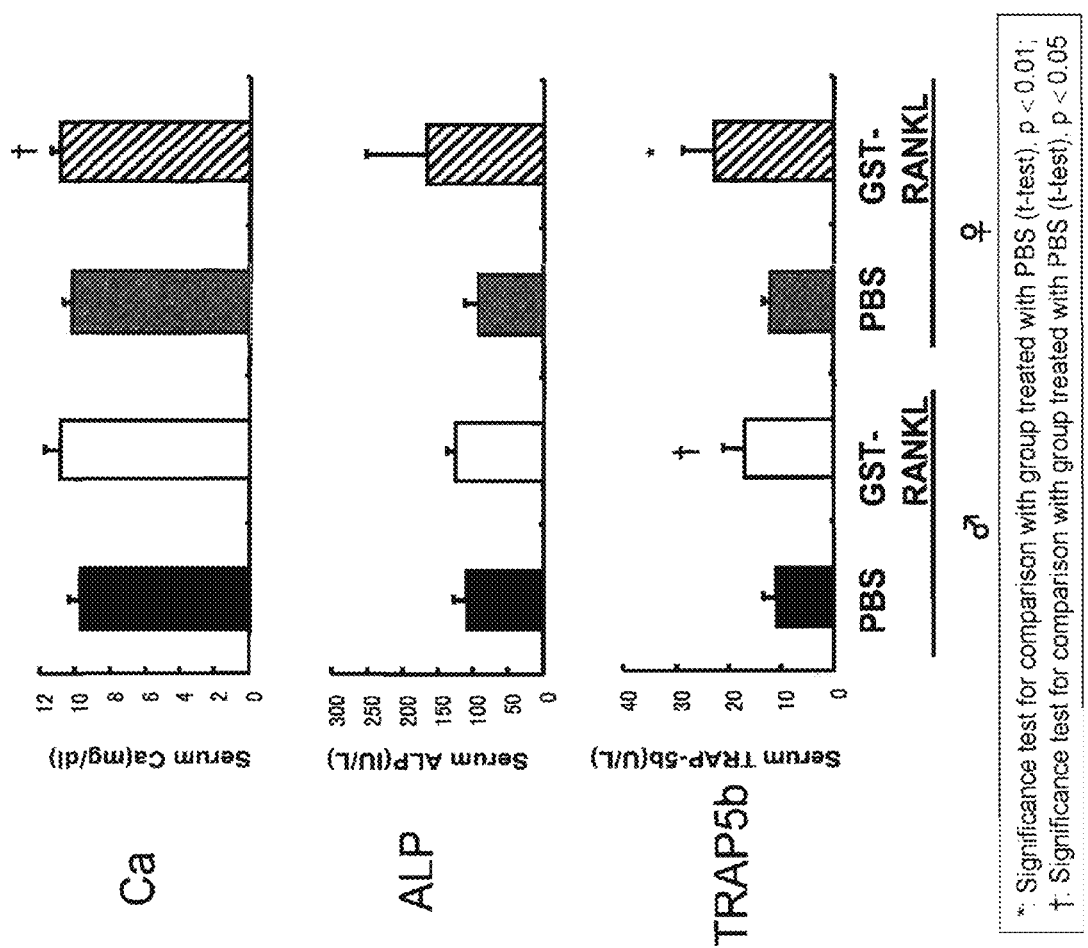
FIG. 89 shows graphs of serum Ca, ALP, and TRAP-5b concentrations in 12-week-old mice subjected to administration of GST-RANKL and then subjected to administration of PTH.
Figure 90:
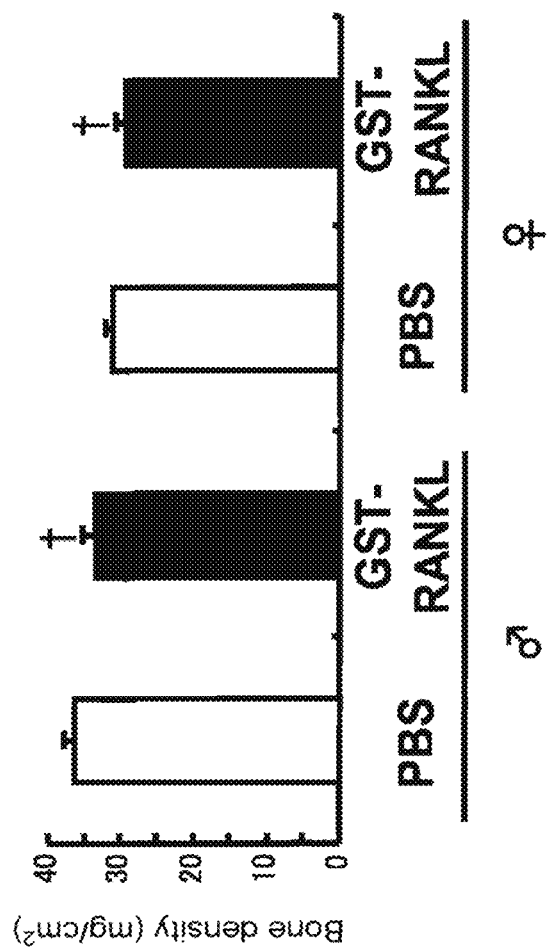
FIG. 90 shows a graph of total bone densities in 12-week-old mice subjected to administration of GST-RANKL.
Figure 91:
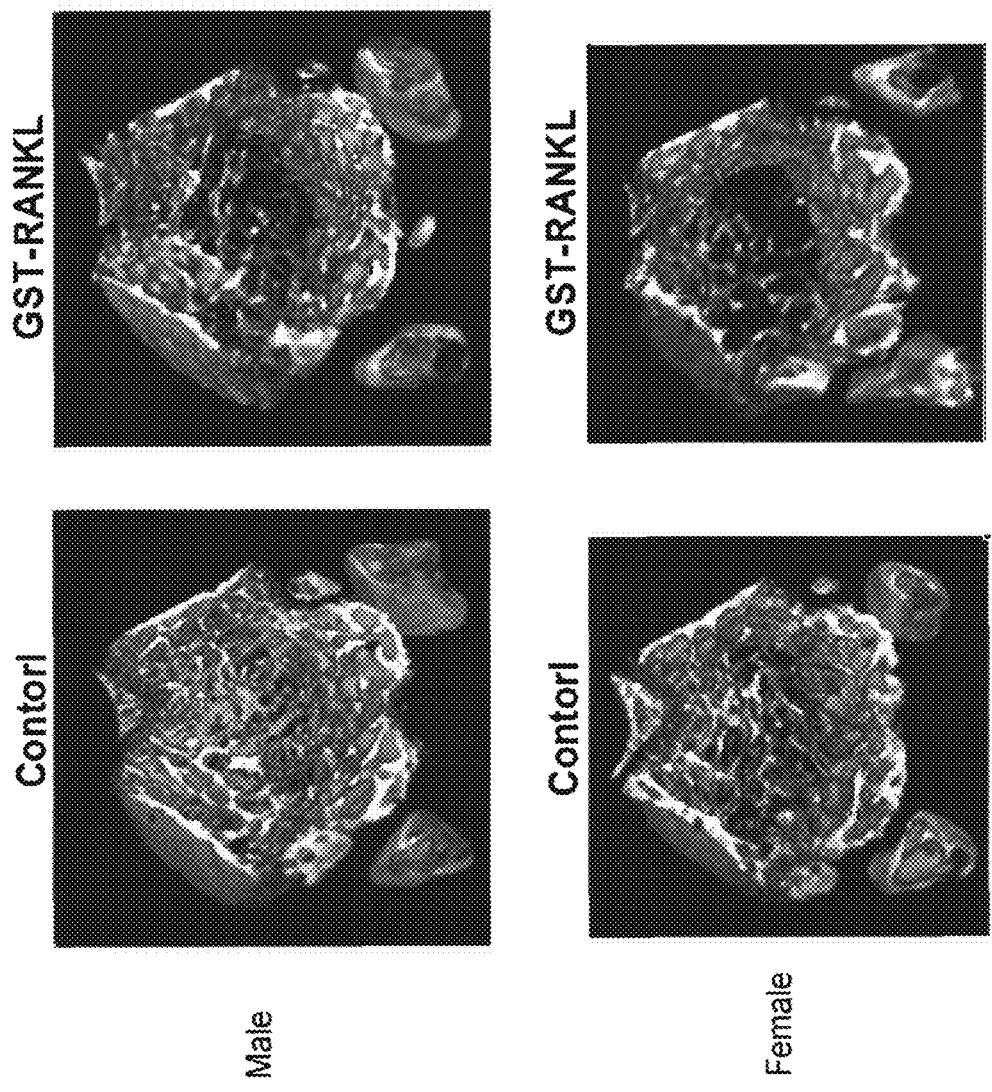
FIG. 91 shows images indicating image analysis results (obtained with micro CT) for 12-week-old mice subjected to administration of GST-RANKL.

The serum TRAP-5b concentration for the male group obtained by GST-RANKL administration significantly increased, compared with that for the male group obtained by PBS administration ($p<0.05$). The Ca and ALP concentrations tended to increase; however, no significant difference was observed (FIG. 89). Meanwhile, the serum Ca and TRAP-5b concentrations for the female group obtained by GST-RANKL administration significantly increased, compared with those for the female group obtained by PBS administration ($p<0.05$ and $p<0.01$, respectively). Although the ALP concentration tended to increase, no significant difference was observed (FIG. 89). As a result of bone density measurement by DEXA, the total bone densities for the male and female GST-RANKL administration groups were found to have decreased by 8% ($p<0.05$) and 6% ($p<0.05$), respectively, compared with those for the control groups (FIG. 90). Also, the above results were confirmed by image analysis with the use of micro CT (FIG. 91). The results for 12-week-old male and female mice revealed that it is also possible to use relatively aged male and female mice as osteopenia mouse models obtained by RANKL administration, regardless of age in weeks. In addition, it was found that osteopenia mouse models obtained by RANKL administration can be produced even with the use of 12-week-old mice, regardless of gender.

INDUSTRIAL APPLICABILITY

According to the present invention, osteopenia animal models can be produced in a rapid manner based on a simple mechanism involving direct promotion of osteoclast differentiation and activation by administration of soluble RANKL or a fused protein of soluble RANKL with an epitope tag. Also, drug evaluation can be carried out in a rapid manner with the use of the thus obtained osteopenia animal models. In addition, since RANKL directly causes osteoclast differentiation and activation in the osteopenia animal model of the present invention, actual effects of a bone resorption suppressant upon osteolysis induced by osteoclasts can be evaluated. Further, a bone mass increasing agent can be evaluated on the basis of the shortness of the period required for restoring the bone mass of the osteopenia animal model to the initial level.

Further, an osteopenia animal model in a state similar to a physiological menopause state in terms of hormonal balance can be produced with the use of a combination of ovariectomy and administration of soluble RANKL or a fused protein of soluble RANKL with an epitope tag in a more rapid manner compared with the case of a conventional ovariectomized model that can be produced in several weeks.

The osteopenia animal model of the present invention can be used for screening for a drug used for treatment and the like for bone metabolism diseases. Further, it can be used as an animal for bone metabolism disease studies.

All publications, patents, and patent applications cited herein are incorporated herein by reference in their entirety.

FREE TEXT OF SEQUENCE LISTING

SEQ ID NOS: 3 to 18 (synthesized)

The invention claimed is:

1. A method for producing an osteopenia animal model, comprising administering a soluble receptor activator of NF-κB ligand ("RANKL") or a fused protein of the soluble RANKL with an epitope tag to a non-human animal so as to promote in vivo osteoclast differentiation and activation in the non-human animal, wherein said administering of the soluble RANKL or the fused protein of the soluble RANKL with an epitope tag induces osteopenia in said non-human animal and produces an osteopenia animal model.

2. The method for producing an osteopenia animal model according to claim 1, wherein the epitope tag is glutathione-S-transferase.

3. The method for producing an osteopenia animal model according to claim 1, wherein the osteopenia animal model is produced within 1 week after administration of the soluble RANKL or the fused protein of the soluble RANKL with an epitope tag to the non-human animal.

4. The method for producing an osteopenia animal model according to claim 3, wherein the osteopenia animal model is produced within 50 hours.

5. The method for producing an osteopenia animal model according to claim 3, wherein the osteopenia animal model is produced within 24 hours.

6. The method for producing an osteopenia animal model according to claim 1, wherein the non-human animal is a rodent animal.

7. The method for producing an osteopenia model according to claim 6, wherein the rodent animal is a mouse or a rat.

8. The method for producing an osteopenia animal model according to claim 1, wherein severity of the osteopenia induced in said non-human animal is dependent upon an amount of said soluble RANKL or said fused protein of the soluble RANKL with an epitope tag administered to the non-human animal.

9. The method for producing an osteopenia animal model according to claim 1, wherein the non-human animal to which the soluble RANKL or the fused protein of the soluble RANKL with an epitope tag is administered is further subjected to ovariectomy.

10. The method for producing an osteopenia animal model according to claim 9, wherein the osteopenia animal model is produced within 72 hours after administration of the soluble RANKL or the fused protein of the soluble RANKL with an epitope tag to the non-human animal.

* * * * *